US008790897B2

(12) United States Patent
Quinn et al.

(10) Patent No.: US 8,790,897 B2
**(45) Date of Patent: *Jul. 29, 2014**

(54) TREATMENT OF MUCUS HYPERSECRETION

(75) Inventors: Conrad Padraig Quinn, Lilburn, GA (US); Keith Alan Foster, Salisbury (GB); John Chaddock, Salisbury (GB)

(73) Assignee: Syntaxin Ltd., Abingdon, Oxon (GB)

( * ) Notice: Subject to any disclaimer, the term of this patent is extended or adjusted under 35 U.S.C. 154(b) by 1221 days.

This patent is subject to a terminal disclaimer.

(21) Appl. No.: 11/806,496

(22) Filed: May 31, 2007

(65) Prior Publication Data

US 2008/0032928 A1 Feb. 7, 2008

Related U.S. Application Data

(63) Continuation-in-part of application No. 11/518,213, filed on Sep. 11, 2006, which is a continuation of application No. 10/633,698, filed on Aug. 5, 2003, now abandoned, which is a continuation-in-part of application No. 09/763,669, filed as application No. PCT/GB99/02806 on Aug. 25, 1999, now Pat. No. 6,632,440.

(30) Foreign Application Priority Data

Aug. 25, 1998 (GB) .................................. 9818548.1

(51) Int. Cl.

*C07K 14/00* (2006.01)
*A61K 38/00* (2006.01)
*C12P 21/00* (2006.01)
*C07H 21/04* (2006.01)

(52) U.S. Cl.

USPC ........ 435/69.7; 435/69.1; 435/212; 514/21.2; 530/350; 536/23.7

(58) Field of Classification Search

USPC ......... 424/239.1, 434, 282.1, 9.1, 236.1, 810; 514/2, 12, 21.2; 530/350; 435/7.1, 6, 435/69.1, 325, 368, 371, 69.7, 212; 536/23.7

See application file for complete search history.

(56) References Cited

U.S. PATENT DOCUMENTS 4,873,346 A 10/1989 Anderson
5,766,605 A 6/1998 Sanders et al.
5,989,545 A * 11/1999 Foster et al. ............... 424/183.1
6,395,513 B1 5/2002 Foster et al.
6,461,617 B1 10/2002 Shone et al.
6,632,440 B1 10/2003 Quinn et al.
7,132,259 B1 * 11/2006 Dolly et al. .................. 435/69.1
7,192,596 B2 * 3/2007 Shone et al. ............... 424/247.1
7,709,228 B2 * 5/2010 Dolly et al. .................. 435/69.7
8,614,069 B2 * 12/2013 Cossins et al. ............... 435/69.7
2003/0049264 A1 3/2003 Foster et al.
2003/0147895 A1 8/2003 Shone et al.
2003/0166238 A1 9/2003 Shone et al.

FOREIGN PATENT DOCUMENTS

EP 0 673 938 A2 9/1995
WO 95/17904 7/1995
WO 95/28171 10/1995
WO 95/33850 12/1995
WO 96/33273 10/1996
WO 97/13410 4/1997
WO 98/07864 2/1998

OTHER PUBLICATIONS

Fisher, C.E., et al., "Genetic construction and properties of a diptheria toxin-related substance P fusion protein: In vitro destruction of cells bearing substance P receptors," Proc. Natl. Acad. Sci. USA 93:7341-7345, National Academy of Sciences USA (1996).
Hambleton, P., "*Clostridium botulinum* toxins: a general review of involvement in disease, structure, mode of action and preparation for clinical use," J. Neurol. 239:16-20, Springer-Verlag (1992).
Kurazono, H., et al., "Minimal essential domains specifying toxicity of the light chains of tetanus toxin and botulinum neurotoxin Type A," J. Biol. Chem. 267: 14721-14729, American Society for Biochemistry and Molecular Biology, Inc. (1992).
Nishiki, T., et al., "Identification of protein receptor for *Clostridium botulinum* Type B neurotoxin in rat brain synaptosomes," J. Biol. Chem. 269:10498-10503, American Society for Biochemistry and Molecular Biology, Inc. (1994).
Nishiki, T., et al., "The high-affinity binding of *Clostridium botulinum* type B neurotoxin to synaptotagmin II associated with gangliosides $G_{rib}/G_{pla}$, " FEBS Lett. 378:253-257, Federation of European Biochemical Societies (1996).
Poulain, B., et al., "Inhibition of transmitter release by botulinum neurotoxin A. Contributions of various fragments to the intoxication process," Eur. J. Biochem. 185:197-203, Federation of European Biochemical Societies (1989).
Zhou, L., et al., "Expression and purification of the light chain of botulinum neurotoxin A: A single mutation abolishes its cleavage of SNAP-25 and neurotoxicity after reconstitution with the heavy chain," Biochemistry 34: 15175-15181, American Chemical Society (1995).
International Search Report for PCT/GB99/02806, mailed Mar. 16, 2000.
Application and prosecution history for "Recombinant Toxin-Fragments," Shone et al., U.S. Appl. No. 09/255,829, filed Feb. 23, 1999.
Application and prosecution history for "Conjugates of Galatose-Binding Lectins and Clostridial Neurotoxins and Analgesics," Duggan et al., U.S. Appl. No. 09/529,130, with a §371 date of Jun. 22, 2000.
Application and prosecution history for "Methods and Compounds for the Treatment of Mucus Hypersecretion," Quinn et al., U.S. Appl. No. 09/763,669, with a §371 date of May 29, 2001.

(Continued)

*Primary Examiner* — Chih-Min Kam

(74) *Attorney, Agent, or Firm* — Morris, Manning & Martin, LLP; Christopher W. Raimund

(57) ABSTRACT

The present invention relates to treatment of mucus hypersecretion, to compositions therefore and manufacture of those compositions. The present invention relates particularly, though not exclusively, to the treatment of chronic bronchitis in chronic obstructive pulmonary disease (COPD), asthma and other clinical conditions involving COPD.

14 Claims, 25 Drawing Sheets

(56) References Cited

OTHER PUBLICATIONS

Application and prosecution history for "Delivery of Superoxide Dismutase to Neuronal Cells," Shone et al., U.S. Appl. No. 09/831,050, with a §371 date of Aug. 20, 2001.

Application and prosecution history for "Constructs for Delivery of Therapeutic Agents to Neuronal Cells," Shone et al., U.S. Appl. No. 10/130,973, with a §371 date of Jun. 25, 2002.

Application and prosecution history for "Recombinant Toxin Fragments," Shone et al., U.S. Appl. No. 10/241,596, filed Sep. 12, 2002.

Shone et al., "Delivery of superoxide dismutase to neuronal cells," U.S. Appl. No. 11/062,471, filed Feb. 22, 2005.

Shone et al., "Recombinant toxin fragments," U.S. Appl. No. 11/077,550, filed Mar. 11, 2005.

Shone et al., "Recombinant toxin fragments," U.S. Appl. No. 10/527,411, filed Mar. 11, 2005.

* cited by examiner

SEQUENCE LISTING

```
<160> NUMBER OF SEQ ID NOS: 44

<210> SEQ ID NO 1
<211> LENGTH: 2631
<212> TYPE: DNA
<213> ORGANISM: Unknown
<220> FEATURE:
<223> OTHER INFORMATION: DNA sequence of LHN/B

<400> SEQUENCE: 1
```

-continued

```
ggatccatgc cggttaccat caacaacttc aactacaacg acccgatcga caacaacaac     60
atcattatga tggaaccgcc gttcgcacgt ggtaccggac gttactacaa ggcttttaag    120
atcaccgacc gtatctggat catcccggaa cgttacacct tcggttacaa acctgaggac    180
ttcaacaaga gtagcgggat tttcaatcgt gacgtctgcg agtactatga tccagattat    240
ctgaatacca acgataagaa gaacatattc cttcagacta tgattaaact cttcaaccgt    300
atcaaaagca aaccgctcgg tgaaaaactc ctcgaaatga ttatcaacgg tatcccgtac    360
ctcggtgacc gtcgtgtccc gcttgaagag ttcaacacca acatcgcaag cgtcaccgtc    420
aacaaactca tcagcaaccc aggtgaagtc gaacgtaaaa aaggtatctt cgcaaacctc    480
atcatcttcg gtccgggtcc ggtcctcaac gaaaacgaaa ccatcgacat cggtatccag    540
aaccacttcg caagccgtga aggtttcggt ggtatcatgc agatgaaatt ctgcccggaa    600
tacgtcagtg tcttcaacaa cgtccaggaa aacaaaggtg caagcatctt caaccgtcgt    660
ggttacttca gcgacccggc actcatcctc atgcatgaac tcatccacgt cctccacggt    720
ctctacggta tcaaagttga cgacctcccg atcgtcccga acgagaagaa attcttcatg    780
cagagcaccg acgcaatcca ggctgaggaa ctctacacct tcggtggcca agacccaagt    840
atcataaccc cgtccaccga caaaagcatc tacgacaaag tcctccagaa cttcaggggt    900
atcgtggaca gactcaacaa agtcctcgtc tgcatcagcg acccgaacat caatatcaac    960
atatacaaga acaagttcaa agacaagtac aaattcgtcg aggacagcga aggcaaatac   1020
agcatcgacg tagaaagttt cgacaagctc tacaaaagcc tcatgttcgg tttcaccgaa   1080
accaacatcg ccgagaacta caagatcaag acaagggcaa gttacttcag cgacagcctc   1140
ccgcctgtca aaatcaagaa cctcttagac aacgagattt acacaattga agagggcttc   1200
aacatcagtg acaaagacat ggagaaggaa tacagaggtc agaacaaggc tatcaacaaa   1260
caggcatacg aggagatcag caaagaacac ctcgcagtct acaagatcca gatgtgcgtc   1320
gacgaagaaa agctgtacga cgacgacgac aaagaccgtt ggggttcttc gctgcagtgc   1380
atcgacgttg acaacgaaga cctgttcttc atcgctgaca aaaacagctt cagtgacgac   1440
ctgagcaaaa acgaacgtat cgaatacaac acccagagca actacatcga aaacgacttc   1500
ccgatcaacg aactgatcct ggacaccgac ctgataagta aaatcgaact gccgagcgaa   1560
aacaccgaaa gtctgaccga cttcaacgtt gacgttccgg tttacgaaaa acagccggct   1620
atcaagaaaa tcttcaccga cgaaaacacc atcttccagt acctgtacag ccagaccttc   1680
ccgctggaca tccgtgacat cagtctgacc agcagtttcg acgacgctct gctgttcagc   1740
aacaaagttt acagtttctt cagcatggac tacatcaaaa ccgctaacaa agttgttgaa   1800
gcagggctgt tcgctggttg ggttaaacag atcgttaacg acttcgttat cgaagctaac   1860
aaaagcaaca ctatggacaa aatcgctgac atcagtctga tcgttccgta catcggtctg   1920
gctctgaacg ttggtaacga aaccgctaaa ggtaactttg aaaacgcttt cgagatcgct   1980
ggtgcaagca tcctgctgga gttcatcccg gaactgctga tcccggttgt tggtgctttc   2040
ctgctggaaa gttacatcga caacaaaaac aagatcatca aaaccatcga caacgctctg   2100
accaaacgta acgaaaaatg gagtgatatg tacggtctga tcgttgctca gtggctgagc   2160
accgtcaaca cccagttcta caccatcaaa gaaggtatgt acaaagctct gaactaccag   2220
gctcaggctc tggaagagat catcaaatac cgttacaaca tctacagtga gaaggaaaag   2280
agtaacatca acatcgactt caacgacatc aacagcaaac tgaacgaagg tatcaaccag   2340
gctatcgaca acatcaacaa cttcatcaac ggttgcagtg ttagctacct gatgaagaag   2400
```

```
atgatcccgc tggctgttga aaaactgctg gacttcgaca acaccctgaa aaagaacctg   2460

ctgaactaca tcgacgaaaa caagctgtac ctgatcggta gtgctgaata cgaaaaaagt   2520

aaagtgaaca aatacctgaa gaccatcatg ccgttcgacc tgagtatcta caccaacgac   2580

accatcctga tcgaaatgtt caacaaatac aactctctag actagaagct t            2631
```

<210> SEQ ID NO 2
<211> LENGTH: 2620
<212> TYPE: DNA
<213> ORGANISM: Unknown
<220> FEATURE:
<223> OTHER INFORMATION: DNA sequence of LHN/C

<400> SEQUENCE: 2

```
ggatccatgc cgatcaccat caacaacttc aactacagcg atccggtgga taacaaaaac     60

atcctgtacc tggataccca tctgaatacc ctggcgaacg aaccggaaaa agcgtttcgt    120

atcaccggca acatttgggt tattccggat cgttttagcc gtaacagcaa cccgaatctg    180

aataaaccgc cgcgtgttac cagcccgaaa agcggttatt acgatccgaa ctatctgagc    240

accgatagcg ataaagatac cttcctgaaa gaaatcatca aactgttcaa acgcatcaac    300

agccgtgaaa ttggcgaaga actgatctat cgcctgagca ccgatattcc gtttccgggc    360

aacaacaaca ccccgatcaa cacctttgat ttcgatgtgg atttcaacag cgttgatgtt    420

aaaacccgcc agggtaacaa ttgggtgaaa accggcagca ttaacccaag cgtgattatt    480

accggtccgc gcgaaaacat tattgatccg gaaaccagca cctttaaact gaccaacaac    540

acctttgcgg cgcaggaagg ttttggcgcg ctgagcatta ttagcattag cccgcgcttt    600

atgctgacct atagcaacgc gaccaacgat gttggtgaag gccgtttcag caaaagcgaa    660

ttttgcatgg acccgatcct gatcctgatg catgaactga accatgcgat gcataacctg    720

tatggcatcg cgattccgaa cgatcagacc attagcagcg tgaccagcaa catcttttac    780

agccagtaca acgtgaaact ggaatatgcg gaaatctatg cgtttggcgg tccgaccatt    840

gatctgattc cgaaaagcgc gcgcaaatac ttcgaagaaa aagcgctgga ttactatcgc    900

agcattgcga aacgtctgaa cagcattacc accgcgaatc cgagcagctt caacaaatat    960

atcggcgaat ataaacagaa actgatccgc aaatatcgct ttgtggtgga aagcagcggc   1020

gaagttaccg ttaaccgcaa taaattcgtg gaactgtaca acgaactgac ccagatcttc   1080

accgaattta actatgcgaa aatctataac gtgcagaacc gtaaaatcta cctgagcaac   1140

gtgtataccc cggtgaccgc gaatattctg gatgataacg tgtacgatat ccagaacggc   1200

tttaacatcc cgaaaagcaa cctgaacgtt ctgtttatgg gccagaacct gagccgtaat   1260

ccggcgctgc gtaaagtgaa cccggaaaac atgctgtacc tgttcaccaa attttgcgtc   1320

gacgcgattg atggtcgtag cctgtacaac aaaaccctgc agtgtcgtga actgctggtg   1380

aaaaacaccg atctgccgtt tattggcgat atcagcgatg tgaaaaccga tatcttcctg   1440

cgcaaagata tcaacgaaga aaccgaagtg atctactacc cggataacgt gagcgttgat   1500

caggtgatcc tgagcaaaaa caccagcgaa catggtcagc tggatctgct gtatccgagc   1560

attgatagcg aaagcgaaat tctgccgggc gaaaaccagg tgttttacga taaccgtacc   1620

cagaacgtgg attacctgaa cagctattac tacctggaaa gccagaaact gagcgataac   1680

gtggaagatt ttacctttac ccgcagcatt gaagaagcgc tggataacag cgcgaaagtt   1740

tacacctatt ttccgaccct ggcgaacaaa gttaatgcgg gtgttcaggg cggtctgttt   1800
```

```
ctgatgtggg cgaacgatgt ggtggaagat ttcaccacca acatcctgcg taaagatacc   1860

ctggataaaa tcagcgatgt tagcgcgatt attccgtata ttggtccggc gctgaacatt   1920

agcaatagcg tgcgtcgtgg caattttacc gaagcgtttg cggttaccgg tgtgaccatt   1980

ctgctggaag cgtttccgga atttaccatt ccggcgctgg gtgcgtttgt gatctatagc   2040

aaagtgcagg aacgcaacga aatcatcaaa accatcgata actgcctgga acagcgtatt   2100

aaacgctgga aagatagcta tgaatggatg atgggcacct ggctgagccg tattatcacc   2160

cagttcaaca acatcagcta ccagatgtac gatagcctga actatcaggc gggtgcgatt   2220

aaagcgaaaa tcgatctgga atacaaaaaa tacagcggca gcgataaaga aaacatcaaa   2280

agccaggttg aaaacctgaa aaacagcctg gatgtgaaaa ttagcgaagc gatgaataac   2340

atcaacaaat tcatccgcga atgcagcgtg acctacctgt tcaaaaacat gctgccgaaa   2400

gtgatcgatg aactgaacga atttgatcgc aacaccaaag cgaaactgat caacctgatc   2460

gatagccaca acattattct ggtgggcgaa gtggataaac tgaaagcgaa agttaacaac   2520

agcttccaga acaccatccc gtttaacatc ttcagctata ccaacaacag cctgctgaaa   2580

gatatcatca acgaatactt caatctagac taataagctt                         2620
```

<210> SEQ ID NO 3
<211> LENGTH: 249
<212> TYPE: DNA
<213> ORGANISM: Unknown
<220> FEATURE:
<223> OTHER INFORMATION: DNA sequence of EGF linker

<400> SEQUENCE: 3

```
ggatccgtcg acctgcaggg tctagaaggc ggtggcggta gcggcggtgg cggtagcggc     60

ggtggcggta gcgcactaga caactctgac tctgaatgcc cgctgtctca cgacggttac    120

tgcctgcacg acggtgtttg catgtacatc gaagctctgg acaaatacgc ttgcaactgc    180

gttgttggtt acatcggtga acgttgccag taccgtgacc tgaaatggtg ggaactgcgt    240

tgaaagctt                                                            249
```

<210> SEQ ID NO 4
<211> LENGTH: 2838
<212> TYPE: DNA
<213> ORGANISM: Unknown
<220> FEATURE:
<223> OTHER INFORMATION: DNA sequence of EGF-C fusion

<400> SEQUENCE: 4

```
ggatccgaat tcatgccgat caccatcaac aacttcaact acagcgatcc ggtggataac     60

aaaaacatcc tgtacctgga tacccatctg aataccctgg cgaacgaacc ggaaaaagcg    120

tttcgtatca ccggcaacat ttgggttatt ccggatcgtt ttagccgtaa cagcaacccg    180

aatctgaata aaccgccgcg tgttaccagc ccgaaaagcg gttattacga tccgaactat    240

ctgagcaccg atagcgataa agataccttc ctgaaagaaa tcatcaaact gttcaaacgc    300

atcaacagcc gtgaaattgg cgaagaactg atctatcgcc tgagcaccga tattccgttt    360

ccgggcaaca acaacacccc gatcaacacc tttgatttcg atgtggattt caacagcgtt    420

gatgttaaaa cccgccaggg taacaattgg gtgaaaaccg gcagcattaa cccgagcgtg    480

attattaccg gtccgcgcga aaacattatt gatccggaaa ccagcacctt taaactgacc    540

aacaacacct ttgcggcgca ggaaggtttt ggcgcgctga gcattattag cattagcccg    600

cgctttatgc tgacctatag caacgcgacc aacgatgttg gtgaaggccg tttcagcaaa    660
```

-continued agcgaatttt gcatggaccc gatcctgatc ctgatgcatg aactgaacca tgcgatgcat 720
aacctgtatg gcatcgcgat tccgaacgat cagaccatta gcagcgtgac cagcaacatc 780
ttttacagcc agtacaacgt gaaactggaa tatgcggaaa tctatgcgtt tggcggtccg 840
accattgatc tgattccgaa aagcgcgcgc aaatacttcg aagaaaaagc gctggattac 900
tatcgcagca ttgcgaaacg tctgaacagc attaccaccg cgaatccgag cagcttcaac 960
aaatatatcg gcgaatataa acagaaactg atccgcaaat atcgctttgt ggtggaaagc 1020
agcggcgaag ttaccgttaa ccgcaataaa ttcgtggaac tgtacaacga actgacccag 1080
atcttcaccg aatttaacta tgcgaaaatc tataacgtgc agaaccgtaa aatctacctg 1140
agcaacgtgt ataccccggt gaccgcgaat attctggatg ataacgtgta cgatatccag 1200
aacggcttta acatcccgaa aagcaacctg aacgttctgt ttatgggcca gaacctgagc 1260
cgtaatccgg cgctgcgtaa agtgaacccg gaaaacatgc tgtacctgtt caccaaattt 1320
tgcgtcgacg cgattgatgg tcgtagcctg tacaacaaaa ccctgcagtg tcgtgaactg 1380
ctggtgaaaa acaccgatct gccgtttatt ggcgatatca gcgatgtgaa aaccgatatc 1440
ttcctgcgca aagatatcaa cgaagaaacc gaagtgatct actacccgga taacgtgagc 1500
gttgatcagg tgatcctgag caaaaacacc agcgaacatg gtcagctgga tctgctgtat 1560
ccgagcattg atagcgaaag cgaaattctg ccgggcgaaa accaggtgtt ttacgataac 1620
cgtacccaga acgtggatta cctgaacagc tattactacc tggaaagcca gaaactgagc 1680
gataacgtgg aagattttac ctttacccgc agcattgaag aagcgctgga taacagcgcg 1740
aaagtttaca cctattttcc gaccctggcg aacaaagtta atgcgggtgt tcagggcggt 1800
ctgtttctga tgtgggcgaa cgatgtggtg gaagatttca ccaccaacat cctgcgtaaa 1860
gataccctgg ataaaatcag cgatgttagc gcgattattc cgtatattgg tccggcgctg 1920
aacattagca atagcgtgcg tcgtggcaat tttaccgaag cgtttgcggt taccggtgtg 1980
accattctgc tggaagcgtt tccggaattt accattccgg cgctgggtgc gtttgtgatc 2040
tatagcaaag tgcaggaacg caacgaaatc atcaaaacca tcgataactg cctggaacag 2100
cgtattaaac gctggaaaga tagctatgaa tggatgatgg gcacctggct gagccgtatt 2160
atcacccagt tcaacaacat cagctaccag atgtacgata gcctgaacta tcaggcgggt 2220
gcgattaaag cgaaaatcga tctggaatac aaaaaataca gcggcagcga taaagaaaac 2280
atcaaaagcc aggttgaaaa cctgaaaaac agcctggatg tgaaaattag cgaagcgatg 2340
aataacatca acaaattcat ccgcgaatgc agcgtgacct acctgttcaa aaacatgctg 2400
ccgaaagtga tcgatgaact gaacgaattt gatcgcaaca ccaaagcgaa actgatcaac 2460
ctgatcgata gccacaacat tattctggtg ggcgaagtgg ataaactgaa agcgaaagtt 2520
aacaacagct tccagaacac catcccgttt aacatcttca gctataccaa caacagcctg 2580
ctgaaagata tcatcaacga atacttcaat ctagaaggtg gcggtgggtc cggtggcggt 2640
ggctcaggcg gggcggtag cgcactagac aactctgact ctgaatgccc gctgtctcac 2700
gacggttact gcctgcacga cggtgtttgc atgtacatcg aagctctgga caaatacgct 2760
tgcaactgcg ttgttggtta catcggtgaa cgttgccagt accgtgacct gaaatggtgg 2820
gaactgcgtt gaaagctt 2838

<210> SEQ ID NO 5
<211> LENGTH: 945
<212> TYPE: PRT

<213> ORGANISM: Unknown
<220> FEATURE:
<223> OTHER INFORMATION: Protein sequence of the EGF-C fusion

<400> SEQUENCE: 5

Gly Ser Glu Phe Met Pro Ile Thr Ile Asn Asn Phe Asn Tyr Ser Asp
1               5                   10                  15

Pro Val Asp Asn Lys Asn Ile Leu Tyr Leu Asp Thr His Leu Asn Thr
            20                  25                  30

Leu Ala Asn Glu Pro Glu Lys Ala Phe Arg Ile Thr Gly Asn Ile Trp
        35                  40                  45

Val Ile Pro Asp Arg Phe Ser Arg Asn Ser Asn Pro Asn Leu Asn Lys
    50                  55                  60

Pro Pro Arg Val Thr Ser Pro Lys Ser Gly Tyr Tyr Asp Pro Asn Tyr
65                  70                  75                  80

Leu Ser Thr Asp Ser Asp Lys Asp Thr Phe Leu Lys Glu Ile Ile Lys
                85                  90                  95

Leu Phe Lys Arg Ile Asn Ser Arg Glu Ile Gly Glu Glu Leu Ile Tyr
            100                 105                 110

Arg Leu Ser Thr Asp Ile Pro Phe Pro Gly Asn Asn Asn Thr Pro Ile
        115                 120                 125

Asn Thr Phe Asp Phe Asp Val Asp Phe Asn Ser Val Asp Val Lys Thr
    130                 135                 140

Arg Gln Gly Asn Asn Trp Val Lys Thr Gly Ser Ile Asn Pro Ser Val
145                 150                 155                 160

Ile Ile Thr Gly Pro Arg Glu Asn Ile Ile Asp Pro Glu Thr Ser Thr
                165                 170                 175

Phe Lys Leu Thr Asn Asn Thr Phe Ala Ala Gln Glu Gly Phe Gly Ala
            180                 185                 190

Leu Ser Ile Ile Ser Ile Ser Pro Arg Phe Met Leu Thr Tyr Ser Asn
        195                 200                 205

Ala Thr Asn Asp Val Gly Glu Gly Arg Phe Ser Lys Ser Glu Phe Cys
    210                 215                 220

Met Asp Pro Ile Leu Ile Leu Met His Glu Leu Asn His Ala Met His
225                 230                 235                 240

Asn Leu Tyr Gly Ile Ala Ile Pro Asn Asp Gln Thr Ile Ser Ser Val
                245                 250                 255

Thr Ser Asn Ile Phe Tyr Ser Gln Tyr Asn Val Lys Leu Glu Tyr Ala
            260                 265                 270

Glu Ile Tyr Ala Phe Gly Gly Pro Thr Ile Asp Leu Ile Pro Lys Ser
        275                 280                 285

Ala Arg Lys Tyr Phe Glu Glu Lys Ala Leu Asp Tyr Tyr Arg Ser Ile
    290                 295                 300

Ala Lys Arg Leu Asn Ser Ile Thr Thr Ala Asn Pro Ser Ser Phe Asn
305                 310                 315                 320

Lys Tyr Ile Gly Glu Tyr Lys Gln Lys Leu Ile Arg Lys Tyr Arg Phe
                325                 330                 335

Val Val Glu Ser Ser Gly Glu Val Thr Val Asn Arg Asn Lys Phe Val
            340                 345                 350

Glu Leu Tyr Asn Glu Leu Thr Gln Ile Phe Thr Glu Phe Asn Tyr Ala
        355                 360                 365

Lys Ile Tyr Asn Val Gln Asn Arg Lys Ile Tyr Leu Ser Asn Val Tyr
    370                 375                 380

Thr Pro Val Thr Ala Asn Ile Leu Asp Asp Asn Val Tyr Asp Ile Gln

-continued

```
385                 390                 395                 400

Asn Gly Phe Asn Ile Pro Lys Ser Asn Leu Asn Val Leu Phe Met Gly
                405                 410                 415

Gln Asn Leu Ser Arg Asn Pro Ala Leu Arg Lys Val Asn Pro Glu Asn
            420                 425                 430

Met Leu Tyr Leu Phe Thr Lys Phe Cys Val Asp Ala Ile Asp Gly Arg
        435                 440                 445

Ser Leu Tyr Asn Lys Thr Leu Gln Cys Arg Glu Leu Leu Val Lys Asn
    450                 455                 460

Thr Asp Leu Pro Phe Ile Gly Asp Ile Ser Asp Val Lys Thr Asp Ile
465                 470                 475                 480

Phe Leu Arg Lys Asp Ile Asn Glu Glu Thr Glu Val Ile Tyr Tyr Pro
                485                 490                 495

Asp Asn Val Ser Val Asp Gln Val Ile Leu Ser Lys Asn Thr Ser Glu
            500                 505                 510

His Gly Gln Leu Asp Leu Leu Tyr Pro Ser Ile Asp Ser Glu Ser Glu
        515                 520                 525

Ile Leu Pro Gly Glu Asn Gln Val Phe Tyr Asp Asn Arg Thr Gln Asn
    530                 535                 540

Val Asp Tyr Leu Asn Ser Tyr Tyr Tyr Leu Glu Ser Gln Lys Leu Ser
545                 550                 555                 560

Asp Asn Val Glu Asp Phe Thr Phe Thr Arg Ser Ile Glu Glu Ala Leu
                565                 570                 575

Asp Asn Ser Ala Lys Val Tyr Thr Tyr Phe Pro Thr Leu Ala Asn Lys
            580                 585                 590

Val Asn Ala Gly Val Gln Gly Gly Leu Phe Leu Met Trp Ala Asn Asp
        595                 600                 605

Val Val Glu Asp Phe Thr Thr Asn Ile Leu Arg Lys Asp Thr Leu Asp
    610                 615                 620

Lys Ile Ser Asp Val Ser Ala Ile Ile Pro Tyr Ile Gly Pro Ala Leu
625                 630                 635                 640

Asn Ile Ser Asn Ser Val Arg Arg Gly Asn Phe Thr Glu Ala Phe Ala
                645                 650                 655

Val Thr Gly Val Thr Ile Leu Leu Glu Ala Phe Pro Glu Phe Thr Ile
            660                 665                 670

Pro Ala Leu Gly Ala Phe Val Ile Tyr Ser Lys Val Gln Glu Arg Asn
        675                 680                 685

Glu Ile Ile Lys Thr Ile Asp Asn Cys Leu Glu Gln Arg Ile Lys Arg
    690                 695                 700

Trp Lys Asp Ser Tyr Glu Trp Met Met Gly Thr Trp Leu Ser Arg Ile
705                 710                 715                 720

Ile Thr Gln Phe Asn Asn Ile Ser Tyr Gln Met Tyr Asp Ser Leu Asn
                725                 730                 735

Tyr Gln Ala Gly Ala Ile Lys Ala Lys Ile Asp Leu Glu Tyr Lys Lys
            740                 745                 750

Tyr Ser Gly Ser Asp Lys Glu Asn Ile Lys Ser Gln Val Glu Asn Leu
        755                 760                 765

Lys Asn Ser Leu Asp Val Lys Ile Ser Glu Ala Met Asn Asn Ile Asn
    770                 775                 780

Lys Phe Ile Arg Glu Cys Ser Val Thr Tyr Leu Phe Lys Asn Met Leu
785                 790                 795                 800

Pro Lys Val Ile Asp Glu Leu Asn Glu Phe Asp Arg Asn Thr Lys Ala
                805                 810                 815
```

```
Lys Leu Ile Asn Leu Ile Asp Ser His Asn Ile Ile Leu Val Gly Glu
            820                 825                 830

Val Asp Lys Leu Lys Ala Lys Val Asn Asn Ser Phe Gln Asn Thr Ile
        835                 840                 845

Pro Phe Asn Ile Phe Ser Tyr Thr Asn Asn Ser Leu Leu Lys Asp Ile
    850                 855                 860

Ile Asn Glu Tyr Phe Asn Leu Glu Gly Gly Gly Gly Ser Gly Gly Gly
865                 870                 875                 880

Gly Ser Gly Gly Gly Gly Ser Ala Leu Asp Asn Ser Asp Ser Glu Cys
                885                 890                 895

Pro Leu Ser His Asp Gly Tyr Cys Leu His Asp Gly Val Cys Met Tyr
            900                 905                 910

Ile Glu Ala Leu Asp Lys Tyr Ala Cys Asn Cys Val Val Gly Tyr Ile
        915                 920                 925

Gly Glu Arg Cys Gln Tyr Arg Asp Leu Lys Trp Trp Glu Leu Arg Lys
    930                 935                 940

Leu
945


<210> SEQ ID NO 6
<211> LENGTH: 2850
<212> TYPE: DNA
<213> ORGANISM: Unknown
<220> FEATURE:
<223> OTHER INFORMATION: DNA sequence of the EGF-B fusion

<400> SEQUENCE: 6

ggatccatgc cggttaccat caacaacttc aactacaacg acccgatcga caacaacaac     60

atcattatga tggaaccgcc gttcgcacgt ggtaccggac gttactacaa ggcttttaag    120

atcaccgacc gtatctggat catcccggaa cgttacacct tcggttacaa acctgaggac    180

ttcaacaaga gtagcgggat tttcaatcgt gacgtctgcg agtactatga tccagattat    240

ctgaatacca acgataagaa gaacatattc cttcagacta tgattaaact cttcaaccgt    300

atcaaaagca aaccgctcgg tgaaaaactc ctcgaaatga ttatcaacgg tatcccgtac    360

ctcggtgacc gtcgtgtccc gcttgaagag ttcaacacca acatcgcaag cgtcaccgtc    420

aacaaactca tcagcaaccc aggtgaagtc gaacgtaaaa aaggtatctt cgcaaacctc    480

atcatcttcg gtccgggtcc ggtcctcaac gaaaacgaaa ccatcgacat cggtatccag    540

aaccacttcg caagccgtga aggtttcggt ggtatcatgc agatgaaatt ctgcccggaa    600

tacgtcagtg tcttcaacaa cgtccaggaa aacaaaggtg caagcatctt caaccgtcgt    660

ggttacttca gcgacccggc actcatcctc atgcatgaac tcatccacgt cctccacggt    720

ctctacggta tcaaagttga cgacctcccg atcgtcccga acgagaagaa attcttcatg    780

cagagcaccg acgcaatcca ggctgaggaa ctctacacct tcggtggcca agacccaagt    840

atcataaccc cgtccaccga caaaagcatc tacgacaaag tcctccagaa cttcaggggt    900

atcgtggaca gactcaacaa agtcctcgtc tgcatcagcg acccgaacat caatatcaac    960

atatacaaga acaagttcaa agacaagtac aaattcgtcg aggacagcga aggcaaatac   1020

agcatcgacg tagaaagttt cgacaagctc tacaaaagcc tcatgttcgg tttcaccgaa   1080

accaacatcg ccgagaacta caagatcaag acaagggcaa gttacttcag cgacagcctc   1140

ccgcctgtca aaatcaagaa cctcttagac aacgagattt acacaattga agagggcttc   1200

aacatcagtg acaaagacat ggagaaggaa tacagaggtc agaacaaggc tatcaacaaa   1260
```

-continued caggcatacg aggagatcag caaagaacac ctcgcagtct acaagatcca gatgtgcgtc 1320
gacgaagaaa agctgtacga cgacgacgac aaagaccgtt ggggttcttc gctgcagtgc 1380
atcgacgttg acaacgaaga cctgttcttc atcgctgaca aaaacagctt cagtgacgac 1440
ctgagcaaaa acgaacgtat cgaatacaac acccagagca actacatcga aaacgacttc 1500
ccgatcaacg aactgatcct ggacaccgac ctgataagta aaatcgaact gccgagcgaa 1560
aacaccgaaa gtctgaccga cttcaacgtt gacgttccgg tttacgaaaa acagccggct 1620
atcaagaaaa tcttcaccga cgaaaacacc atcttccagt acctgtacag ccagaccttc 1680
ccgctggaca tccgtgacat cagtctgacc agcagtttcg acgacgctct gctgttcagc 1740
aacaaagttt acagtttctt cagcatggac tacatcaaaa ccgctaacaa agttgttgaa 1800
gcagggctgt tcgctggttg ggttaaacag atcgttaacg acttcgttat cgaagctaac 1860
aaaagcaaca ctatggacaa aatcgctgac atcagtctga tcgttccgta catcggtctg 1920
gctctgaacg ttggtaacga aaccgctaaa ggtaactttg aaaacgcttt cgagatcgct 1980
ggtgcaagca tcctgctgga gttcatcccg gaactgctga tcccggttgt tggtgctttc 2040
ctgctggaaa gttacatcga caacaaaaac aagatcatca aaaccatcga caacgctctg 2100
accaaacgta acgaaaaatg gagtgatatg tacggtctga tcgttgctca gtggctgagc 2160
accgtcaaca cccagttcta caccatcaaa gaaggtatgt acaaagctct gaactaccag 2220
gctcaggctc tggaagagat catcaaatac cgttacaaca tctacagtga gaaggaaaag 2280
agtaacatca acatcgactt caacgacatc aacagcaaac tgaacgaagg tatcaaccag 2340
gctatcgaca acatcaacaa cttcatcaac ggttgcagtg ttagctacct gatgaagaag 2400
atgatcccgc tggctgttga aaaactgctg gacttcgaca acaccctgaa aaagaacctg 2460
ctgaactaca tcgacgaaaa caagctgtac ctgatcggta gtgctgaata cgaaaaaagt 2520
aaagtgaaca aatacctgaa gaccatcatg ccgttcgacc tgagtatcta caccaacgac 2580
accatcctga tcgaaatgtt caacaaatac aactctctag atctagaagg tggcggtggg 2640
tccggtggcg gtggctcagg cgggggcggt agcgcactag acaactctga ctctgaatgc 2700
ccgctgtctc acgacggtta ctgcctgcac gacggtgttt gcatgtacat cgaagctctg 2760
gacaaatacg cttgcaactg cgttgttggt tacatcggtg aacgttgcca gtaccgtgac 2820
ctgaaatggt gggaactgcg ttgaaagctt 2850

<210> SEQ ID NO 7
<211> LENGTH: 949
<212> TYPE: PRT
<213> ORGANISM: Unknown
<220> FEATURE:
<223> OTHER INFORMATION: Protein sequence of the EGF-B fusion

<400> SEQUENCE: 7

Gly Ser Met Pro Val Thr Ile Asn Asn Phe Asn Tyr Asn Asp Pro Ile
1 5 10 15

Asp Asn Asn Asn Ile Ile Met Met Glu Pro Pro Phe Ala Arg Gly Thr
20 25 30

Gly Arg Tyr Tyr Lys Ala Phe Lys Ile Thr Asp Arg Ile Trp Ile Ile
35 40 45

Pro Glu Arg Tyr Thr Phe Gly Tyr Lys Pro Glu Asp Phe Asn Lys Ser
50 55 60

Ser Gly Ile Phe Asn Arg Asp Val Cys Glu Tyr Tyr Asp Pro Asp Tyr
65 70 75 80

```
Leu Asn Thr Asn Asp Lys Lys Asn Ile Phe Leu Gln Thr Met Ile Lys
                85                  90                  95

Leu Phe Asn Arg Ile Lys Ser Lys Pro Leu Gly Glu Lys Leu Leu Glu
            100                 105                 110

Met Ile Ile Asn Gly Ile Pro Tyr Leu Gly Asp Arg Arg Val Pro Leu
        115                 120                 125

Glu Glu Phe Asn Thr Asn Ile Ala Ser Val Thr Val Asn Lys Leu Ile
    130                 135                 140

Ser Asn Pro Gly Glu Val Glu Arg Lys Lys Gly Ile Phe Ala Asn Leu
145                 150                 155                 160

Ile Ile Phe Gly Pro Gly Pro Val Leu Asn Glu Asn Glu Thr Ile Asp
                165                 170                 175

Ile Gly Ile Gln Asn His Phe Ala Ser Arg Glu Gly Phe Gly Gly Ile
            180                 185                 190

Met Gln Met Lys Phe Cys Pro Glu Tyr Val Ser Val Phe Asn Asn Val
        195                 200                 205

Gln Glu Asn Lys Gly Ala Ser Ile Phe Asn Arg Arg Gly Tyr Phe Ser
    210                 215                 220

Asp Pro Ala Leu Ile Leu Met His Glu Leu Ile His Val Leu His Gly
225                 230                 235                 240

Leu Tyr Gly Ile Lys Val Asp Asp Leu Pro Ile Val Pro Asn Glu Lys
                245                 250                 255

Lys Phe Phe Met Gln Ser Thr Asp Ala Ile Gln Ala Glu Glu Leu Tyr
            260                 265                 270

Thr Phe Gly Gly Gln Asp Pro Ser Ile Ile Thr Pro Ser Thr Asp Lys
        275                 280                 285

Ser Ile Tyr Asp Lys Val Leu Gln Asn Phe Arg Gly Ile Val Asp Arg
    290                 295                 300

Leu Asn Lys Val Leu Val Cys Ile Ser Asp Pro Asn Ile Asn Ile Asn
305                 310                 315                 320

Ile Tyr Lys Asn Lys Phe Lys Asp Lys Tyr Lys Phe Val Glu Asp Ser
                325                 330                 335

Glu Gly Lys Tyr Ser Ile Asp Val Glu Ser Phe Asp Lys Leu Tyr Lys
            340                 345                 350

Ser Leu Met Phe Gly Phe Thr Glu Thr Asn Ile Ala Glu Asn Tyr Lys
        355                 360                 365

Ile Lys Thr Arg Ala Ser Tyr Phe Ser Asp Ser Leu Pro Pro Val Lys
    370                 375                 380

Ile Lys Asn Leu Leu Asp Asn Glu Ile Tyr Thr Ile Glu Glu Gly Phe
385                 390                 395                 400

Asn Ile Ser Asp Lys Asp Met Glu Lys Glu Tyr Arg Gly Gln Asn Lys
                405                 410                 415

Ala Ile Asn Lys Gln Ala Tyr Glu Glu Ile Ser Lys Glu His Leu Ala
            420                 425                 430

Val Tyr Lys Ile Gln Met Cys Val Asp Glu Glu Lys Leu Tyr Asp Asp
        435                 440                 445

Asp Asp Lys Asp Arg Trp Gly Ser Ser Leu Gln Cys Ile Asp Val Asp
    450                 455                 460

Asn Glu Asp Leu Phe Phe Ile Ala Asp Lys Asn Ser Phe Ser Asp Asp
465                 470                 475                 480

Leu Ser Lys Asn Glu Arg Ile Glu Tyr Asn Thr Gln Ser Asn Tyr Ile
                485                 490                 495
```

-continued

```
Glu Asn Asp Phe Pro Ile Asn Glu Leu Ile Leu Asp Thr Asp Leu Ile
            500                 505                 510

Ser Lys Ile Glu Leu Pro Ser Glu Asn Thr Glu Ser Leu Thr Asp Phe
        515                 520                 525

Asn Val Asp Val Pro Val Tyr Glu Lys Gln Pro Ala Ile Lys Lys Ile
    530                 535                 540

Phe Thr Asp Glu Asn Thr Ile Phe Gln Tyr Leu Tyr Ser Gln Thr Phe
545                 550                 555                 560

Pro Leu Asp Ile Arg Asp Ile Ser Leu Thr Ser Ser Phe Asp Asp Ala
                565                 570                 575

Leu Leu Phe Ser Asn Lys Val Tyr Ser Phe Phe Ser Met Asp Tyr Ile
            580                 585                 590

Lys Thr Ala Asn Lys Val Val Glu Ala Gly Leu Phe Ala Gly Trp Val
        595                 600                 605

Lys Gln Ile Val Asn Asp Phe Val Ile Glu Ala Asn Lys Ser Asn Thr
    610                 615                 620

Met Asp Lys Ile Ala Asp Ile Ser Leu Ile Val Pro Tyr Ile Gly Leu
625                 630                 635                 640

Ala Leu Asn Val Gly Asn Glu Thr Ala Lys Gly Asn Phe Glu Asn Ala
                645                 650                 655

Phe Glu Ile Ala Gly Ala Ser Ile Leu Leu Glu Phe Ile Pro Glu Leu
            660                 665                 670

Leu Ile Pro Val Val Gly Ala Phe Leu Leu Glu Ser Tyr Ile Asp Asn
        675                 680                 685

Lys Asn Lys Ile Ile Lys Thr Ile Asp Asn Ala Leu Thr Lys Arg Asn
    690                 695                 700

Glu Lys Trp Ser Asp Met Tyr Gly Leu Ile Val Ala Gln Trp Leu Ser
705                 710                 715                 720

Thr Val Asn Thr Gln Phe Tyr Thr Ile Lys Glu Gly Met Tyr Lys Ala
                725                 730                 735

Leu Asn Tyr Gln Ala Gln Ala Leu Glu Glu Ile Ile Lys Tyr Arg Tyr
            740                 745                 750

Asn Ile Tyr Ser Glu Lys Glu Lys Ser Asn Ile Asn Ile Asp Phe Asn
        755                 760                 765

Asp Ile Asn Ser Lys Leu Asn Glu Gly Ile Asn Gln Ala Ile Asp Asn
    770                 775                 780

Ile Asn Asn Phe Ile Asn Gly Cys Ser Val Ser Tyr Leu Met Lys Lys
785                 790                 795                 800

Met Ile Pro Leu Ala Val Glu Lys Leu Leu Asp Phe Asp Asn Thr Leu
                805                 810                 815

Lys Lys Asn Leu Leu Asn Tyr Ile Asp Glu Asn Lys Leu Tyr Leu Ile
            820                 825                 830

Gly Ser Ala Glu Tyr Glu Lys Ser Lys Val Asn Lys Tyr Leu Lys Thr
        835                 840                 845

Ile Met Pro Phe Asp Leu Ser Ile Tyr Thr Asn Asp Thr Ile Leu Ile
    850                 855                 860

Glu Met Phe Asn Lys Tyr Asn Ser Leu Asp Leu Glu Gly Gly Gly Gly
865                 870                 875                 880

Ser Gly Gly Gly Gly Ser Gly Gly Gly Gly Ser Ala Leu Asp Asn Ser
                885                 890                 895

Asp Ser Glu Cys Pro Leu Ser His Asp Gly Tyr Cys Leu His Asp Gly
            900                 905                 910

Val Cys Met Tyr Ile Glu Ala Leu Asp Lys Tyr Ala Cys Asn Cys Val
```

-continued

```
        915                 920                 925

Val Gly Tyr Ile Gly Glu Arg Cys Gln Tyr Arg Asp Leu Lys Trp Trp
    930                 935                 940

Glu Leu Arg Lys Leu
945


<210> SEQ ID NO 8
<211> LENGTH: 120
<212> TYPE: DNA
<213> ORGANISM: Unknown
<220> FEATURE:
<223> OTHER INFORMATION: DNA sequence of the RGD linker

<400> SEQUENCE: 8

ggatccgtcg acctgcaggg tctagaaggc ggtggcggta gcggcggtgg cggtagcggc     60

ggtggcggta gcgcactagt gggtggtcgt ggtgacatgt tcggtgcttg ataaaagctt    120


<210> SEQ ID NO 9
<211> LENGTH: 2709
<212> TYPE: DNA
<213> ORGANISM: Unknown
<220> FEATURE:
<223> OTHER INFORMATION: DNA sequence of the RGD-C fusion

<400> SEQUENCE: 9

ggatccgaat tcatgccgat caccatcaac aacttcaact acagcgatcc ggtggataac     60

aaaaacatcc tgtacctgga tacccatctg aataccctgg cgaacgaacc ggaaaaagcg    120

tttcgtatca ccggcaacat ttgggttatt ccggatcgtt ttagccgtaa cagcaacccg    180

aatctgaata aaccgccgcg tgttaccagc ccgaaaagcg gttattacga tccgaactat    240

ctgagcaccg atagcgataa agataccttc ctgaaagaaa tcatcaaact gttcaaacgc    300

atcaacagcc gtgaaattgg cgaagaactg atctatcgcc tgagcaccga tattccgttt    360

ccgggcaaca acaacacccc gatcaacacc tttgatttcg atgtggattt caacagcgtt    420

gatgttaaaa cccgccaggg taacaattgg gtgaaaaccg gcagcattaa cccgagcgtg    480

attattaccg gtccgcgcga aaacattatt gatccggaaa ccagcacctt taaactgacc    540

aacaacacct ttgcggcgca ggaaggtttt ggcgcgctga gcattattag cattagcccg    600

cgctttatgc tgacctatag caacgcgacc aacgatgttg gtgaaggccg tttcagcaaa    660

agcgaatttt gcatggaccc gatcctgatc ctgatgcatg aactgaacca tgcgatgcat    720

aacctgtatg gcatcgcgat tccgaacgat cagaccatta gcagcgtgac cagcaacatc    780

ttttacagcc agtacaacgt gaaactggaa tatgcggaaa tctatgcgtt tggcggtccg    840

accattgatc tgattccgaa aagcgcgcgc aaatacttcg aagaaaaagc gctggattac    900

tatcgcagca ttgcgaaacg tctgaacagc attaccaccg cgaatccgag cagcttcaac    960

aaatatatcg gcgaatataa acagaaactg atccgcaaat atcgctttgt ggtggaaagc   1020

agcggcgaag ttaccgttaa ccgcaataaa ttcgtggaac tgtacaacga actgacccag   1080

atcttcaccg aatttaacta tgcgaaaatc tataacgtgc agaaccgtaa aatctacctg   1140

agcaacgtgt ataccccggt gaccgcgaat attctggatg ataacgtgta cgatatccag   1200

aacggcttta acatcccgaa aagcaacctg aacgttctgt ttatgggcca gaacctgagc   1260

cgtaatccgg cgctgcgtaa agtgaacccg gaaaacatgc tgtacctgtt caccaaattt   1320

tgcgtcgacg cgattgatgg tcgtagcctg tacaacaaaa ccctgcagtg tcgtgaactg   1380

ctggtgaaaa acaccgatct gccgtttatt ggcgatatca gcgatgtgaa aaccgatatc   1440
```

```
ttcctgcgca aagatatcaa cgaagaaacc gaagtgatct actacccgga taacgtgagc   1500

gttgatcagg tgatcctgag caaaaacacc agcgaacatg gtcagctgga tctgctgtat   1560

ccgagcattg atagcgaaag cgaaattctg ccgggcgaaa accaggtgtt ttacgataac   1620

cgtacccaga acgtggatta cctgaacagc tattactacc tggaaagcca gaaactgagc   1680

gataacgtgg aagattttac ctttacccgc agcattgaag aagcgctgga taacagcgcg   1740

aaagtttaca cctattttcc gaccctggcg aacaaagtta atgcgggtgt tcagggcggt   1800

ctgtttctga tgtgggcgaa cgatgtggtg gaagatttca ccaccaacat cctgcgtaaa   1860

gataccctgg ataaaatcag cgatgttagc gcgattattc cgtatattgg tccggcgctg   1920

aacattagca atagcgtgcg tcgtggcaat tttaccgaag cgtttgcggt taccggtgtg   1980

accattctgc tggaagcgtt tccggaattt accattccgg cgctgggtgc gtttgtgatc   2040

tatagcaaag tgcaggaacg caacgaaatc atcaaaacca tcgataactg cctggaacag   2100

cgtattaaac gctggaaaga tagctatgaa tggatgatgg gcacctggct gagccgtatt   2160

atcacccagt tcaacaacat cagctaccag atgtacgata gcctgaacta tcaggcgggt   2220

gcgattaaag cgaaaatcga tctggaatac aaaaaataca gcggcagcga taaagaaaac   2280

atcaaaagcc aggttgaaaa cctgaaaaac agcctggatg tgaaaattag cgaagcgatg   2340

aataacatca acaaattcat ccgcgaatgc agcgtgacct acctgttcaa aaacatgctg   2400

ccgaaagtga tcgatgaact gaacgaattt gatcgcaaca ccaaagcgaa actgatcaac   2460

ctgatcgata gccacaacat tattctggtg ggcgaagtgg ataaactgaa agcgaaagtt   2520

aacaacagct tccagaacac catcccgttt aacatcttca gctataccaa caacagcctg   2580

ctgaaagata tcatcaacga atacttcaat ctagaaggcg gtggcggtag cggcggtggc   2640

ggtagcggcg gtggcggtag cgcactagtg ggtggtcgtg gtgacatgtt cggtgcttga   2700

taaaagctt                                                            2709
```

```
<210> SEQ ID NO 10
<211> LENGTH: 901
<212> TYPE: PRT
<213> ORGANISM: Unknown
<220> FEATURE:
<223> OTHER INFORMATION: Protein sequence of RGD-C fusion

<400> SEQUENCE: 10

Gly Ser Glu Phe Met Pro Ile Thr Ile Asn Asn Phe Asn Tyr Ser Asp
1               5                   10                  15

Pro Val Asp Asn Lys Asn Ile Leu Tyr Leu Asp Thr His Leu Asn Thr
            20                  25                  30

Leu Ala Asn Glu Pro Glu Lys Ala Phe Arg Ile Thr Gly Asn Ile Trp
        35                  40                  45

Val Ile Pro Asp Arg Phe Ser Arg Asn Ser Asn Pro Asn Leu Asn Lys
    50                  55                  60

Pro Pro Arg Val Thr Ser Pro Lys Ser Gly Tyr Tyr Asp Pro Asn Tyr
65                  70                  75                  80

Leu Ser Thr Asp Ser Asp Lys Asp Thr Phe Leu Lys Glu Ile Ile Lys
                85                  90                  95

Leu Phe Lys Arg Ile Asn Ser Arg Glu Ile Gly Glu Glu Leu Ile Tyr
            100                 105                 110

Arg Leu Ser Thr Asp Ile Pro Phe Pro Gly Asn Asn Asn Thr Pro Ile
        115                 120                 125
```

-continued

```
Asn Thr Phe Asp Phe Asp Val Asp Phe Asn Ser Val Asp Val Lys Thr
    130                 135                 140

Arg Gln Gly Asn Asn Trp Val Lys Thr Gly Ser Ile Asn Pro Ser Val
145                 150                 155                 160

Ile Ile Thr Gly Pro Arg Glu Asn Ile Ile Asp Pro Glu Thr Ser Thr
                165                 170                 175

Phe Lys Leu Thr Asn Asn Thr Phe Ala Ala Gln Glu Gly Phe Gly Ala
            180                 185                 190

Leu Ser Ile Ile Ser Ile Ser Pro Arg Phe Met Leu Thr Tyr Ser Asn
        195                 200                 205

Ala Thr Asn Asp Val Gly Glu Gly Arg Phe Ser Lys Ser Glu Phe Cys
    210                 215                 220

Met Asp Pro Ile Leu Ile Leu Met His Glu Leu Asn His Ala Met His
225                 230                 235                 240

Asn Leu Tyr Gly Ile Ala Ile Pro Asn Asp Gln Thr Ile Ser Ser Val
                245                 250                 255

Thr Ser Asn Ile Phe Tyr Ser Gln Tyr Asn Val Lys Leu Glu Tyr Ala
            260                 265                 270

Glu Ile Tyr Ala Phe Gly Gly Pro Thr Ile Asp Leu Ile Pro Lys Ser
        275                 280                 285

Ala Arg Lys Tyr Phe Glu Glu Lys Ala Leu Asp Tyr Tyr Arg Ser Ile
    290                 295                 300

Ala Lys Arg Leu Asn Ser Ile Thr Thr Ala Asn Pro Ser Ser Phe Asn
305                 310                 315                 320

Lys Tyr Ile Gly Glu Tyr Lys Gln Lys Leu Ile Arg Lys Tyr Arg Phe
                325                 330                 335

Val Val Glu Ser Ser Gly Glu Val Thr Val Asn Arg Asn Lys Phe Val
            340                 345                 350

Glu Leu Tyr Asn Glu Leu Thr Gln Ile Phe Thr Glu Phe Asn Tyr Ala
        355                 360                 365

Lys Ile Tyr Asn Val Gln Asn Arg Lys Ile Tyr Leu Ser Asn Val Tyr
    370                 375                 380

Thr Pro Val Thr Ala Asn Ile Leu Asp Asp Asn Val Tyr Asp Ile Gln
385                 390                 395                 400

Asn Gly Phe Asn Ile Pro Lys Ser Asn Leu Asn Val Leu Phe Met Gly
                405                 410                 415

Gln Asn Leu Ser Arg Asn Pro Ala Leu Arg Lys Val Asn Pro Glu Asn
            420                 425                 430

Met Leu Tyr Leu Phe Thr Lys Phe Cys Val Asp Ala Ile Asp Gly Arg
        435                 440                 445

Ser Leu Tyr Asn Lys Thr Leu Gln Cys Arg Glu Leu Leu Val Lys Asn
    450                 455                 460

Thr Asp Leu Pro Phe Ile Gly Asp Ile Ser Asp Val Lys Thr Asp Ile
465                 470                 475                 480

Phe Leu Arg Lys Asp Ile Asn Glu Glu Thr Glu Val Ile Tyr Tyr Pro
                485                 490                 495

Asp Asn Val Ser Val Asp Gln Val Ile Leu Ser Lys Asn Thr Ser Glu
            500                 505                 510

His Gly Gln Leu Asp Leu Leu Tyr Pro Ser Ile Asp Ser Glu Ser Glu
        515                 520                 525

Ile Leu Pro Gly Glu Asn Gln Val Phe Tyr Asp Asn Arg Thr Gln Asn
    530                 535                 540

Val Asp Tyr Leu Asn Ser Tyr Tyr Tyr Leu Glu Ser Gln Lys Leu Ser
```

-continued

```
545                 550                 555                 560

Asp Asn Val Glu Asp Phe Thr Phe Thr Arg Ser Ile Glu Glu Ala Leu
                565                 570                 575

Asp Asn Ser Ala Lys Val Tyr Thr Tyr Phe Pro Thr Leu Ala Asn Lys
            580                 585                 590

Val Asn Ala Gly Val Gln Gly Gly Leu Phe Leu Met Trp Ala Asn Asp
        595                 600                 605

Val Val Glu Asp Phe Thr Thr Asn Ile Leu Arg Lys Asp Thr Leu Asp
    610                 615                 620

Lys Ile Ser Asp Val Ser Ala Ile Ile Pro Tyr Ile Gly Pro Ala Leu
625                 630                 635                 640

Asn Ile Ser Asn Ser Val Arg Arg Gly Asn Phe Thr Glu Ala Phe Ala
                645                 650                 655

Val Thr Gly Val Thr Ile Leu Leu Glu Ala Phe Pro Glu Phe Thr Ile
            660                 665                 670

Pro Ala Leu Gly Ala Phe Val Ile Tyr Ser Lys Val Gln Glu Arg Asn
        675                 680                 685

Glu Ile Ile Lys Thr Ile Asp Asn Cys Leu Glu Gln Arg Ile Lys Arg
    690                 695                 700

Trp Lys Asp Ser Tyr Glu Trp Met Met Gly Thr Trp Leu Ser Arg Ile
705                 710                 715                 720

Ile Thr Gln Phe Asn Asn Ile Ser Tyr Gln Met Tyr Asp Ser Leu Asn
                725                 730                 735

Tyr Gln Ala Gly Ala Ile Lys Ala Lys Ile Asp Leu Glu Tyr Lys Lys
            740                 745                 750

Tyr Ser Gly Ser Asp Lys Glu Asn Ile Lys Ser Gln Val Glu Asn Leu
        755                 760                 765

Lys Asn Ser Leu Asp Val Lys Ile Ser Glu Ala Met Asn Asn Ile Asn
    770                 775                 780

Lys Phe Ile Arg Glu Cys Ser Val Thr Tyr Leu Phe Lys Asn Met Leu
785                 790                 795                 800

Pro Lys Val Ile Asp Glu Leu Asn Glu Phe Asp Arg Asn Thr Lys Ala
                805                 810                 815

Lys Leu Ile Asn Leu Ile Asp Ser His Asn Ile Ile Leu Val Gly Glu
            820                 825                 830

Val Asp Lys Leu Lys Ala Lys Val Asn Asn Ser Phe Gln Asn Thr Ile
        835                 840                 845

Pro Phe Asn Ile Phe Ser Tyr Thr Asn Asn Ser Leu Leu Lys Asp Ile
    850                 855                 860

Ile Asn Glu Tyr Phe Asn Leu Glu Gly Gly Gly Gly Ser Gly Gly Gly
865                 870                 875                 880

Gly Ser Gly Gly Gly Gly Ser Ala Leu Val Gly Gly Arg Gly Asp Met
                885                 890                 895

Phe Gly Ala Lys Leu
            900


<210> SEQ ID NO 11
<211> LENGTH: 126
<212> TYPE: DNA
<213> ORGANISM: Unknown
<220> FEATURE:
<223> OTHER INFORMATION: DNA sequence of cyclic RGD linker

<400> SEQUENCE: 11

ggatccgtcg acctgcaggg tctagaaggc ggtggcggta gcggcggtgg cggtagcggc      60
```

ggtggcggta gcgcactagt gggtggttgc cgtggtgaca tgttcggttg cgcttgataa 120
aagctt 126

<210> SEQ ID NO 12
<211> LENGTH: 2715
<212> TYPE: DNA
<213> ORGANISM: Unknown
<220> FEATURE:
<223> OTHER INFORMATION: DNA sequence of cyclic RGD-C fusion

<400> SEQUENCE: 12
ggatccgaat tcatgccgat caccatcaac aacttcaact acagcgatcc ggtggataac 60
aaaaacatcc tgtacctgga tacccatctg aataccctgg cgaacgaacc ggaaaaagcg 120
tttcgtatca ccggcaacat ttgggttatt ccggatcgtt ttagccgtaa cagcaacccg 180
aatctgaata aaccgccgcg tgttaccagc ccgaaaagcg gttattacga tccgaactat 240
ctgagcaccg atagcgataa agataccttc ctgaaagaaa tcatcaaact gttcaaacgc 300
atcaacagcc gtgaaattgg cgaagaactg atctatcgcc tgagcaccga tattccgttt 360
ccgggcaaca acaacacccc gatcaacacc tttgatttcg atgtggattt caacagcgtt 420
gatgttaaaa cccgccaggg taacaattgg gtgaaaaccg gcagcattaa cccgagcgtg 480
attattaccg gtccgcgcga aaacattatt gatccggaaa ccagcacctt taaactgacc 540
aacaacacct ttgcggcgca ggaaggtttt ggcgcgctga gcattattag cattagcccg 600
cgctttatgc tgacctatag caacgcgacc aacgatgttg gtgaaggccg tttcagcaaa 660
agcgaatttt gcatggaccc gatcctgatc ctgatgcatg aactgaacca tgcgatgcat 720
aacctgtatg gcatcgcgat tccgaacgat cagaccatta gcagcgtgac cagcaacatc 780
ttttacagcc agtacaacgt gaaactggaa tatgcggaaa tctatgcgtt tggcggtccg 840
accattgatc tgattccgaa aagcgcgcgc aaatacttcg aagaaaaagc gctggattac 900
tatcgcagca ttgcgaaacg tctgaacagc attaccaccg cgaatccgag cagcttcaac 960
aaatatatcg gcgaatataa acagaaactg atccgcaaat atcgctttgt ggtggaaagc 1020
agcggcgaag ttaccgttaa ccgcaataaa ttcgtggaac tgtacaacga actgacccag 1080
atcttcaccg aatttaacta tgcgaaaatc tataacgtgc agaaccgtaa aatctacctg 1140
agcaacgtgt ataccccggt gaccgcgaat attctggatg ataacgtgta cgatatccag 1200
aacggcttta acatcccgaa aagcaacctg aacgttctgt ttatgggcca gaacctgagc 1260
cgtaatccgg cgctgcgtaa agtgaacccg gaaaacatgc tgtacctgtt caccaaattt 1320
tgcgtcgacg cgattgatgg tcgtagcctg tacaacaaaa ccctgcagtg tcgtgaactg 1380
ctggtgaaaa acaccgatct gccgtttatt ggcgatatca gcgatgtgaa aaccgatatc 1440
ttcctgcgca aagatatcaa cgaagaaacc gaagtgatct actacccgga taacgtgagc 1500
gttgatcagg tgatcctgag caaaaacacc agcgaacatg gtcagctgga tctgctgtat 1560
ccgagcattg atagcgaaag cgaaattctg ccgggcgaaa accaggtgtt ttacgataac 1620
cgtacccaga acgtggatta cctgaacagc tattactacc tggaaagcca gaaactgagc 1680
gataacgtgg aagattttac ctttacccgc agcattgaag aagcgctgga taacagcgcg 1740
aaagtttaca cctattttcc gaccctggcg aacaaagtta atgcgggtgt tcagggcggt 1800
ctgtttctga tgtgggcgaa cgatgtggtg gaagatttca ccaccaacat cctgcgtaaa 1860
gataccctgg ataaaatcag cgatgttagc gcgattattc cgtatattgg tccggcgctg 1920

-continued

```
aacattagca atagcgtgcg tcgtggcaat tttaccgaag cgtttgcggt taccggtgtg   1980

accattctgc tggaagcgtt tccggaattt accattccgg cgctgggtgc gtttgtgatc   2040

tatagcaaag tgcaggaacg caacgaaatc atcaaaacca tcgataactg cctggaacag   2100

cgtattaaac gctggaaaga tagctatgaa tggatgatgg gcacctggct gagccgtatt   2160

atcacccagt tcaacaacat cagctaccag atgtacgata gcctgaacta tcaggcgggt   2220

gcgattaaag cgaaaatcga tctggaatac aaaaaataca gcggcagcga taaagaaaac   2280

atcaaaagcc aggttgaaaa cctgaaaaac agcctggatg tgaaaattag cgaagcgatg   2340

aataacatca acaaattcat ccgcgaatgc agcgtgacct acctgttcaa aaacatgctg   2400

ccgaaagtga tcgatgaact gaacgaattt gatcgcaaca ccaaagcgaa actgatcaac   2460

ctgatcgata gccacaacat tattctggtg ggcgaagtgg ataaactgaa agcgaaagtt   2520

aacaacagct tccagaacac catcccgttt aacatcttca gctataccaa caacagcctg   2580

ctgaaagata tcatcaacga atacttcaat ctagaaggcg gtggcggtag cggcggtggc   2640

ggtagcggcg gtggcggtag cgcactagtg ggtggttgcc gtggtgacat gttcggttgc   2700

gcttgataaa agctt                                                    2715
```

<210> SEQ ID NO 13
<211> LENGTH: 903
<212> TYPE: PRT
<213> ORGANISM: Unknown
<220> FEATURE:
<223> OTHER INFORMATION: Protein sequence of cyclic RGD-C fusion

<400> SEQUENCE: 13

```
Gly Ser Glu Phe Met Pro Ile Thr Ile Asn Asn Phe Asn Tyr Ser Asp
1               5                   10                  15

Pro Val Asp Asn Lys Asn Ile Leu Tyr Leu Asp Thr His Leu Asn Thr
            20                  25                  30

Leu Ala Asn Glu Pro Glu Lys Ala Phe Arg Ile Thr Gly Asn Ile Trp
        35                  40                  45

Val Ile Pro Asp Arg Phe Ser Arg Asn Ser Asn Pro Asn Leu Asn Lys
    50                  55                  60

Pro Pro Arg Val Thr Ser Pro Lys Ser Gly Tyr Tyr Asp Pro Asn Tyr
65                  70                  75                  80

Leu Ser Thr Asp Ser Asp Lys Asp Thr Phe Leu Lys Glu Ile Ile Lys
                85                  90                  95

Leu Phe Lys Arg Ile Asn Ser Arg Glu Ile Gly Glu Glu Leu Ile Tyr
            100                 105                 110

Arg Leu Ser Thr Asp Ile Pro Phe Pro Gly Asn Asn Asn Thr Pro Ile
        115                 120                 125

Asn Thr Phe Asp Phe Asp Val Asp Phe Asn Ser Val Asp Val Lys Thr
    130                 135                 140

Arg Gln Gly Asn Asn Trp Val Lys Thr Gly Ser Ile Asn Pro Ser Val
145                 150                 155                 160

Ile Ile Thr Gly Pro Arg Glu Asn Ile Ile Asp Pro Glu Thr Ser Thr
                165                 170                 175

Phe Lys Leu Thr Asn Asn Thr Phe Ala Ala Gln Glu Gly Phe Gly Ala
            180                 185                 190

Leu Ser Ile Ile Ser Ile Ser Pro Arg Phe Met Leu Thr Tyr Ser Asn
        195                 200                 205

Ala Thr Asn Asp Val Gly Glu Gly Arg Phe Ser Lys Ser Glu Phe Cys
    210                 215                 220
```

```
Met Asp Pro Ile Leu Ile Leu Met His Glu Leu Asn His Ala Met His
225                 230                 235                 240

Asn Leu Tyr Gly Ile Ala Ile Pro Asn Asp Gln Thr Ile Ser Ser Val
                245                 250                 255

Thr Ser Asn Ile Phe Tyr Ser Gln Tyr Asn Val Lys Leu Glu Tyr Ala
            260                 265                 270

Glu Ile Tyr Ala Phe Gly Gly Pro Thr Ile Asp Leu Ile Pro Lys Ser
        275                 280                 285

Ala Arg Lys Tyr Phe Glu Glu Lys Ala Leu Asp Tyr Tyr Arg Ser Ile
    290                 295                 300

Ala Lys Arg Leu Asn Ser Ile Thr Thr Ala Asn Pro Ser Ser Phe Asn
305                 310                 315                 320

Lys Tyr Ile Gly Glu Tyr Lys Gln Lys Leu Ile Arg Lys Tyr Arg Phe
                325                 330                 335

Val Val Glu Ser Ser Gly Glu Val Thr Val Asn Arg Asn Lys Phe Val
            340                 345                 350

Glu Leu Tyr Asn Glu Leu Thr Gln Ile Phe Thr Glu Phe Asn Tyr Ala
        355                 360                 365

Lys Ile Tyr Asn Val Gln Asn Arg Lys Ile Tyr Leu Ser Asn Val Tyr
    370                 375                 380

Thr Pro Val Thr Ala Asn Ile Leu Asp Asp Asn Val Tyr Asp Ile Gln
385                 390                 395                 400

Asn Gly Phe Asn Ile Pro Lys Ser Asn Leu Asn Val Leu Phe Met Gly
                405                 410                 415

Gln Asn Leu Ser Arg Asn Pro Ala Leu Arg Lys Val Asn Pro Glu Asn
            420                 425                 430

Met Leu Tyr Leu Phe Thr Lys Phe Cys Val Asp Ala Ile Asp Gly Arg
        435                 440                 445

Ser Leu Tyr Asn Lys Thr Leu Gln Cys Arg Glu Leu Leu Val Lys Asn
    450                 455                 460

Thr Asp Leu Pro Phe Ile Gly Asp Ile Ser Asp Val Lys Thr Asp Ile
465                 470                 475                 480

Phe Leu Arg Lys Asp Ile Asn Glu Glu Thr Glu Val Ile Tyr Tyr Pro
                485                 490                 495

Asp Asn Val Ser Val Asp Gln Val Ile Leu Ser Lys Asn Thr Ser Glu
            500                 505                 510

His Gly Gln Leu Asp Leu Leu Tyr Pro Ser Ile Asp Ser Glu Ser Glu
        515                 520                 525

Ile Leu Pro Gly Glu Asn Gln Val Phe Tyr Asp Asn Arg Thr Gln Asn
    530                 535                 540

Val Asp Tyr Leu Asn Ser Tyr Tyr Tyr Leu Glu Ser Gln Lys Leu Ser
545                 550                 555                 560

Asp Asn Val Glu Asp Phe Thr Phe Thr Arg Ser Ile Glu Glu Ala Leu
                565                 570                 575

Asp Asn Ser Ala Lys Val Tyr Thr Tyr Phe Pro Thr Leu Ala Asn Lys
            580                 585                 590

Val Asn Ala Gly Val Gln Gly Gly Leu Phe Leu Met Trp Ala Asn Asp
        595                 600                 605

Val Val Glu Asp Phe Thr Thr Asn Ile Leu Arg Lys Asp Thr Leu Asp
    610                 615                 620

Lys Ile Ser Asp Val Ser Ala Ile Ile Pro Tyr Ile Gly Pro Ala Leu
625                 630                 635                 640
```

```
Asn Ile Ser Asn Ser Val Arg Arg Gly Asn Phe Thr Glu Ala Phe Ala
                645                 650                 655

Val Thr Gly Val Thr Ile Leu Leu Glu Ala Phe Pro Glu Phe Thr Ile
            660                 665                 670

Pro Ala Leu Gly Ala Phe Val Ile Tyr Ser Lys Val Gln Glu Arg Asn
        675                 680                 685

Glu Ile Ile Lys Thr Ile Asp Asn Cys Leu Glu Gln Arg Ile Lys Arg
    690                 695                 700

Trp Lys Asp Ser Tyr Glu Trp Met Met Gly Thr Trp Leu Ser Arg Ile
705                 710                 715                 720

Ile Thr Gln Phe Asn Asn Ile Ser Tyr Gln Met Tyr Asp Ser Leu Asn
                725                 730                 735

Tyr Gln Ala Gly Ala Ile Lys Ala Lys Ile Asp Leu Glu Tyr Lys Lys
            740                 745                 750

Tyr Ser Gly Ser Asp Lys Glu Asn Ile Lys Ser Gln Val Glu Asn Leu
        755                 760                 765

Lys Asn Ser Leu Asp Val Lys Ile Ser Glu Ala Met Asn Asn Ile Asn
    770                 775                 780

Lys Phe Ile Arg Glu Cys Ser Val Thr Tyr Leu Phe Lys Asn Met Leu
785                 790                 795                 800

Pro Lys Val Ile Asp Glu Leu Asn Glu Phe Asp Arg Asn Thr Lys Ala
                805                 810                 815

Lys Leu Ile Asn Leu Ile Asp Ser His Asn Ile Ile Leu Val Gly Glu
            820                 825                 830

Val Asp Lys Leu Lys Ala Lys Val Asn Asn Ser Phe Gln Asn Thr Ile
        835                 840                 845

Pro Phe Asn Ile Phe Ser Tyr Thr Asn Asn Ser Leu Leu Lys Asp Ile
    850                 855                 860

Ile Asn Glu Tyr Phe Asn Leu Glu Gly Gly Gly Gly Ser Gly Gly Gly
865                 870                 875                 880

Gly Ser Gly Gly Gly Gly Ser Ala Leu Val Gly Gly Cys Arg Gly Asp
                885                 890                 895

Met Phe Gly Cys Ala Lys Leu
            900
```

<210> SEQ ID NO 14
<211> LENGTH: 156
<212> TYPE: DNA
<213> ORGANISM: Unknown
<220> FEATURE:
<223> OTHER INFORMATION: DNA sequence of the LC/C-RGD-HN/C LINKER

<400> SEQUENCE: 14

```
ggatccacgc acgtcgacgc gattgatggt cgtggtggtc gtggtgacat gttcggtgct      60

gcgctagcgg gcggtggcgg tagcggcggt ggcggtagcg gcggtggcgg tagcgcacta     120

gtgctgcaga cgcacggtct agaatgataa aagctt                               156
```

<210> SEQ ID NO 15
<211> LENGTH: 2733
<212> TYPE: DNA
<213> ORGANISM: Unknown
<220> FEATURE:
<223> OTHER INFORMATION: DNA sequence of the LC/C-RGD-HN/C fusion

<400> SEQUENCE: 15

```
ggatccgaat tcatgccgat caccatcaac aacttcaact acagcgatcc ggtggataac      60
```

```
aaaaacatcc tgtacctgga tacccatctg aataccctgg cgaacgaacc ggaaaaagcg    120
tttcgtatca ccggcaacat ttgggttatt ccggatcgtt ttagccgtaa cagcaacccg    180
aatctgaata aaccgccgcg tgttaccagc ccgaaaagcg gttattacga tccgaactat    240
ctgagcaccg atagcgataa agataccttc ctgaaagaaa tcatcaaact gttcaaacgc    300
atcaacagcc gtgaaattgg cgaagaactg atctatcgcc tgagcaccga tattccgttt    360
ccgggcaaca acaacacccc gatcaacacc tttgatttcg atgtggattt caacagcgtt    420
gatgttaaaa cccgccaggg taacaattgg gtgaaaaccg gcagcattaa cccgagcgtg    480
attattaccg gtccgcgcga aaacattatt gatccggaaa ccagcacctt taaactgacc    540
aacaacacct ttgcggcgca ggaaggtttt ggcgcgctga gcattattag cattagcccg    600
cgctttatgc tgacctatag caacgcgacc aacgatgttg gtgaaggccg tttcagcaaa    660
agcgaatttt gcatggaccc gatcctgatc ctgatgcatg aactgaacca tgcgatgcat    720
aacctgtatg gcatcgcgat tccgaacgat cagaccatta gcagcgtgac cagcaacatc    780
ttttacagcc agtacaacgt gaaactggaa tatgcggaaa tctatgcgtt tggcggtccg    840
accattgatc tgattccgaa aagcgcgcgc aaatacttcg aagaaaaagc gctggattac    900
tatcgcagca ttgcgaaacg tctgaacagc attaccaccg cgaatccgag cagcttcaac    960
aaatatatcg gcgaatataa acagaaactg atccgcaaat atcgctttgt ggtggaaagc   1020
agcggcgaag ttaccgttaa ccgcaataaa ttcgtggaac tgtacaacga actgacccag   1080
atcttcaccg aatttaacta tgcgaaaatc tataacgtgc agaaccgtaa aatctacctg   1140
agcaacgtgt ataccccggt gaccgcgaat attctggatg ataacgtgta cgatatccag   1200
aacggcttta acatcccgaa aagcaacctg aacgttctgt ttatgggcca gaacctgagc   1260
cgtaatccgg cgctgcgtaa agtgaacccg gaaaacatgc tgtacctgtt caccaaattt   1320
tgcgtcgacg cgattgatgg tcgtggtggt cgtggtgaca tgttcggtgc tgcgctagcg   1380
ggcggtggcg gtagcggcgg tggcggtagc ggcggtggcg gtagcgcact agtgctgcag   1440
tgtcgtgaac tgctggtgaa aaacaccgat ctgccgttta ttggcgatat cagcgatgtg   1500
aaaaccgata tcttcctgcg caaagatatc aacgaagaaa ccgaagtgat ctactacccg   1560
gataacgtga gcgttgatca ggtgatcctg agcaaaaaca ccagcgaaca tggtcagctg   1620
gatctgctgt atccgagcat tgatagcgaa agcgaaattc tgccgggcga aaaccaggtg   1680
ttttacgata accgtaccca gaacgtggat tacctgaaca gctattacta cctggaaagc   1740
cagaaactga gcgataacgt ggaagatttt acctttaccc gcagcattga agaagcgctg   1800
gataacagcg cgaaagttta cacctatttt ccgaccctgg cgaacaaagt taatgcgggt   1860
gttcagggcg gtctgtttct gatgtgggcg aacgatgtgg tggaagattt caccaccaac   1920
atcctgcgta aagataccct ggataaaatc agcgatgtta gcgcgattat tccgtatatt   1980
ggtccggcgc tgaacattag caatagcgtg cgtcgtggca attttaccga agcgtttgcg   2040
gttaccggtg tgaccattct gctggaagcg tttccggaat ttaccattcc ggcgctgggt   2100
gcgtttgtga tctatagcaa agtgcaggaa cgcaacgaaa tcatcaaaac catcgataac   2160
tgcctggaac agcgtattaa acgctggaaa gatagctatg aatggatgat gggcacctgg   2220
ctgagccgta ttatcaccca gttcaacaac atcagctacc agatgtacga tagcctgaac   2280
tatcaggcgg gtgcgattaa agcgaaaatc gatctggaat acaaaaaata cagcggcagc   2340
gataaagaaa acatcaaaag ccaggttgaa aacctgaaaa acagcctgga tgtgaaaatt   2400
agcgaagcga tgaataacat caacaaattc atccgcgaat gcagcgtgac ctacctgttc   2460
```

```
aaaaacatgc tgccgaaagt gatcgatgaa ctgaacgaat ttgatcgcaa caccaaagcg   2520

aaactgatca acctgatcga tagccacaac attattctgg tgggcgaagt ggataaactg   2580

aaagcgaaag ttaacaacag cttccagaac accatcccgt ttaacatctt cagctatacc   2640

aacaacagcc tgctgaaaga tatcatcaac gaatacttca atctagaagc actagcgagt   2700

gggcaccatc accatcacca ttaatgaaag ctt                                2733


<210> SEQ ID NO 16
<211> LENGTH: 909
<212> TYPE: PRT
<213> ORGANISM: Unknown
<220> FEATURE:
<223> OTHER INFORMATION: Protein sequence of the LC/C-RGD-HN/C fusion

<400> SEQUENCE: 16

Gly Ser Glu Phe Met Pro Ile Thr Ile Asn Asn Phe Asn Tyr Ser Asp
1               5                   10                  15

Pro Val Asp Asn Lys Asn Ile Leu Tyr Leu Asp Thr His Leu Asn Thr
            20                  25                  30

Leu Ala Asn Glu Pro Glu Lys Ala Phe Arg Ile Thr Gly Asn Ile Trp
        35                  40                  45

Val Ile Pro Asp Arg Phe Ser Arg Asn Ser Asn Pro Asn Leu Asn Lys
    50                  55                  60

Pro Pro Arg Val Thr Ser Pro Lys Ser Gly Tyr Tyr Asp Pro Asn Tyr
65                  70                  75                  80

Leu Ser Thr Asp Ser Asp Lys Asp Thr Phe Leu Lys Glu Ile Ile Lys
                85                  90                  95

Leu Phe Lys Arg Ile Asn Ser Arg Glu Ile Gly Glu Glu Leu Ile Tyr
            100                 105                 110

Arg Leu Ser Thr Asp Ile Pro Phe Pro Gly Asn Asn Asn Thr Pro Ile
        115                 120                 125

Asn Thr Phe Asp Phe Asp Val Asp Phe Asn Ser Val Asp Val Lys Thr
    130                 135                 140

Arg Gln Gly Asn Asn Trp Val Lys Thr Gly Ser Ile Asn Pro Ser Val
145                 150                 155                 160

Ile Ile Thr Gly Pro Arg Glu Asn Ile Ile Asp Pro Glu Thr Ser Thr
                165                 170                 175

Phe Lys Leu Thr Asn Asn Thr Phe Ala Ala Gln Glu Gly Phe Gly Ala
            180                 185                 190

Leu Ser Ile Ile Ser Ile Ser Pro Arg Phe Met Leu Thr Tyr Ser Asn
        195                 200                 205

Ala Thr Asn Asp Val Gly Glu Gly Arg Phe Ser Lys Ser Glu Phe Cys
    210                 215                 220

Met Asp Pro Ile Leu Ile Leu Met His Glu Leu Asn His Ala Met His
225                 230                 235                 240

Asn Leu Tyr Gly Ile Ala Ile Pro Asn Asp Gln Thr Ile Ser Ser Val
                245                 250                 255

Thr Ser Asn Ile Phe Tyr Ser Gln Tyr Asn Val Lys Leu Glu Tyr Ala
            260                 265                 270

Glu Ile Tyr Ala Phe Gly Gly Pro Thr Ile Asp Leu Ile Pro Lys Ser
        275                 280                 285

Ala Arg Lys Tyr Phe Glu Glu Lys Ala Leu Asp Tyr Tyr Arg Ser Ile
    290                 295                 300

Ala Lys Arg Leu Asn Ser Ile Thr Thr Ala Asn Pro Ser Ser Phe Asn
```

-continued

```
305                 310                 315                 320

Lys Tyr Ile Gly Glu Tyr Lys Gln Lys Leu Ile Arg Lys Tyr Arg Phe
                325                 330                 335

Val Val Glu Ser Ser Gly Glu Val Thr Val Asn Arg Asn Lys Phe Val
            340                 345                 350

Glu Leu Tyr Asn Glu Leu Thr Gln Ile Phe Thr Glu Phe Asn Tyr Ala
        355                 360                 365

Lys Ile Tyr Asn Val Gln Asn Arg Lys Ile Tyr Leu Ser Asn Val Tyr
    370                 375                 380

Thr Pro Val Thr Ala Asn Ile Leu Asp Asp Asn Val Tyr Asp Ile Gln
385                 390                 395                 400

Asn Gly Phe Asn Ile Pro Lys Ser Asn Leu Asn Val Leu Phe Met Gly
                405                 410                 415

Gln Asn Leu Ser Arg Asn Pro Ala Leu Arg Lys Val Asn Pro Glu Asn
            420                 425                 430

Met Leu Tyr Leu Phe Thr Lys Phe Cys Val Asp Ala Ile Asp Gly Arg
        435                 440                 445

Gly Gly Arg Gly Asp Met Phe Gly Ala Ala Leu Ala Gly Gly Gly Gly
    450                 455                 460

Ser Gly Gly Gly Gly Ser Gly Gly Gly Gly Ser Ala Leu Val Leu Gln
465                 470                 475                 480

Cys Arg Glu Leu Leu Val Lys Asn Thr Asp Leu Pro Phe Ile Gly Asp
                485                 490                 495

Ile Ser Asp Val Lys Thr Asp Ile Phe Leu Arg Lys Asp Ile Asn Glu
            500                 505                 510

Glu Thr Glu Val Ile Tyr Tyr Pro Asp Asn Val Ser Val Asp Gln Val
        515                 520                 525

Ile Leu Ser Lys Asn Thr Ser Glu His Gly Gln Leu Asp Leu Leu Tyr
    530                 535                 540

Pro Ser Ile Asp Ser Glu Ser Glu Ile Leu Pro Gly Glu Asn Gln Val
545                 550                 555                 560

Phe Tyr Asp Asn Arg Thr Gln Asn Val Asp Tyr Leu Asn Ser Tyr Tyr
                565                 570                 575

Tyr Leu Glu Ser Gln Lys Leu Ser Asp Asn Val Glu Asp Phe Thr Phe
            580                 585                 590

Thr Arg Ser Ile Glu Glu Ala Leu Asp Asn Ser Ala Lys Val Tyr Thr
        595                 600                 605

Tyr Phe Pro Thr Leu Ala Asn Lys Val Asn Ala Gly Val Gln Gly Gly
    610                 615                 620

Leu Phe Leu Met Trp Ala Asn Asp Val Val Glu Asp Phe Thr Thr Asn
625                 630                 635                 640

Ile Leu Arg Lys Asp Thr Leu Asp Lys Ile Ser Asp Val Ser Ala Ile
                645                 650                 655

Ile Pro Tyr Ile Gly Pro Ala Leu Asn Ile Ser Asn Ser Val Arg Arg
            660                 665                 670

Gly Asn Phe Thr Glu Ala Phe Ala Val Thr Gly Val Thr Ile Leu Leu
        675                 680                 685

Glu Ala Phe Pro Glu Phe Thr Ile Pro Ala Leu Gly Ala Phe Val Ile
    690                 695                 700

Tyr Ser Lys Val Gln Glu Arg Asn Glu Ile Ile Lys Thr Ile Asp Asn
705                 710                 715                 720

Cys Leu Glu Gln Arg Ile Lys Arg Trp Lys Asp Ser Tyr Glu Trp Met
                725                 730                 735
```

-continued

```
Met Gly Thr Trp Leu Ser Arg Ile Ile Thr Gln Phe Asn Asn Ile Ser
            740                 745                 750

Tyr Gln Met Tyr Asp Ser Leu Asn Tyr Gln Ala Gly Ala Ile Lys Ala
        755                 760                 765

Lys Ile Asp Leu Glu Tyr Lys Lys Tyr Ser Gly Ser Asp Lys Glu Asn
    770                 775                 780

Ile Lys Ser Gln Val Glu Asn Leu Lys Asn Ser Leu Asp Val Lys Ile
785                 790                 795                 800

Ser Glu Ala Met Asn Asn Ile Asn Lys Phe Ile Arg Glu Cys Ser Val
                805                 810                 815

Thr Tyr Leu Phe Lys Asn Met Leu Pro Lys Val Ile Asp Glu Leu Asn
            820                 825                 830

Glu Phe Asp Arg Asn Thr Lys Ala Lys Leu Ile Asn Leu Ile Asp Ser
        835                 840                 845

His Asn Ile Ile Leu Val Gly Glu Val Asp Lys Leu Lys Ala Lys Val
    850                 855                 860

Asn Asn Ser Phe Gln Asn Thr Ile Pro Phe Asn Ile Phe Ser Tyr Thr
865                 870                 875                 880

Asn Asn Ser Leu Leu Lys Asp Ile Ile Asn Glu Tyr Phe Asn Leu Glu
                885                 890                 895

Ala Leu Ala Ser Gly His His His His His His Lys Leu
            900                 905


<210> SEQ ID NO 17
<211> LENGTH: 2721
<212> TYPE: DNA
<213> ORGANISM: Unknown
<220> FEATURE:
<223> OTHER INFORMATION: DNA sequence of the fully synthesised
      LC/C-RGD-HN/C fusion

<400> SEQUENCE: 17

catatgggct ccgaatttat gccgataaca attaacaatt tcaattactc ggatccggtg     60

gacaacaaaa acattctgta tctggataca catttaaata ctcttgcgaa tgaaccagaa    120

aaagcgttca gaattacggg aaatatctgg gtcatcccgg atcgcttttc gagaaactca    180

aaccccaacc tgaacaaacc gccccgtgtt acaagtccga aaagcggcta ttacgatcca    240

aactaccttt cgaccgactc ggacaaagat acgtttctta aagagataat taaactgttt    300

aaacgtatca attcacgcga aattggggaa gagttaattt accgcctctc caccgacatt    360

ccgtttccag gcaataacaa tacaccgatt aacacctttg atttcgacgt ggacttcaac    420

agcgtggatg ttaaaacgcg ccagggtaat aactgggtaa agacgggatc gattaacccg    480

agtgttatta tcaccggtcc tcgcgaaaat atcatagacc cggaaactag cacgtttaaa    540

cttactaata acacattcgc ggcccaagaa gggttcggcg ccctgtcaat tataagcatc    600

agtccgcgct ttatgctgac ttacagtaat gctactaatg acgtgggtga gggccggttc    660

tctaaatcag aattttgcat ggatccaatc ctgattctga tgcatgagct gaatcacgct    720

atgcacaatc tgtatggtat tgctattccg aacgatcaga caattagttc agtgacgtct    780

aacatattct attctcaata taatgtgaaa ttggagtatg cggaaattta tgcatttggt    840

ggcccaacca tcgatcttat cccaaaatcc gcgcgcaagt atttcgaaga gaaagcatta    900

gattattacc ggtctatcgc aaagcgtctg aatagcataa ctacggctaa tccgagttcg    960

tttaacaaat atattggcga atataaacag aaactgatcc gtaaatatcg tttcgtagtg   1020
```

```
gaatcatccg gtgaagttac agtcaatcgt aataaatttg tggagttata caatgagctg   1080

acccaaatct tcaccgaatt caactatgct aaaatttata atgttcagaa ccgcaaaatc   1140

tacctgagta acgtgtatac gcctgtaaca gccaatattc tggatgacaa cgtgtatgat   1200

atccagaatg gctttaacat acctaaaagt aacttgaatg ttctctttat gggtcaaaat   1260

ctttcccgca atccggctct ccgaaaggta aatccggaaa acatgctcta tcttttcacc   1320

aaattttgcg tcgacgcaat cgatggacgt ggtgggagag gtgatatgtt tggggccgca   1380

ttagcgggtg gcgggggatc cggcggtggc ggtagtggcg gggcggaag cgcgctggta    1440

ctgcagtgtc gcgaactttt agttaagaat actgatctgc cattcattgg tgatatctca   1500

gatgtcaaga ccgatatttt cctccgtaaa gatatcaatg aggaaacaga ggtaatttac   1560

tatccggata atgtatctgt cgatcaggtc attctgtcca aaaatacctc tgaacacggt   1620

caactggatc tgctctaccc ctcgattgac tccgaatctg aaatcctccc tggagaaaac   1680

caggtctttt atgacaatcg tacccagaac gtggactact taaactctta ttactatttg   1740

gagagccaaa agttgtccga taacgttgaa gactttactt ttacccgatc tatagaagag   1800

gcattagaca actcggcgaa ggtttacacc tatttcccta ccttagccaa taaagtgaac   1860

gcaggtgtgc agggagggct gtttttgatg tgggccaatg atgtcgttga ggatttcaca   1920

accaacattc tgcgcaaaga cactttagat aaaatctcag atgtatcggc gatcattccc   1980

tacattggcc ctgcccttaa catttctaat tccgttcgtc gcggcaattt tactgaggcg   2040

tttgctgtca ccggtgtgac gatcttgctg gaggcttttc ctgaatttac cattcccgca   2100

ctgggggcat tcgttatcta cagtaaggtt caggaacgga acgaaattat aaaaacaatc   2160

gataattgcc tggaacagcg tatcaaacgg tggaaagata gctacgaatg gatgatgggc   2220

acgtggttga gccgcataat tacgcagttt aataacatct catatcaaat gtatgactcc   2280

ctgaattacc aggcgggcgc gattaaagcc aaaatcgatc tggagtacaa aaagtattca   2340

ggcagcgaca aagagaacat taaaagtcag gttgaaaacc tgaagaattc actggatgtg   2400

aaaatcagcg aagccatgaa taacattaat aaattcatcc gtgaatgtag tgtgacctat   2460

ctctttaaga atatgttgcc gaaagttatc gatgagctga acgagtttga tcgaaatacc   2520

aaagcaaagc tgattaattt aattgacagc cataatatta tactggtcgg cgaagtggat   2580

aaactgaagg ccaaggtaaa caattctttt caaaacacga taccattcaa catcttttct   2640

tatacgaata acagccttct gaaggacatt attaacgaat attttaattt ggaagccttg   2700

gctagcggat aatgaaagct t                                             2721
```

<210> SEQ ID NO 18
<211> LENGTH: 902
<212> TYPE: PRT
<213> ORGANISM: Unknown
<220> FEATURE:
<223> OTHER INFORMATION: Protein sequence of the fully synthesised
      LC/C-RGD-HN/C fusion

<400> SEQUENCE: 18

```
Met Gly Ser Glu Phe Met Pro Ile Thr Ile Asn Asn Phe Asn Tyr Ser
1               5                   10                  15

Asp Pro Val Asp Asn Lys Asn Ile Leu Tyr Leu Asp Thr His Leu Asn
            20                  25                  30

Thr Leu Ala Asn Glu Pro Glu Lys Ala Phe Arg Ile Thr Gly Asn Ile
        35                  40                  45

Trp Val Ile Pro Asp Arg Phe Ser Arg Asn Ser Asn Pro Asn Leu Asn
```

-continued

```
    50                  55                  60

Lys Pro Pro Arg Val Thr Ser Pro Lys Ser Gly Tyr Tyr Asp Pro Asn
65                  70                  75                  80

Tyr Leu Ser Thr Asp Ser Asp Lys Asp Thr Phe Leu Lys Glu Ile Ile
                85                  90                  95

Lys Leu Phe Lys Arg Ile Asn Ser Arg Glu Ile Gly Glu Glu Leu Ile
            100                 105                 110

Tyr Arg Leu Ser Thr Asp Ile Pro Phe Pro Gly Asn Asn Asn Thr Pro
        115                 120                 125

Ile Asn Thr Phe Asp Phe Asp Val Asp Phe Asn Ser Val Asp Val Lys
    130                 135                 140

Thr Arg Gln Gly Asn Asn Trp Val Lys Thr Gly Ser Ile Asn Pro Ser
145                 150                 155                 160

Val Ile Ile Thr Gly Pro Arg Glu Asn Ile Ile Asp Pro Glu Thr Ser
                165                 170                 175

Thr Phe Lys Leu Thr Asn Asn Thr Phe Ala Ala Gln Glu Gly Phe Gly
            180                 185                 190

Ala Leu Ser Ile Ile Ser Ile Ser Pro Arg Phe Met Leu Thr Tyr Ser
        195                 200                 205

Asn Ala Thr Asn Asp Val Gly Glu Gly Arg Phe Ser Lys Ser Glu Phe
    210                 215                 220

Cys Met Asp Pro Ile Leu Ile Leu Met His Glu Leu Asn His Ala Met
225                 230                 235                 240

His Asn Leu Tyr Gly Ile Ala Ile Pro Asn Asp Gln Thr Ile Ser Ser
                245                 250                 255

Val Thr Ser Asn Ile Phe Tyr Ser Gln Tyr Asn Val Lys Leu Glu Tyr
            260                 265                 270

Ala Glu Ile Tyr Ala Phe Gly Gly Pro Thr Ile Asp Leu Ile Pro Lys
        275                 280                 285

Ser Ala Arg Lys Tyr Phe Glu Glu Lys Ala Leu Asp Tyr Tyr Arg Ser
    290                 295                 300

Ile Ala Lys Arg Leu Asn Ser Ile Thr Thr Ala Asn Pro Ser Ser Phe
305                 310                 315                 320

Asn Lys Tyr Ile Gly Glu Tyr Lys Gln Lys Leu Ile Arg Lys Tyr Arg
                325                 330                 335

Phe Val Val Glu Ser Ser Gly Glu Val Thr Val Asn Arg Asn Lys Phe
            340                 345                 350

Val Glu Leu Tyr Asn Glu Leu Thr Gln Ile Phe Thr Glu Phe Asn Tyr
        355                 360                 365

Ala Lys Ile Tyr Asn Val Gln Asn Arg Lys Ile Tyr Leu Ser Asn Val
    370                 375                 380

Tyr Thr Pro Val Thr Ala Asn Ile Leu Asp Asp Asn Val Tyr Asp Ile
385                 390                 395                 400

Gln Asn Gly Phe Asn Ile Pro Lys Ser Asn Leu Asn Val Leu Phe Met
                405                 410                 415

Gly Gln Asn Leu Ser Arg Asn Pro Ala Leu Arg Lys Val Asn Pro Glu
            420                 425                 430

Asn Met Leu Tyr Leu Phe Thr Lys Phe Cys Val Asp Ala Ile Asp Gly
        435                 440                 445

Arg Gly Gly Arg Gly Asp Met Phe Gly Ala Ala Leu Ala Gly Gly Gly
    450                 455                 460

Gly Ser Gly Gly Gly Gly Ser Gly Gly Gly Gly Ser Ala Leu Val Leu
465                 470                 475                 480
```

-continued

```
Gln Cys Arg Glu Leu Leu Val Lys Asn Thr Asp Leu Pro Phe Ile Gly
                485                 490                 495

Asp Ile Ser Asp Val Lys Thr Asp Ile Phe Leu Arg Lys Asp Ile Asn
            500                 505                 510

Glu Glu Thr Glu Val Ile Tyr Tyr Pro Asp Asn Val Ser Val Asp Gln
        515                 520                 525

Val Ile Leu Ser Lys Asn Thr Ser Glu His Gly Gln Leu Asp Leu Leu
    530                 535                 540

Tyr Pro Ser Ile Asp Ser Glu Ser Glu Ile Leu Pro Gly Glu Asn Gln
545                 550                 555                 560

Val Phe Tyr Asp Asn Arg Thr Gln Asn Val Asp Tyr Leu Asn Ser Tyr
                565                 570                 575

Tyr Tyr Leu Glu Ser Gln Lys Leu Ser Asp Asn Val Glu Asp Phe Thr
            580                 585                 590

Phe Thr Arg Ser Ile Glu Glu Ala Leu Asp Asn Ser Ala Lys Val Tyr
        595                 600                 605

Thr Tyr Phe Pro Thr Leu Ala Asn Lys Val Asn Ala Gly Val Gln Gly
    610                 615                 620

Gly Leu Phe Leu Met Trp Ala Asn Asp Val Val Glu Asp Phe Thr Thr
625                 630                 635                 640

Asn Ile Leu Arg Lys Asp Thr Leu Asp Lys Ile Ser Asp Val Ser Ala
                645                 650                 655

Ile Ile Pro Tyr Ile Gly Pro Ala Leu Asn Ile Ser Asn Ser Val Arg
            660                 665                 670

Arg Gly Asn Phe Thr Glu Ala Phe Ala Val Thr Gly Val Thr Ile Leu
        675                 680                 685

Leu Glu Ala Phe Pro Glu Phe Thr Ile Pro Ala Leu Gly Ala Phe Val
    690                 695                 700

Ile Tyr Ser Lys Val Gln Glu Arg Asn Glu Ile Ile Lys Thr Ile Asp
705                 710                 715                 720

Asn Cys Leu Glu Gln Arg Ile Lys Arg Trp Lys Asp Ser Tyr Glu Trp
                725                 730                 735

Met Met Gly Thr Trp Leu Ser Arg Ile Ile Thr Gln Phe Asn Asn Ile
            740                 745                 750

Ser Tyr Gln Met Tyr Asp Ser Leu Asn Tyr Gln Ala Gly Ala Ile Lys
        755                 760                 765

Ala Lys Ile Asp Leu Glu Tyr Lys Lys Tyr Ser Gly Ser Asp Lys Glu
    770                 775                 780

Asn Ile Lys Ser Gln Val Glu Asn Leu Lys Asn Ser Leu Asp Val Lys
785                 790                 795                 800

Ile Ser Glu Ala Met Asn Asn Ile Asn Lys Phe Ile Arg Glu Cys Ser
                805                 810                 815

Val Thr Tyr Leu Phe Lys Asn Met Leu Pro Lys Val Ile Asp Glu Leu
            820                 825                 830

Asn Glu Phe Asp Arg Asn Thr Lys Ala Lys Leu Ile Asn Leu Ile Asp
        835                 840                 845

Ser His Asn Ile Ile Leu Val Gly Glu Val Asp Lys Leu Lys Ala Lys
    850                 855                 860

Val Asn Asn Ser Phe Gln Asn Thr Ile Pro Phe Asn Ile Phe Ser Tyr
865                 870                 875                 880

Thr Asn Asn Ser Leu Leu Lys Asp Ile Ile Asn Glu Tyr Phe Asn Leu
                885                 890                 895
```

-continued

Glu Ala Leu Ala Ser Gly
900

<210> SEQ ID NO 19
<211> LENGTH: 2859
<212> TYPE: DNA
<213> ORGANISM: Unknown
<220> FEATURE:
<223> OTHER INFORMATION: DNA sequence of the fully synthesised EGF-LHN/C fusion

<400> SEQUENCE: 19
catatgattt ccgaatttgg ctcggagttc atgccaatta cgattaacaa ttttaactat 60
agtgatccgg tggataataa aaacatttta tacctggata cccacttgaa tactcttgcc 120
aatgagcctg aaaaagcctt tcgcataacg ggtaacattt gggtcattcc ggaccgtttt 180
agccggaact ctaaccctaa tctgaataaa cctccgcgtg tcacgtctcc gaaaagtggg 240
tattacgatc caaattatct gagtaccgat tcagacaagg atacgtttct gaaagaaatc 300
ataaaacttt tcaaaagaat caactcccgt gaaatcggtg aagagctgat ctaccgtctg 360
tcgacggaca ttccttttcc gggaaacaat aacactccca ttaatacctt cgactttgat 420
gtcgatttca actcagtcga tgtgaaaacc cgccagggta ataactgggt taaaactgga 480
tccattaacc cgtccgttat tatcacaggt cctcgtgaaa atattataga tcctgagacc 540
tccacgttca agctgacgaa taacactttt gcggcacagg aagggtttgg tgccctttca 600
attatctcta tctctccgcg cttcatgtta acgtattcta acgcaaccaa cgatgttggc 660
gagggccgct tcagcaaaag tgaattctgt atggatccca ttctgatctt gatgcatgag 720
cttaaccacg ctatgcataa tctttatggt attgcaatcc caaacgatca gacgatctcc 780
agcgttacat ctaacatatt ctacagccaa tataatgtga agctcgaata tgcagagatt 840
tacgccttcg gtgggccgac cattgacctc attccaaagt ctgcccgtaa gtactttgag 900
gaaaaagcgt tggattacta tcgtagcatc gcgaaacgcc tgaattcaat tacaactgca 960
aacccatcta gcttcaacaa atacatcgga gaatataaac aaaagctgat acgcaaatat 1020
cgctttgtgg tcgaatcgtc cggggaagtg acagttaatc gaaataaatt tgttgaactc 1080
tataatgaat taacgcagat cttcacagaa tttaattatg ctaaaatcta taatgtacag 1140
aaccggaaaa tttatctcag taatgtatac acaccggtga ctgctaacat tctggacgat 1200
aacgtctacg atattcaaaa tggctttaat atcccgaaga gcaacttgaa tgtcctcttc 1260
atggggcaga acttgtcacg taacccagcg ctgcgaaaag ttaacccaga aaatatgttg 1320
tacctcttta caaaattctg tgtagacgcc attgacggac gctcactgta caacaaaacc 1380
ctgcaatgcc gtgaacttct ggttaagaac accgacctgc cgttcattgg ggacatcagt 1440
gatgtcaaaa cggatatttt tcttcggaag gatattaatg aggaaaccga agtgatatac 1500
tatcctgaca atgtgtcggt agatcaggta atcctgagta agaacaccag cgagcatggg 1560
cagctggatc tgttgtatcc gagcattgac agcgagtcgg aaatactgcc cggcgaaaat 1620
caagtttttt atgacaatcg gacccagaat gttgattatc tgaatagtta ctattacttg 1680
gagagccaaa aattatcaga taatgtggaa gactttacct ttacccggtc tatcgaagag 1740
gcgctggata acagcgcgaa agtttacact tattttccca cgctcgcaaa caaagttaat 1800
gctggcgtac agggtggatt atttcttatg tgggcgaatg atgtggtaga ggactttaca 1860
accaacatcc tgcgcaaaga cactttagac aaaatttctg acgtctcggc cattatcccg 1920
tatataggtc cggccttaaa cataagcaat tcggttcgcc gtggcaactt cacagaagcc 1980

```
ttcgctgtga ctggtgtgac cattctgttg gaagcatttc ctgagtttac gatcccggct   2040

ctgggcgcat ttgtaattta ctctaaagtt caggaacgaa atgaaattat aaaaactatc   2100

gataattgcc tggaacagcg tatcaagaga tggaaggatt cctatgagtg gatgatgggg   2160

acctggctgt caagaattat cacacagttt aataacatat cctatcaaat gtatgatagc   2220

ttaaactatc aagcaggagc gataaaggcg aaaattgacc tggaatacaa gaaatattct   2280

ggttcggata aagagaatat taaaagtcag gtggaaaatc tgaaaaatag tttagatgtc   2340

aaaatttctg aggcgatgaa taacattaac aaattcatcc gcgagtgcag tgtaacttat   2400

ttgtttaaga atatgttacc caaagttatc gacgaactga atgaatttga tcgtaatacc   2460

aaagccaaat tgatcaacct catcgactct cataacatca ttctggtggg agaagtcgac   2520

aaactgaaag ctaaggtgaa taacagcttc cagaatacaa ttccgtttaa tattttctca   2580

tacaccaata actcgctgct taaagatatt atcaacgaat attttaatct ggagggtggc   2640

ggtggcagtg gcggtggcgg atccggcggt ggcggtagcg cactggataa ttcagattcc   2700

gaatgtccac tgtcacacga tggttattgt cttcatgatg gcgtgtgcat gtatatagaa   2760

gcgttagata aatacgcttg caactgcgtg gttggctata tcggcgaacg ttgtcagtat   2820

cgtgatttaa agtggtggga attacgctaa tgaaagctt                          2859
```

<210> SEQ ID NO 20
<211> LENGTH: 948
<212> TYPE: PRT
<213> ORGANISM: Unknown
<220> FEATURE:
<223> OTHER INFORMATION: Protein sequence of the fully synthesised EGF-LHN/C fusion

<400> SEQUENCE: 20

```
Met Ile Ser Glu Phe Gly Ser Glu Phe Met Pro Ile Thr Ile Asn Asn
1               5                   10                  15

Phe Asn Tyr Ser Asp Pro Val Asp Asn Lys Asn Ile Leu Tyr Leu Asp
            20                  25                  30

Thr His Leu Asn Thr Leu Ala Asn Glu Pro Glu Lys Ala Phe Arg Ile
        35                  40                  45

Thr Gly Asn Ile Trp Val Ile Pro Asp Arg Phe Ser Arg Asn Ser Asn
    50                  55                  60

Pro Asn Leu Asn Lys Pro Pro Arg Val Thr Ser Pro Lys Ser Gly Tyr
65                  70                  75                  80

Tyr Asp Pro Asn Tyr Leu Ser Thr Asp Ser Asp Lys Asp Thr Phe Leu
                85                  90                  95

Lys Glu Ile Ile Lys Leu Phe Lys Arg Ile Asn Ser Arg Glu Ile Gly
            100                 105                 110

Glu Glu Leu Ile Tyr Arg Leu Ser Thr Asp Ile Pro Phe Pro Gly Asn
        115                 120                 125

Asn Asn Thr Pro Ile Asn Thr Phe Asp Phe Asp Val Asp Phe Asn Ser
    130                 135                 140

Val Asp Val Lys Thr Arg Gln Gly Asn Asn Trp Val Lys Thr Gly Ser
145                 150                 155                 160

Ile Asn Pro Ser Val Ile Ile Thr Gly Pro Arg Glu Asn Ile Ile Asp
                165                 170                 175

Pro Glu Thr Ser Thr Phe Lys Leu Thr Asn Asn Thr Phe Ala Ala Gln
            180                 185                 190

Glu Gly Phe Gly Ala Leu Ser Ile Ile Ser Ile Ser Pro Arg Phe Met
```

-continued

```
        195                 200                 205

Leu Thr Tyr Ser Asn Ala Thr Asn Asp Val Gly Glu Gly Arg Phe Ser
    210                 215                 220

Lys Ser Glu Phe Cys Met Asp Pro Ile Leu Ile Leu Met His Glu Leu
225                 230                 235                 240

Asn His Ala Met His Asn Leu Tyr Gly Ile Ala Ile Pro Asn Asp Gln
                245                 250                 255

Thr Ile Ser Ser Val Thr Ser Asn Ile Phe Tyr Ser Gln Tyr Asn Val
            260                 265                 270

Lys Leu Glu Tyr Ala Glu Ile Tyr Ala Phe Gly Gly Pro Thr Ile Asp
        275                 280                 285

Leu Ile Pro Lys Ser Ala Arg Lys Tyr Phe Glu Glu Lys Ala Leu Asp
    290                 295                 300

Tyr Tyr Arg Ser Ile Ala Lys Arg Leu Asn Ser Ile Thr Thr Ala Asn
305                 310                 315                 320

Pro Ser Ser Phe Asn Lys Tyr Ile Gly Glu Tyr Lys Gln Lys Leu Ile
                325                 330                 335

Arg Lys Tyr Arg Phe Val Val Glu Ser Ser Gly Glu Val Thr Val Asn
            340                 345                 350

Arg Asn Lys Phe Val Glu Leu Tyr Asn Glu Leu Thr Gln Ile Phe Thr
        355                 360                 365

Glu Phe Asn Tyr Ala Lys Ile Tyr Asn Val Gln Asn Arg Lys Ile Tyr
    370                 375                 380

Leu Ser Asn Val Tyr Thr Pro Val Thr Ala Asn Ile Leu Asp Asp Asn
385                 390                 395                 400

Val Tyr Asp Ile Gln Asn Gly Phe Asn Ile Pro Lys Ser Asn Leu Asn
                405                 410                 415

Val Leu Phe Met Gly Gln Asn Leu Ser Arg Asn Pro Ala Leu Arg Lys
            420                 425                 430

Val Asn Pro Glu Asn Met Leu Tyr Leu Phe Thr Lys Phe Cys Val Asp
        435                 440                 445

Ala Ile Asp Gly Arg Ser Leu Tyr Asn Lys Thr Leu Gln Cys Arg Glu
    450                 455                 460

Leu Leu Val Lys Asn Thr Asp Leu Pro Phe Ile Gly Asp Ile Ser Asp
465                 470                 475                 480

Val Lys Thr Asp Ile Phe Leu Arg Lys Asp Ile Asn Glu Glu Thr Glu
                485                 490                 495

Val Ile Tyr Tyr Pro Asp Asn Val Ser Val Asp Gln Val Ile Leu Ser
            500                 505                 510

Lys Asn Thr Ser Glu His Gly Gln Leu Asp Leu Leu Tyr Pro Ser Ile
        515                 520                 525

Asp Ser Glu Ser Glu Ile Leu Pro Gly Glu Asn Gln Val Phe Tyr Asp
    530                 535                 540

Asn Arg Thr Gln Asn Val Asp Tyr Leu Asn Ser Tyr Tyr Tyr Leu Glu
545                 550                 555                 560

Ser Gln Lys Leu Ser Asp Asn Val Glu Asp Phe Thr Phe Thr Arg Ser
                565                 570                 575

Ile Glu Glu Ala Leu Asp Asn Ser Ala Lys Val Tyr Thr Tyr Phe Pro
            580                 585                 590

Thr Leu Ala Asn Lys Val Asn Ala Gly Val Gln Gly Gly Leu Phe Leu
        595                 600                 605

Met Trp Ala Asn Asp Val Val Glu Asp Phe Thr Thr Asn Ile Leu Arg
    610                 615                 620
```

-continued

```
Lys Asp Thr Leu Asp Lys Ile Ser Asp Val Ser Ala Ile Ile Pro Tyr
625                 630                 635                 640

Ile Gly Pro Ala Leu Asn Ile Ser Asn Ser Val Arg Arg Gly Asn Phe
                645                 650                 655

Thr Glu Ala Phe Ala Val Thr Gly Val Thr Ile Leu Leu Glu Ala Phe
            660                 665                 670

Pro Glu Phe Thr Ile Pro Ala Leu Gly Ala Phe Val Ile Tyr Ser Lys
        675                 680                 685

Val Gln Glu Arg Asn Glu Ile Ile Lys Thr Ile Asp Asn Cys Leu Glu
    690                 695                 700

Gln Arg Ile Lys Arg Trp Lys Asp Ser Tyr Glu Trp Met Met Gly Thr
705                 710                 715                 720

Trp Leu Ser Arg Ile Ile Thr Gln Phe Asn Asn Ile Ser Tyr Gln Met
                725                 730                 735

Tyr Asp Ser Leu Asn Tyr Gln Ala Gly Ala Ile Lys Ala Lys Ile Asp
            740                 745                 750

Leu Glu Tyr Lys Lys Tyr Ser Gly Ser Asp Lys Glu Asn Ile Lys Ser
        755                 760                 765

Gln Val Glu Asn Leu Lys Asn Ser Leu Asp Val Lys Ile Ser Glu Ala
    770                 775                 780

Met Asn Asn Ile Asn Lys Phe Ile Arg Glu Cys Ser Val Thr Tyr Leu
785                 790                 795                 800

Phe Lys Asn Met Leu Pro Lys Val Ile Asp Glu Leu Asn Glu Phe Asp
                805                 810                 815

Arg Asn Thr Lys Ala Lys Leu Ile Asn Leu Ile Asp Ser His Asn Ile
            820                 825                 830

Ile Leu Val Gly Glu Val Asp Lys Leu Lys Ala Lys Val Asn Asn Ser
        835                 840                 845

Phe Gln Asn Thr Ile Pro Phe Asn Ile Phe Ser Tyr Thr Asn Asn Ser
    850                 855                 860

Leu Leu Lys Asp Ile Ile Asn Glu Tyr Phe Asn Leu Glu Gly Gly Gly
865                 870                 875                 880

Gly Ser Gly Gly Gly Gly Ser Gly Gly Gly Gly Ser Ala Leu Asp Asn
                885                 890                 895

Ser Asp Ser Glu Cys Pro Leu Ser His Asp Gly Tyr Cys Leu His Asp
            900                 905                 910

Gly Val Cys Met Tyr Ile Glu Ala Leu Asp Lys Tyr Ala Cys Asn Cys
        915                 920                 925

Val Val Gly Tyr Ile Gly Glu Arg Cys Gln Tyr Arg Asp Leu Lys Trp
    930                 935                 940

Trp Glu Leu Arg
945


<210> SEQ ID NO 21
<211> LENGTH: 23
<212> TYPE: PRT
<213> ORGANISM: Influenza virus

<400> SEQUENCE: 21

Gly Leu Phe Gly Ala Ile Ala Gly Phe Ile Glu Asn Gly Trp Glu Gly
1               5                   10                  15

Met Ile Asp Gly Trp Tyr Gly
            20
```

```
<210> SEQ ID NO 22
<211> LENGTH: 12
<212> TYPE: PRT
<213> ORGANISM: Unknown
<220> FEATURE:
<223> OTHER INFORMATION: Substance P peptide sequence

<400> SEQUENCE: 22

Arg Pro Lys Pro Gln Gln Phe Phe Gly Leu Met Cys
1               5                   10


<210> SEQ ID NO 23
<211> LENGTH: 12
<212> TYPE: PRT
<213> ORGANISM: Unknown
<220> FEATURE:
<223> OTHER INFORMATION: Substance P peptide sequence with N-terminal
      Cys

<400> SEQUENCE: 23

Cys Arg Pro Lys Pro Gln Gln Phe Phe Gly Leu Met
1               5                   10


<210> SEQ ID NO 24
<211> LENGTH: 4
<212> TYPE: PRT
<213> ORGANISM: Unknown
<220> FEATURE:
<223> OTHER INFORMATION: Factor Xa
<220> FEATURE:
<221> NAME/KEY: MISC_FEATURE
<222> LOCATION: (4)..(4)
<223> OTHER INFORMATION: Specific cleavable peptide bond

<400> SEQUENCE: 24

Ile Glu Gly Arg
1


<210> SEQ ID NO 25
<211> LENGTH: 5
<212> TYPE: PRT
<213> ORGANISM: Unknown
<220> FEATURE:
<223> OTHER INFORMATION: Enterokinase
<220> FEATURE:
<221> NAME/KEY: MISC_FEATURE
<222> LOCATION: (5)..(5)
<223> OTHER INFORMATION: specific cleavable peptide bond

<400> SEQUENCE: 25

Asp Asp Asp Asp Lys
1               5


<210> SEQ ID NO 26
<211> LENGTH: 8
<212> TYPE: PRT
<213> ORGANISM: Unknown
<220> FEATURE:
<223> OTHER INFORMATION: TEV protease
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (7)..(8)
<223> OTHER INFORMATION: specific cleavable peptide bond
```

<400> SEQUENCE: 26

Glu Xaa Xaa Tyr Xaa Gln Ser Gly
1 5

<210> SEQ ID NO 27
<211> LENGTH: 8
<212> TYPE: PRT
<213> ORGANISM: unknown
<220> FEATURE:
<223> OTHER INFORMATION: Precission
<220> FEATURE:
<221> NAME/KEY: MISC_FEATURE
<222> LOCATION: (6)..(7)
<223> OTHER INFORMATION: specific cleavable peptide bond

<400> SEQUENCE: 27

Leu Glu Val Leu Phe Gln Gly Pro
1 5

<210> SEQ ID NO 28
<211> LENGTH: 6
<212> TYPE: PRT
<213> ORGANISM: unknown
<220> FEATURE:
<223> OTHER INFORMATION: Thrombin
<220> FEATURE:
<221> NAME/KEY: MISC_FEATURE
<222> LOCATION: (4)..(5)
<223> OTHER INFORMATION: specific cleavable peptide bond

<400> SEQUENCE: 28

Leu Val Pro Arg Gly Ser
1 5

<210> SEQ ID NO 29
<211> LENGTH: 9
<212> TYPE: PRT
<213> ORGANISM: Unknown
<220> FEATURE:
<223> OTHER INFORMATION: Integrin binding peptide sequence

<400> SEQUENCE: 29

Gly Gly Arg Gly Asp Met Phe Gly Ala
1 5

<210> SEQ ID NO 30
<211> LENGTH: 11
<212> TYPE: PRT
<213> ORGANISM: Unknown
<220> FEATURE:
<223> OTHER INFORMATION: Integrin binding peptide sequence

<400> SEQUENCE: 30

Gly Gly Cys Arg Gly Asp Met Phe Gly Cys Ala
1 5 10

<210> SEQ ID NO 31
<211> LENGTH: 5
<212> TYPE: PRT
<213> ORGANISM: Unknown
<220> FEATURE:
<223> OTHER INFORMATION: cyclic RGD peptide
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MISC_FEATURE
<222> LOCATION: (5)..(5)
<223> OTHER INFORMATION: N-methyl-Val

<400> SEQUENCE: 31

Arg Gly Asp Phe Val
1               5

<210> SEQ ID NO 32
<211> LENGTH: 10
<212> TYPE: PRT
<213> ORGANISM: Unknown
<220> FEATURE:
<223> OTHER INFORMATION: linear integrin binding sequence

<400> SEQUENCE: 32

Pro Leu Ala Glu Ile Asp Gly Ile Glu Leu
1               5                   10

<210> SEQ ID NO 33
<211> LENGTH: 12
<212> TYPE: PRT
<213> ORGANISM: Unknown
<220> FEATURE:
<223> OTHER INFORMATION: cyclic integrin binding sequence

<400> SEQUENCE: 33

Cys Pro Leu Ala Glu Ile Asp Gly Ile Glu Leu Cys
1               5                   10

<210> SEQ ID NO 34
<211> LENGTH: 7
<212> TYPE: PRT
<213> ORGANISM: Unknown
<220> FEATURE:
<223> OTHER INFORMATION: vasoactive intestinal peptide

<400> SEQUENCE: 34

Thr His Ala Leu Trp His Thr
1               5

<210> SEQ ID NO 35
<211> LENGTH: 5
<212> TYPE: PRT
<213> ORGANISM: Unknown
<220> FEATURE:
<223> OTHER INFORMATION: integrin-binding protein

<400> SEQUENCE: 35

Arg Gly Asp Phe Val
1               5

<210> SEQ ID NO 36
<211> LENGTH: 4
<212> TYPE: PRT
<213> ORGANISM: Unknown
<220> FEATURE:
<223> OTHER INFORMATION: integrin-binding protein
<220> FEATURE:
<221> NAME/KEY: MOD_RES
<222> LOCATION: (4)..(4)
<223> OTHER INFORMATION: METHYLATION

<400> SEQUENCE: 36

Arg Gly Asp Val
1

<210> SEQ ID NO 37

<211> LENGTH: 6
<212> TYPE: PRT
<213> ORGANISM: Unknown
<220> FEATURE:
<223> OTHER INFORMATION: integrin-binding protein

<400> SEQUENCE: 37

Gly Arg Gly Asp Ser Pro
1               5

<210> SEQ ID NO 38
<211> LENGTH: 6
<212> TYPE: PRT
<213> ORGANISM: Unknown
<220> FEATURE:
<223> OTHER INFORMATION: integrin-binding protein

<400> SEQUENCE: 38

Gly Arg Gly Glu Ser Pro
1               5

<210> SEQ ID NO 39
<211> LENGTH: 4
<212> TYPE: PRT
<213> ORGANISM: Unknown
<220> FEATURE:
<223> OTHER INFORMATION: syntaxin domain

<400> SEQUENCE: 39

Ala Val Lys Tyr
1

<210> SEQ ID NO 40
<211> LENGTH: 7
<212> TYPE: PRT
<213> ORGANISM: Unknown
<220> FEATURE:
<223> OTHER INFORMATION: linker domain

<400> SEQUENCE: 40

Lys Ser Val Lys Ala Pro Gly
1               5

<210> SEQ ID NO 41
<211> LENGTH: 20
<212> TYPE: PRT
<213> ORGANISM: Unknown
<220> FEATURE:
<223> OTHER INFORMATION: protease cleavage site

<400> SEQUENCE: 41

Val Asp Glu Glu Lys Leu Tyr Asp Asp Asp Asp Lys Asp Arg Trp Gly
1               5                   10                  15

Ser Ser Leu Gln
            20

<210> SEQ ID NO 42
<211> LENGTH: 15
<212> TYPE: PRT
<213> ORGANISM: Unknown
<220> FEATURE:
<223> OTHER INFORMATION: inter-domain of linker

<400> SEQUENCE: 42

His Lys Ala Ile Asp Gly Arg Ser Leu Tyr Asn Lys Thr Leu Asp
1               5                   10                  15

-continued

```
<210> SEQ ID NO 43
<211> LENGTH: 23
<212> TYPE: PRT
<213> ORGANISM: Unknown
<220> FEATURE:
<223> OTHER INFORMATION: protease cleavage site

<400> SEQUENCE: 43

Val Asp Gly Ile Ile Thr Ser Lys Thr Lys Ser Asp Asp Asp Asp Lys
1               5                   10                  15

Asn Lys Ala Leu Asn Leu Gln
            20


<210> SEQ ID NO 44
<211> LENGTH: 7
<212> TYPE: PRT
<213> ORGANISM: Unknown
<220> FEATURE:
<223> OTHER INFORMATION: vasoactive intestinal peptide

<400> SEQUENCE: 44

Thr His Ala Leu His Trp Thr
1               5
```

TREATMENT OF MUCUS HYPERSECRETION

This application is a continuation-in-part of U.S. patent application Ser. No. 11/518,213, filed Sep. 11, 2006, which is a continuation of U.S. patent application Ser. No. 10/633,698, filed Aug. 5, 2003 now abandoned, which is a continuation-in-part of U.S. patent application Ser. No. 09/763,669, filed May 29, 2001, now U.S. Pat. No. 6,632,440, which is a national phase entry of PCT/GB99/02806, filed Aug. 25, 1999, which claims the benefit of priority of GB 9818548.1, filed Aug. 25, 1998. Each of these applications is hereby incorporated by reference in their entirety.

FIELD OF THE INVENTION

The present invention relates to treatment of mucus hypersecretion, to compositions therefor and manufacture of those compositions. The present invention relates particularly, though not exclusively, to the treatment of chronic bronchitis in chronic obstructive pulmonary disease (COPD), asthma and other clinical conditions involving COPD.

DESCRIPTION OF RELATED ART

Mucus is a thin film of protective viscoelastic liquid which lines the airways. It is a 1-2% aqueous solution, in which the major components are the glycoconjugates known as mucins. Mucus, including the mucins, is secreted by mucus secretory cells, the surface epithelial goblet cells of the large airways and the mucus cells of the submucosal glands. Mucin release occurs by three mechanisms: constitutive secretion, regulated secretion and protease cell surface activity. Of these it is regulated secretion that responds to external stimuli and is amenable to therapeutic intervention in COPD and asthma. Regulated secretion involves release from intracellular granules by docking and fusion of the granules with the cell exterior to release their contents onto the airway surface. Fusion of the granules can either be with the plasma membrane of the epithelial cell or with the membrane of other granules leading to release via multigranular complexes fused at the cell surface. Regulated secretion of mucins is controlled by humoral factors and by neural mechanisms. The neural mechanisms in humans involve a minor contribution from the adrenergic, sympathetic pathway and a major cholinergic, parasympathetic component. Another important neural pathway regulating mucin secretion, particularly the hypersecretion of pathological conditions, is that of the Non-Adrenergic Non-Cholinergic (NANC) pathway. The NANC component involves both an orthodromic pathway involving neuropeptide and nonpeptide transmitters, and a local sensory efferent pathway involving antidromic fibres from sensory C fibres.

COPD is a common respiratory condition, being the fourth most common cause of death in middle age in the Western world. COPD comprises two related diseases, which usually occur together, emphysema and chronic bronchitis. The pathological basis of chronic bronchitis is mucus hypersecretion. The excessive, chronic bronchial secretion results in expectoration, and can last from a few days to many years. The mucus hypersecretion of COPD results in small airway obstruction producing reduced maximal respiratory flow and slow forced lung emptying. There is minimal reversal of the impaired airway function of COPD by bronchodilators and currently no effective therapy for the mucus hypersecretion.

Mucus hypersecretion is also a significant contributing factor to the pathophysiology of asthma. It is a key component in status asthmaticus, and contributes to the chronic symptoms and morbidity of asthma. The mucus hypersecretion component of asthma is not well controlled by current therapies, particularly in severe and chronic cases.

It would accordingly be desirable to treat, reduce or prevent the mucus hypersecretion that causes or leads to these disease conditions.

SUMMARY OF THE INVENTION

Accordingly, the invention provides a method of treating mucus hypersecretion comprising inhibiting mucus secretion by mucus secreting cells and/or inhibiting neurotransmitter release from neuronal cells that control or direct mucus secretion. The invention further provides, in a second aspect, a compound, for use in the treatment of mucus hypersecretion, which inhibits mucus secretion by (i) inhibiting mucus secretion by mucus secreting cells, or (ii) inhibiting neurotransmitter release from neuronal cells controlling or directing mucus secretion.

An advantage of the invention is that an agent for effective treatment of mucus hypersecretion and associated disease states is now provided and used, offering a relief to sufferers where hitherto there was no such agent available.

The present invention thus represents a new different approach to treatment of mucus hypersecretion by inhibiting secretory processes, namely one or other or both of the mucus secretion by mucus secretory cells and the secretion of neurotransmitters regulating mucus secretion. Agents of the present invention reduce mucus secretion and/or prevent the hypersecretion of COPD and asthma, and any other disease in which mucus hypersecretion is a causative element.

DETAILED DESCRIPTION OF THE INVENTION

A compound of the invention typically inhibits exocytosis in mucus secreting cells or neurones that control or direct mucus secretion. This compound is administered to a patient suffering from mucus hypersecretion and inhibition of exocytosis in the cells specified results in reduction of secretion of mucus. Specific disease states caused by or exacerbated by hypersecretion are localised to the airways, and hence an embodiment of the invention comprises topical administration to the airways or to a selected region or to a selected portion of the airways of a compound that inhibits exocytosis in mucus secreting cells or in neurones that control or direct mucus secretion.

A compound of embodiments of the invention is a polypeptide that consists of or comprises an inhibiting domain which inhibits exocytosis in the mucus secreting cell or inhibits exocytosis in a neuronal cell, thereby directly inhibiting exocytosis of mucus or one or more mucus components or indirectly inhibiting mucus secretion by inhibiting exocytosis of neurotransmitter which would in turn lead to or otherwise stimulate mucus secretion. The inhibiting domain can suitably comprise a light chain of a clostridial neurotoxin, or a fragment or variant thereof which inhibits exocytosis.

The compound preferably further comprises a translocating domain that translocates the inhibiting domain into the cell. This domain may comprise a $H_N$ region of a botulinum polypeptide, or a fragment or variant thereof that translocates the inhibiting domain into the cell.

The compound preferably comprises a targeting domain which binds to (i) a mucus secreting cell, or (ii) a neuronal cell controlling or directing mucus secretion. The compound is thus rendered specific for these cell types. It is also optional for the compound to be relatively non-specific but for inhibition of mucus secretion to be achieved via targeting of the compound through choice of route of administration—the compound is hence preferably administered to mucus secreting epithelial cells in the airways, specifically in the lungs. Whilst a non-specific compound of the invention may affect exocytosis in many cells of a wide range of types, generally only those cells that are stimulated will be affected and these stimulated cells will in typical disease states be those that are secreting mucus and contributing to disease.

When present, suitable targeting domains include, but are not restricted to, a domain selected from Substance P, VIP, beta-2-adrenoreceptor agonists, gastrin releasing peptide and calcitonin gene related peptide. The precise cells targeted in preferred embodiments of the invention are selected from (a) cells that secrete mucins, such as epithelial goblet cells and submucosal gland mucus secreting cells, (b) cells that secrete aqueous components of mucus, such as Clara cells and serous cells, and (c) cells that control or direct mucus secretion, such as "sensory-efferent" C-fibres, or NANC neural system fibres. The compound may be administered as a substantially pure preparation all targeted to the same cell type, or may be a mixture of compounds targeted respectively to different cells.

The compound of specific embodiments of the invention comprises first, second and third domains. The first domain is adapted to cleave one or more vesicle or plasma-membrane associated proteins essential to exocytosis. This domain prevents exocytosis once delivered to a targeted cell. The second domain translocates the compound into the cell. This domain delivers the first domain into the cell. The third domain binds to the target cell, ie binds to (i) a mucus secreting cell, or (ii) a neuronal cell controlling or directing mucus secretion, and may be referred to as a targeting moiety ("TM"). The compound may be derived from a toxin and it is preferred that such a compound is free of clostridial neurotoxin and free of any clostridial neurotoxin precursor that can be converted into toxin. Botulinum and tetanus toxin are suitable sources of domains for the compounds of the invention.

In use, the agent of specific embodiments of the invention has a number of discrete functions. It binds to a surface structure (the Binding Site {BS}) which is characteristic of, and has a degree of specificity for, the relevant secretory cells and or neurones in the airways responsible for secretion of mucus and or regulation of said secretion. It enters the cell to which it binds by a process of endocytosis. Only certain cell surface BSs can undergo endocytosis, and preferably the BS to which the agent binds is one of these. The agent enters the cytosol, and modifies components of the exocytotic machinery present in the relevant secretory cells and or neurones in the airways responsible for secretion of mucus and or regulation of said secretion.

Surprisingly, agents of the present invention for treatment of mucus hypersecretion can be produced by modifying a clostridial neurotoxin or fragment thereof. The clostridial neurotoxins share a common architecture of a catalytic L-chain (LC, ca 50 kDa) disulphide linked to a receptor binding and translocating H-chain ($H_C$, ca 100 kDa). The $H_C$ polypeptide is considered to comprise all or part of two distinct functional domains. The carboxy-terminal half of the $H_C$ (ca 50 kDa), termed the $H_C$ domain, is involved in the high affinity, neurospecific binding of the neurotoxin to cell surface receptors on the target neuron, whilst the amino-terminal half, termed the $H_N$ domain (ca 50 kDa), is considered to mediate the translocation of at least some portion of the neurotoxin across cellular membranes such that the functional activity of the LC is expressed within the target cell. The $H_N$ domain also has the property, under conditions of low pH, of forming ion-permeable channels in lipid membranes, this may in some manner relate to its translocation function.

For botulinum neurotoxin type A (BoNT/A) these domains are considered to reside within amino acid residues 872-1296 for the Hc, amino acid residues 449-871 for the $H_N$ and residues 1-448 for the LC. Digestion with trypsin effectively degrades the Hc domain of the BoNT/A to generate a non-toxic fragment designated $LH_N$, which is no longer able to bind to and enter neurons. The $LH_N$ fragment so produced also has the property of enhanced solubility compared to both the parent holotoxin and the isolated LC.

It is therefore possible to provide functional definitions of the domains within the neurotoxin molecule, as follows:

(A) clostridial neurotoxin light chain:

A metalloprotease exhibiting high substrate specificity for vesicle and/or plasma membrane associated proteins involved in the exocytotic process. In particular, it cleaves one or more of SNAP-25, VAMP P (synaptobrevin/cellubrevin) and syntaxin.

(B) clostridial neurotoxin heavy chain $H_N$ domain:

A portion of the heavy chain which enables translocation of that portion of the neurotoxin molecule such that a functional expression of light chain activity occurs within a target cell.

The domain responsible for translocation of the endopeptidase activity, following binding of neurotoxin to its specific cell surface receptor via the binding domain, into the target cell.

The domain responsible for formation of ion-permeable pores in lipid membranes under conditions of low pH.

The domain responsible for increasing the solubility of the entire polypeptide compared to the solubility of light chain alone.

(C) clostridial neurotoxin heavy chain $H_C$ domain:

A portion of the heavy chain which is responsible for binding of the native holotoxin to cell surface receptor(s) involved in the intoxicating action of clostridial toxin prior to internalisation of the toxin into the cell.

The identity of the cellular recognition markers for these toxins is currently not understood and no specific receptor species have yet been identified although Kozaki et al. have reported that synaptotagmin may be the receptor for botulinum neurotoxin type B. It is probable that each of the neurotoxins has a different receptor.

By covalently linking a clostridial neurotoxin, or a hybrid of two clostridial neurotoxins, in which the Hc region of the H-chain has been removed or modified, to a new molecule or moiety, the Targeting Moiety (TM), that binds to a BS on the surface of the relevant secretory cells and or neurones in the airways responsible for secretion of mucus and or regulation of said secretion, a novel agent capable of inhibiting mucus secretion is produced. A further surprising aspect of the present invention is that if the L-chain of a clostridial neurotoxin, or a fragment of the L-chain containing the endopeptidase activity, is covalently linked to TM which can also effect internalisation of the L-chain, or a fragment of the L-chain containing the endopeptidase activity, into the cytoplasm of the relevant secretory cells and or neurones in the airways responsible for secretion of mucus and or regulation of said secretion, this also produces a novel agent capable of inhibiting mucus secretion.

Accordingly, the invention may thus provide a compound containing a first domain equivalent to a clostridial toxin light chain and a second domain providing the functional aspects of the $H_N$ of a clostridial toxin heavy chain, whilst lacking the functional aspects of a clostridial toxin $H_C$ domain, and a third domain which binds to the target mucus secreting or mucus secretion controlling cell.

For the purposes of the invention, the functional property or properties of the $H_N$ of a clostridial toxin heavy chain that are to be exhibited by the second domain of the polypeptide of the invention is translocation of the first domain into a target cell once the compound is proximal to the target cell. References hereafter to a $H_N$ domain or to the functions of a $H_N$ domain are references to this property or properties. The second domain is not required to exhibit other properties of the $H_N$ domain of a clostridial toxin heavy chain. A second domain of the invention can thus be relatively insoluble but retain the translocation function of a native toxin—this is of use if solubility is not essential to its administration or if necessary solubility is imparted to a composition made up of that domain and one or more other components by one or more of said other components.

The translocating domain may be obtained from a microbial protein source, in particular from a bacterial or viral protein source. It is well documented that certain domains of bacterial toxin molecules are capable of forming such pores. It is also known that certain translocation domains of virally expressed membrane fusion proteins are capable of forming such pores. Such domains may be employed in the present invention.

Hence, in one embodiment, the translocating domain is a translocating domain of an enzyme, such as a bacterial or viral toxin. One such molecule is the heavy chain of a clostridial neurotoxin, for example botulinum neurotoxin type A. Other sources of bacterial toxin translocating domains include diphtheria toxin and domain II of *pseudomonas* exotoxin.

Other sources of translocating domains include certain translocating domains of virally expressed membrane fusion proteins. For example, Wagner et al. (1992) and Murata et al. (1992) describe the translocation (i.e. membrane fusion and vesiculation) function of a number of fusogenic and amphiphilic peptides derived from the N-terminal region of influenza virus haemagglutinin. Other virally expressed membrane fusion proteins known to have the desired translocating activity are a translocating domain of a fusogenic peptide of Semliki Forest Virus (SFV), a translocating domain of vesicular stomatitis virus (VSV) glycoprotein G, a translocating domain of SER virus F protein and a translocating domain of Foamy virus envelope glycoprotein. Virally encoded “spike proteins” have particular application in the context of the present invention, for example, the E1 protein of SFV and the G protein of the G protein of VSV.

Preferably it has been found to use only those portions of the protein molecule capable of pore-formation within the endosomal membrane.

Methodology to enable assessment of membrane fusion and thus identification of translocation domains suitable for use in the present invention are provided by Methods in Enzymology Vol 220 and 221, Membrane Fusion Techniques, Parts A and B, Academic Press 1993.

Examples of preferred translocating domains for use in the present invention are listed in the table below. The below-listed citations are all herein incorporated by reference.

| Translocation domain source | Amino acid residues | References |
|---|---|---|
| Diphtheria toxin | 194-380 | Silverman et al., 1994, J. Biol. Chem. 269, 22524-22532 |

-continued

| Translocation domain source | Amino acid residues | References |
|---|---|---|
| | | London E., 1992, Biochem. Biophys. Acta., 1113, 25-51 |
| Domain II of *pseudomonas* exotoxin | 405-613 | Prior et al., 1992, Biochemistry 31, 3555-3559<br>Kihara & Pastan, 1994, Bioconj Chem. 5, 532-538 |
| Influenza virus haemagglutinin | GLFGAIAGFIENGW EGMIDGWYG (SEQ ID NO: 1), and variants thereof | Plank et al., 1994, J. Biol. Chem. 269, 12918-12924<br>Wagner et al., 1992, PNAS, 89, 7934-7938<br>Murata et al., 1992, Biochemistry 31, 1986-1992 |
| Semliki Forest virus fusogenic protein | Translocation domain | Kielian et al., 1996, J Cell Biol. 134(4), 863-872 |
| Vesicular Stomatitis virus glycoprotein G | 118-139 | Yao et al., 2003, Virology 310(2), 319-332 |
| SER virus F protein | Translocation domain | Seth et al., 2003, J Virol 77(11) 6520-6527 |
| Foamy virus envelope glyoprotein | Translocation domain | Picard-Maureau et al., 2003, J Virol. 77(8), 4722-4730 |

Use of the translocating domains listed in the above table includes use of sequence variants thereof. A variant may comprise one or more conservative nucleic acid substitutions and/or nucleic acid deletions or insertions, with the proviso that the variant possesses the requisite translocating function. A variant may also comprise one or more amino acid substitutions and/or amino acid deletions or insertions, so long as the variant possesses the requisite translocating function.

The only functional requirement of the translocating domain is that it is capable of forming appropriate pores in the endosomal membrane. A number of routine methods are available for confirming that a particular translocating domain has the requisite translocating activity, and thus to determine the presence of a translocating domain. Shone et al. (1987), and Blaustein et al. (1987) provide details of two very simple assays to confirm that any particular bacterial translocating domain has the requisite translocating activity. Shone (1987) describes a simple in vitro assay employing liposomes, which are challenged with a test molecule. The presence of a molecule having the requisite translocating function is confirmed by release from the liposomes of K+ and/or labelled AND. Blaustein (1987) describes a simple in vitro assay employing planar phospholipid bilayer membranes, which are challenged with a test molecule. The presence of a molecule having the requisite translocation function is confirmed by an increase in conductance across the phospholipid membrane.

The polypeptide of the invention may be obtained by expression of a recombinant nucleic acid, preferably a DNA, and is a single polypeptide, that is to say not cleaved into separate light and heavy chain domains. The polypeptide is thus available in convenient and large quantities using recombinant techniques.

The first domain optionally comprises a fragment or variant of a clostridial toxin light chain. The fragment is optionally an N-terminal, or C-terminal fragment of the light chain, or is an internal fragment, so long as it substantially retains the ability to cleave the vesicle or plasma-membrane associated protein essential to exocytosis. Domains necessary for the activity of the light chain of clostridial toxins are described in J. Biol. Chem., Vol. 267, No. 21, July 1992, pages 14721-14729. The variant has a different peptide sequence from the light chain or from the fragment, though it too is capable of cleaving the vesicle or plasma-membrane associated protein. It is conveniently obtained by insertion, deletion and/or substitution of a light chain or fragment thereof. In embodiments of the invention described below a variant sequence comprises (i) an N-terminal extension to a clostridial toxin light chain or fragment (ii) a clostridial toxin light chain or fragment modified by alteration of at least one amino acid (iii) a C-terminal extension to a clostridial toxin light chain or fragment, or (iv) combinations of 2 or more of (i)-(iii).

In an embodiment of the invention described in an example below, the toxin light chain and the portion of the toxin heavy chain are of botulinum toxin type A. In a further embodiment of the invention described in an example below, the toxin light chain and the portion of the toxin heavy chain are of botulinum toxin type B. The polypeptide optionally comprises a light chain or fragment or variant of one toxin type and a heavy chain or fragment or variant of another toxin type.

In a polypeptide according to the invention said second domain preferably comprises a clostridial toxin heavy chain $H_N$ portion or a fragment or variant of a clostridial toxin heavy chain $H_N$ portion. The fragment is optionally an N-terminal or C-terminal or internal fragment, so long as it retains the function of the $H_N$ domain. Teachings of regions within the $H_N$ responsible for its function are provided for example in Biochemistry 1995, 34, pages 15175-15181 and Eur. J. Biochem, 1989, 185, pages 197-203. The variant has a different sequence from the $H_N$ domain or fragment, though it too retains the function of the $H_N$ domain. It is conveniently obtained by insertion, deletion and/or substitution of a $H_N$ domain or fragment thereof. In embodiments of the invention, described below, it comprises (i) an N-terminal extension to a $H_N$ domain or fragment, (ii) a C-terminal extension to a $H_N$ domain or fragment, (iii) a modification to a $H_N$ domain or fragment by alteration of at least one amino acid, or (iv) combinations of 2 or more of (i)-(iii). The clostridial toxin is preferably botulinum toxin or tetanus toxin.

These polypeptides of the invention thus typically contain two or more polypeptide first and second domain, linked by di-sulphide bridges into composite molecules, and further linked to a third domain.

The TM provides specificity for the BS on the relevant neuronal and or secretory cells responsible for secretion of mucus in the airways. The TM component of the agent can comprise one of many cell binding molecules, including, but not limited to, antibodies, monoclonal antibodies, antibody fragments (Fab, F(ab)'2, Fv, ScFv, etc.), lectins, hormones, cytokines, growth factors or peptides.

It is known in the art that the Hc portion of the neurotoxin molecule can be removed from the other portion of the H-chain, known as $H_N$, such that the $H_N$ fragment remains disulphide linked to the L-chain of the neurotoxin providing a fragment known as $LH_N$. Thus, in one embodiment of the present invention the $LH_N$ fragment of a clostridial neurotoxin is covalently linked, using linkages which may include one or more spacer regions, to a TM.

The $H_C$ domain of a clostridial neurotoxin may be mutated or modified, eg by chemical modification, to reduce or preferably incapacitate its ability to bind the neurotoxin to receptors at the neuromuscular junction. This modified clostridial neurotoxin is then covalently linked, using linkages which may include one or more spacer regions, to a TM.

The heavy chain of a clostridial neurotoxin, in which the $H_C$ domain is mutated or modified, eg by chemical modification, to reduce or preferably incapacitate its ability to bind the neurotoxin to receptors at the neuromuscular junction, may be combined with the L-chain of a different clostridial neurotoxin. This hybrid, modified clostridial neurotoxin is then covalently linked, using linkages which may include one or more spacer regions, to a TM.

In another embodiment of the invention, the $H_N$ domain of a clostridial neurotoxin is combined with the L-chain of a different clostridial neurotoxin. This hybrid $LH_N$ is then covalently linked, using linkages which may include one or more spacer regions, to a TM. In a further embodiment of the invention, the light chain of a clostridial neurotoxin, or a fragment of the light chain containing the endopeptidase activity, is covalently linked, using linkages which may include one or more spacer regions, to a TM which can also effect the internalisation of the L-chain, or a fragment of the L-chain containing the endopeptidase activity, into the cytoplasm of the relevant secretory and/or neuronal cells in the airways responsible for secretion of mucus and or regulation of said secretion.

The agent is optionally expressed recombinantly as a fusion protein which includes an appropriate TM in addition to any desired spacer regions. The recombinantly expressed agent may be derived wholly from the gene encoding one serotype of neurotoxin or may be a chimaera derived from genes encoding one or more serotypes. In another embodiment of the invention the required $LH_N$, which may be a hybrid of an L and $H_N$ from different clostridial types, is expressed recombinantly as a fusion protein with the TM, and may include one or more spacer regions.

The light chain of a clostridial neurotoxin, or a fragment of the light chain containing the endopeptidase activity, may be expressed recombinantly as a fusion protein with a TM which can also effect the internalisation of the L-chain, or a fragment of the L-chain containing the endopeptidase activity, into the cytoplasm of the relevant secretory and or neuronal cells in the airways responsible for secretion of mucus and or regulation of said secretion. The expressed fusion protein may also include one or more spacer regions.

A neurotoxin fragment as described in the present invention can be prepared by methods well known in the protein art, including, but not limited to, proteolytic cleavage or by genetic engineering strategies. Said fragment is preferably a non-toxic fragment. The conjugation may be chemical in nature using chemical or covalent linkers. Conjugates according to the present invention may be prepared by conventional methods known in the art.

According to a preferred embodiment of the present invention, the TM is a growth factor, preferably an epidermal growth factor (EGF), vascular endothelial growth factor, platelet-derived growth factor, keratinocyte growth factor, hepatocyte growth factor, transforming growth factor alpha, transforming growth factor beta. Additional preferred TMs include atrial natriuretic peptide, vasoactive intestinal peptide and THALW(H)T (SEQ ID NO: 34).

According to another preferred embodiment of the present invention, the TM is a peptide or protein that binds to a serous cell. A preferred example of such a TM is an integrin-binding protein.

Integrins are obligate heterodimer transmembrane proteins containing two distinct chains α (alpha) and β (beta) subunits. In mammals, 19 alpha and 8 beta subunits have been characterised—see Humphries, M. J. (2000), Integrin structure. Biochem Soc Trans. 28: 311-339, which is herein incorporated by reference thereto. Integrin subunits span through the plasma membrane, and in general have very short cytoplasmic domains of about 40-70 amino acids. Outside the cell plasma membrane, the alpha and beta chains lie close together along a length of about 23 nm, the final 5 nm NH$_2$-termini of each chain forming a ligand-binding region to which an agent of the present invention binds.

Preferred integrin-binding proteins of the present invention comprise the amino sequence Arg-Gly-Asp ("RGD"), which binds to the above-described ligand-binding region—see Craig. D et al. (2004), Structural insights into how the MIDAS ion stabilizes integrin binding to an RGD peptide under force. Structure, vol. 12, pp 2049-2058, which is herein incorporated by reference thereto.

In one embodiment, the integrin-binding protein TMs of the present invention have an amino acid length of between 3 and 100, preferably between 3 and 50, more preferably between 5 and 25, and particularly preferably between 5 and 15 amino acid residues.

The TMs of the present invention may form linear or cyclic structures.

Preferred integrin-binding TMs of the present invention include actin, alpha-actinin, focal contact adhesion kinase, paxillin, talin, RACK1, collagen, laminin, fibrinogen, heparin, phytohaemagglutinin, fibronectin, vitronectin, VCAM-1, ICAM-1, ICAM-2 and serum protein. Many integrins recognise the triple Arg-Gly-Asp (RGD) peptide sequence (Ruoslahti, 1996). The RGD motif is found in over 100 proteins including fibronectin, tenascin, fibrinogen and vitronectin. The RGD-integrin interaction is exploited as a conserved mechanism of cell entry by many pathogens including coxsackievirus (Roivaninen et al., 1991) and adenovirus (Mathias et al., 1994).

Additionally preferred integrin-binding TMs of the present invention include proteins selected from the following sequences: Arg-Gly-Asp-Phe-Val (SEQ ID NO: 35); Arg-Gly-Asp-{D-Phe}-{N-methyl-Val} (SEQ ID NO: 31); RGDFV (SEQ ID NO: 35); RGDfNMeV (SEQ ID NO: 31); GGRGDMFGA (SEQ ID NO: 29); GGCRGDMFGCA (SEQ ID NO: 30); GRGDSP (SEQ ID NO: 37); GRGESP (SEQ ID NO: 38); PLAEIDGIEL (SEQ ID NO: 32) and CPLAEIDGIELC (SEQ ID NO: 33). Reference to the above sequences embraces linear and cyclic forms, together with peptides exhibiting at least 80%, 85%, 90%, 95%, 98%, 99% sequence identity with said sequences. All of said TMs preferably retain the "RGD" tri-peptide sequence.

In a third aspect, the invention provides a composition for use in treating mucus hypersecretion, comprising:
a compound according to any of the second aspect of the invention; and
at least one of a pharmaceutically acceptable excipient, adjuvant and/or propellant, wherein the composition is for administration to the airways of a patient.

Aerosol administration is a preferred route of administration, though the present invention encompasses also any administration that delivers the compound to epithelia in the airways. Nasal administration is optional though buccal is preferred. The compound may thus be formulated for oral administration via aerosol or nebuliser or as a dry powder for inhalation using conventional excipients, adjuvants and/or propellants. The invention therefore further provides a pharmaceutical composition comprising a compound of the invention and a pharmaceutically acceptable carrier.

In use the compound will generally be employed in a pharmaceutical composition in association with a human pharmaceutical carrier, diluent and/or excipient, although the exact form of the composition will depend on the mode of administration. The compound may, for example, be employed in the form of an aerosol or nebulisable solution.

In a specific embodiment of the invention, described in further detail below, a polypeptide according to the invention comprises Substance P, and an L chain and a heavy chain H$_N$ region of botulinum toxin A. In use, this may be administered to a patient by aerosol. A solution of the polypeptide is prepared and converted into an aerosol using a nebuliser for inhalation into the lungs of nebulised particles of diameter 1-5 microns.

The dosage ranges for administration of the compounds of the present invention are those to produce the desired therapeutic effect. It will be appreciated that the dosage range required depends on the precise nature of the conjugate, the route of administration, the nature of the formulation, the age of the patient, the nature, extent or severity of the patient's condition, contraindications, if any, and the judgement of the attending physician. Wide variations in the required dosage, however, are to be expected depending on the precise nature of the conjugate. Variations in these dosage levels can be adjusted using standard empirical routines for optimisation, as is well understood in the art.

Fluid unit dosage forms are prepared utilising the compound and a pyrogen-free sterile vehicle. The compound, depending on the vehicle and concentration used, can be either dissolved or suspended in the vehicle. In preparing solutions the compound can be dissolved in the vehicle, the solution being made isotonic if necessary by addition of sodium chloride and sterilised by filtration through a sterile filter using aseptic techniques before filling into suitable sterile vials or ampoules and sealing. Alternatively, if solution stability is adequate, the solution in its sealed containers maybe sterilised by autoclaving. Advantageously additives such as buffering, solubilising, stabilising, preservative or bactericidal, suspending or emulsifying agents and/or local anaesthetic agents may be dissolved in the vehicle.

Dry powders which are dissolved or suspended in a suitable vehicle prior to use may be prepared by filling pre-sterilised drug substance and other ingredients into a sterile container using aseptic technique in a sterile area. Alternatively the drug and other ingredients may be dissolved into suitable containers using aseptic technique in a sterile area. The product is then freeze dried and the containers are sealed aseptically.

Compositions suitable for administration via the respiratory tract include aerosols, nebulisable solutions or microfine powders for insufflation. In the latter case, particle size of less than 50 microns, especially less than 10 microns, is preferred. Such compositions may be made up in a conventional manner and employed in conjunction with conventional administration devices.

In further aspects of the invention, there is provided use of a compound that inhibits exocytosis in mucus secreting cells or neurones that control or direct mucus secretion in manufacture of a medicament for treating mucus hypersecretion, asthma or COPD.

The invention yet further provides a method of manufacture of a pharmaceutical composition, comprising: obtaining a clostridial neurotoxin and modifying it so as to remove or disable its Hc portion; or obtaining a clostridial neurotoxin the Hc portion of which has been removed or disabled; linking the toxin with a targeting moiety that binds to (i) a mucus secreting cell, or (ii) a neuronal cell that controls or directs mucus secretion. The invention still further provides a method of manufacture of a pharmaceutical composition, comprising obtaining a first component having the domains: an inhibiting domain which inhibits exocytosis in a mucus secreting cell or neuronal cell that controls or directs mucus secretion; a translocating domain which translocates the inhibiting domain into the cell; and linking the first component to a second component that binds to (i) a mucus secreting cell, or (ii) a neuronal cell that controls or directs mucus secretion.

The first and second components are preferably formulated in an orally administrable composition in combination with one or more or an excipient, an adjuvant and a propellant.

BRIEF DESCRIPTION OF THE DRAWINGS

Specific embodiments of the invention are now illustrated in the following examples with reference to the accompanying drawings in which.

C=control (cell culture medium only)

VC=vehicle control (50 mM Hepes, 200 mM NaCl—eluant solution for the EGF-$LH_N$/C)

***$p<0.01$ vs C,

$p<0.001$ vs Stim.

Figure 15:
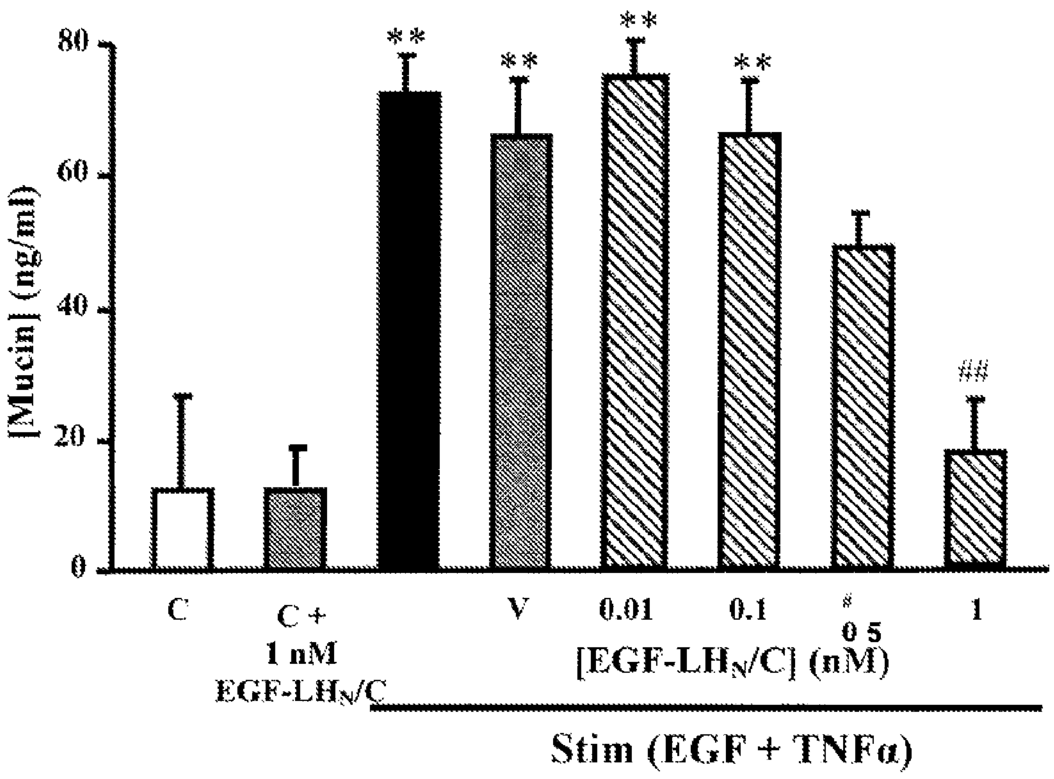

FIG. 15 shows effect of EGF-$LH_N$/C on EGF/TNF alpha-induced mucin secretion in NCI-H292 cells. Each concentration was assessed in triplicate and the figure is representative of four experiments. NCI-H292 cells were treated with the fusion or vehicle or medium alone for 48 hr followed by a 24 hr stimulation of the cells with EGF/TNF alpha (Stim) in the presence of the fusion. Vehicle treated cells received fresh vehicle plus medium only. Media was collected and assayed for mucin content using the ELLA method with a human mucin standard curve. All mucin levels are shown in ng/ml calculated from the human mucin standard curve within each ELLA plate. Each concentration was assessed in triplicate and the figure is representative of at least three experiments. N=3

C=control (cell culture medium only)

VC=vehicle control (50 mM Hepes, 200 mM NaCl—eluant solution for the EGF-$LH_N$/C)

** $p<0.01$ vs C, ## $p<0.01$ vs S

Figure 16:
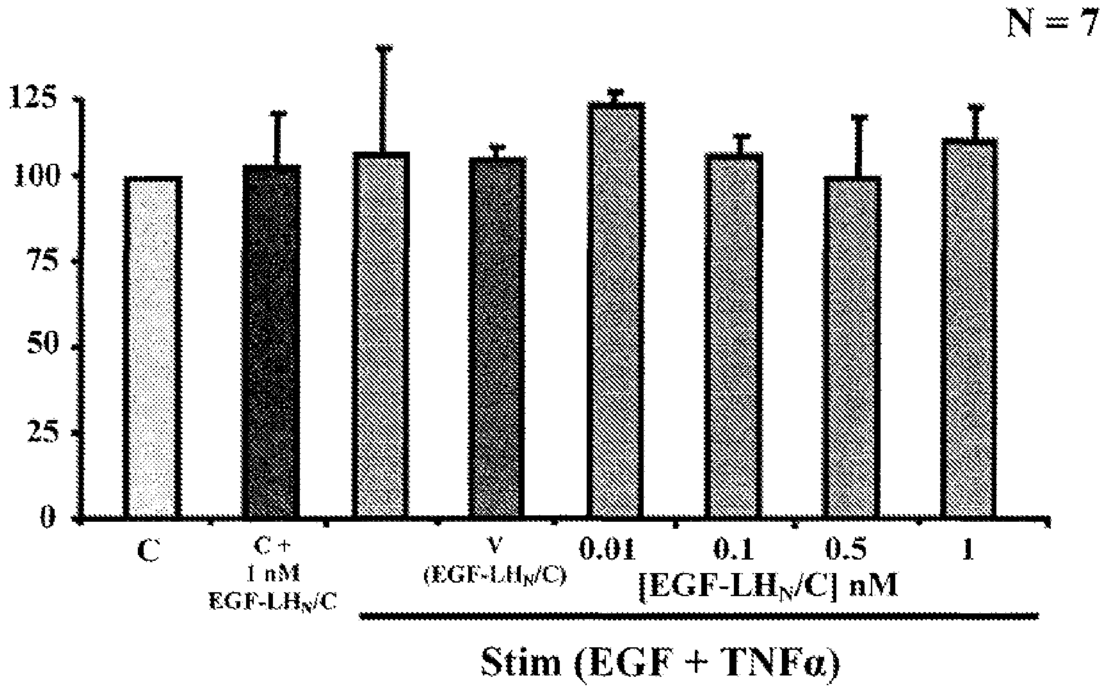
Figure 17:
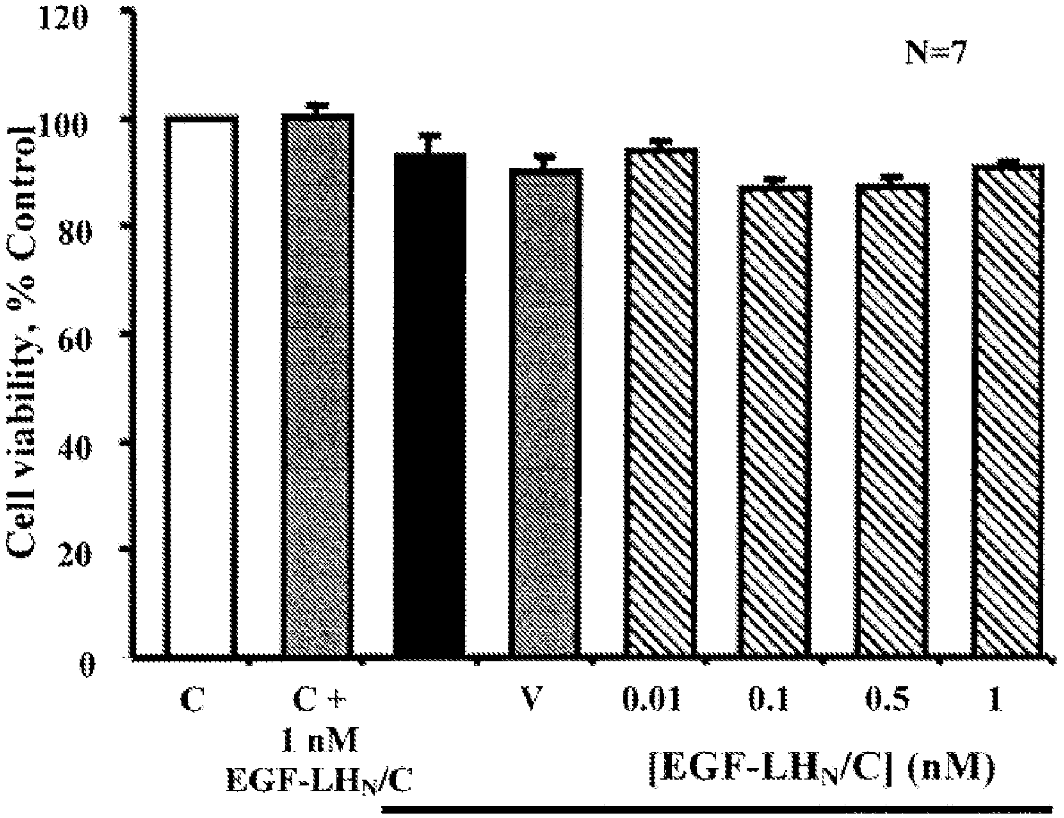

FIGS. 16 and 17 show effect of EGF-$LH_N$/C on viability of A549 cells and of H292 cells, respectively. Cells were pre-incubated with EGF-$LH_N$/C for 48 h, followed by 24 h stimulation with EGF/TNFα in the continued presence of EGF-$LH_N$/C and viability assessed by MTT assay. Data are mean cell viability as % control (bars=SEM) of 7 independent experiments. C=control. V=highest concentration of vehicle for EGF-$LH_N$/C. No significant differences were found.

Figure 18:
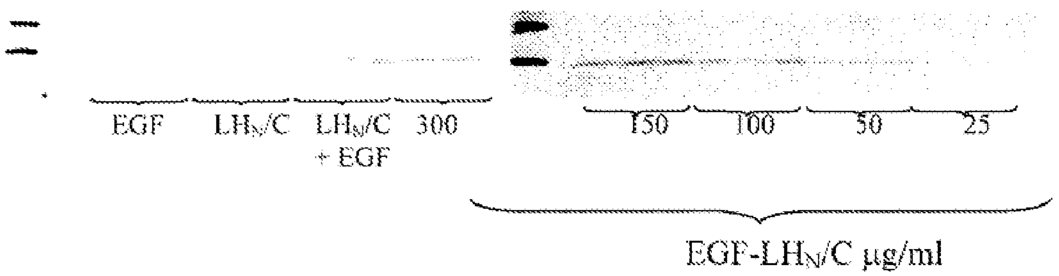

FIG. 18 shows Syntaxin cleavage in NCI-H292 cells by EGF-$LH_N$/C. Syntaxin cleavage in NCI-H292 cells by recombinant EGF-$LH_N$/C. Protein from cells treated for three days with the construct was analysed by Western blot. The Western blot shows the dose-dependent appearance of the cleavage product of syntaxin due to increasing concentrations of EGF-$LH_N$/C. The blot was probed using a polyclonal antibody raised to the AVKY (SEQ ID NO: 39) sequence at the BoNT/C cleavage site in syntaxin. $LH_N$/C alone or with EGF as not internalised in sufficient quantities to cause detectable cleavage of syntaxin. EGF alone did not cause cleavage of syntaxin.

Figure 19:
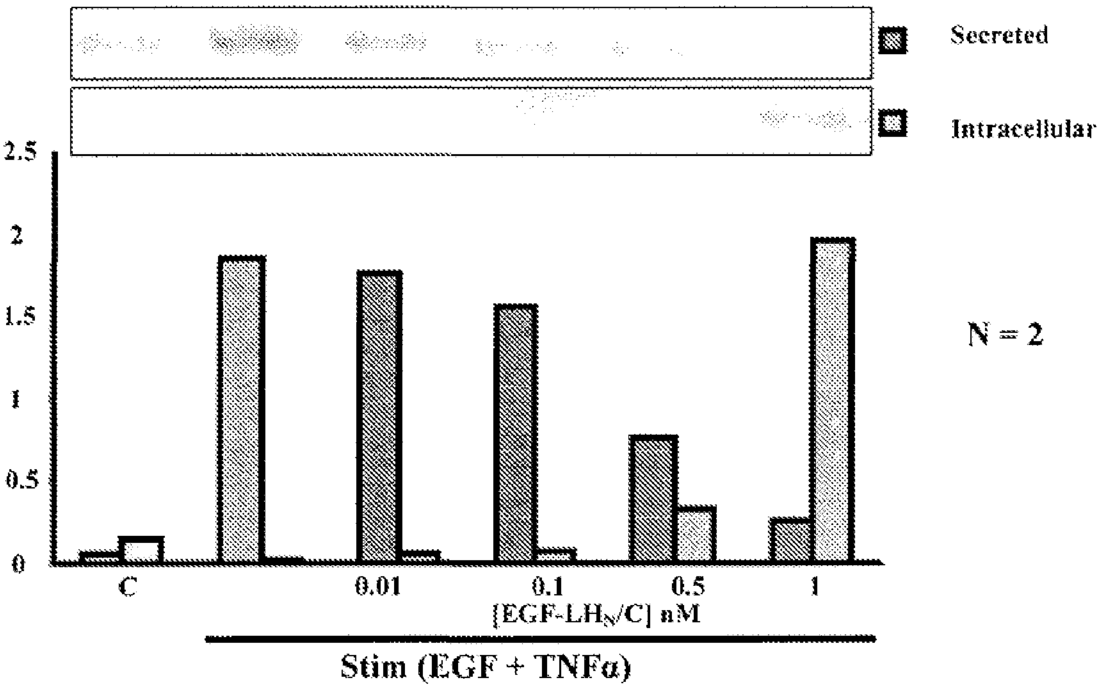
Figure 20:
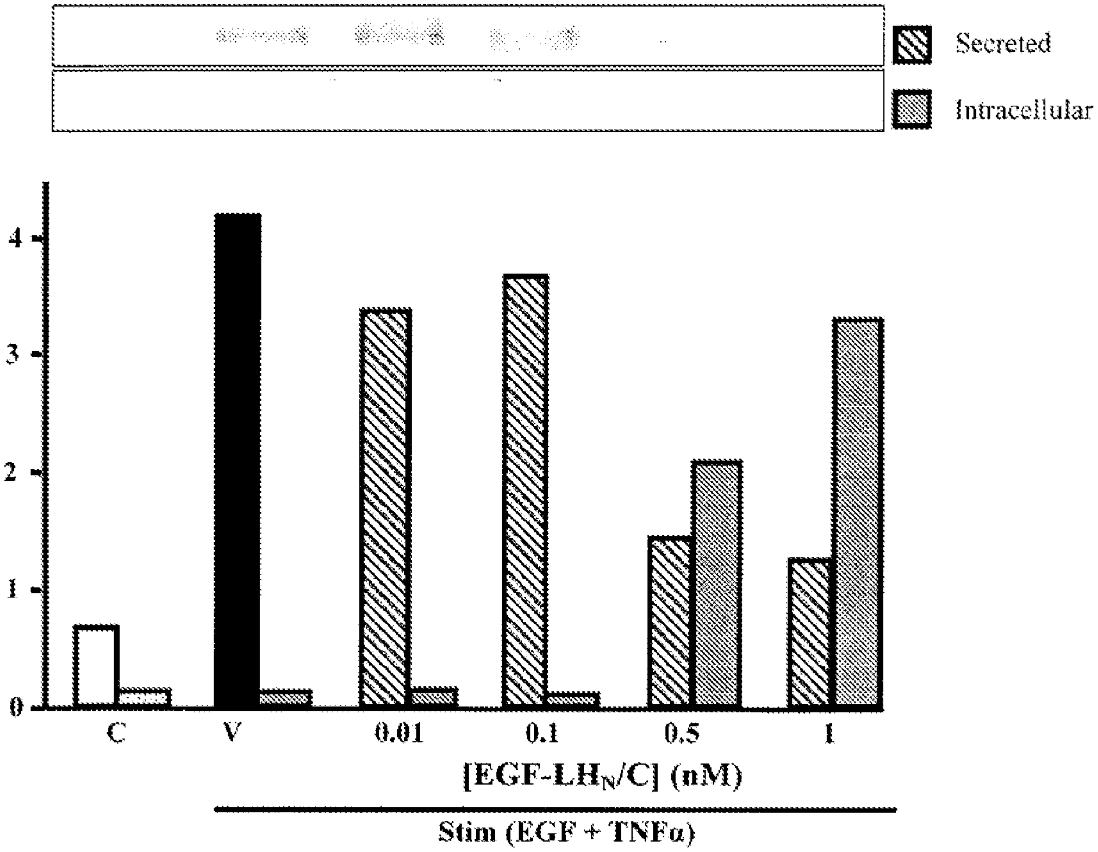

FIG. 19 shows effect of EGF-$LH_N$/C in secreted and intracellular MUC5AC in A549 cells; and FIG. 20 shows effects of EGF-$LH_N$/C on MUC5B content in treated cells. Band density on the nitrocellulose blots was detected using a densitometer and has been plotted in Optical density units×area. As the EGF-$LH_N$/C concentration increases the level of MUC5AC or MUC5B detected in the medium decreases and the intracellular, cell lysate levels increase. Data is representative of two experiments.

C=control (cell culture medium only)

S=EGF & TNF alpha (20 ng/ml & 25 ng/ml respectively)

Stimulation=EGF & TNF alpha (20 ng/ml & 25 ng/ml respectively)

Figure 21:
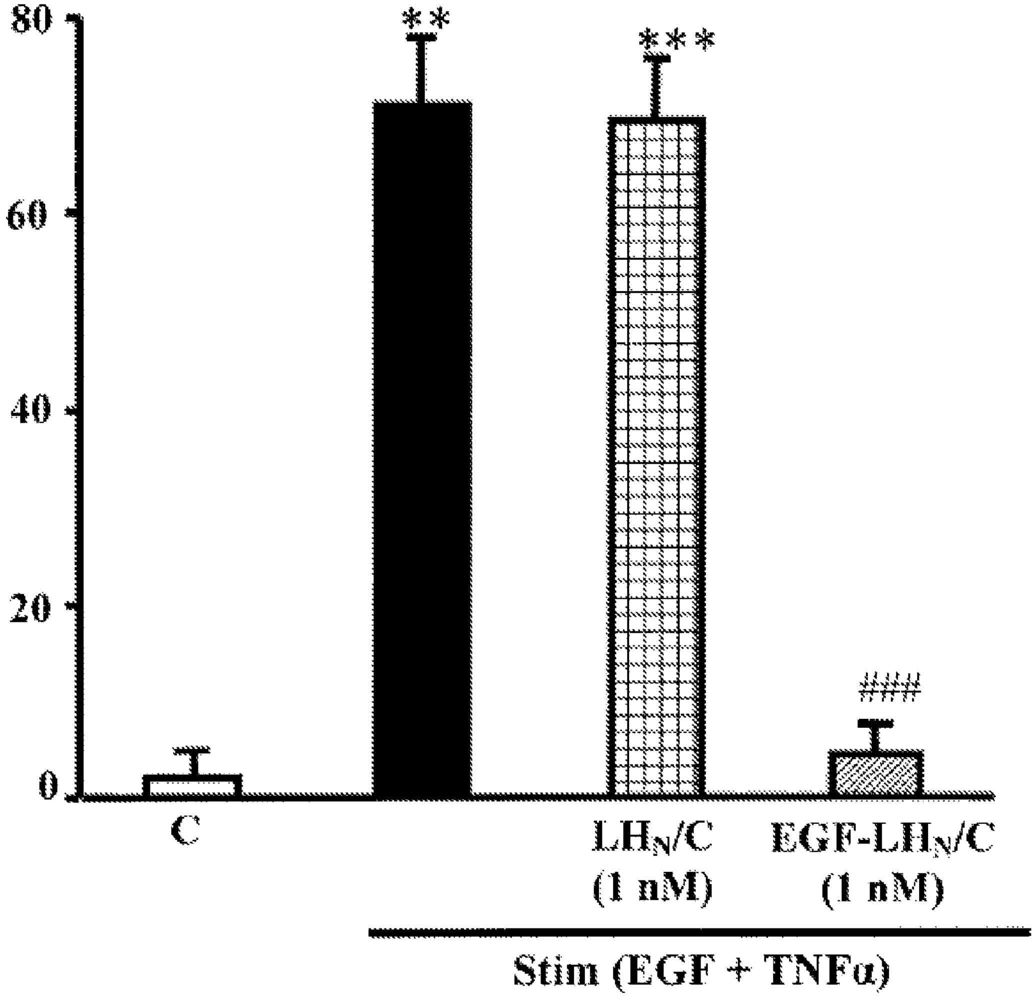

FIG. 21 shows effect of $LH_N$/C on mucin secretion in A549 cells. A549 cells treated for 48 hr with 1 nM $LH_N$/C then stimulated for 24 hr with EGF/TNF alpha in the continued presence of $LH_N$/C showed no inhibition in mucin secretion as measured using the ELLA. Cells treated 24 hr with EGF-$LH_N$/C then stimulated for 48 hr with EGF/TNF alpha in the presence of EGF-$LH_N$/C showed inhibition of mucin secretion in the same experiment.

C=control (cell culture medium only)

VC=vehicle control (50 mM HEPES, 200 mM NaCl—eluant solution for the $LH_N$/C)

Data are Mean and SEM for 2-4 independent experiments.

***$p<0.001$ vs C; ##$p<0.01$ vs Stim.

Figure 22:
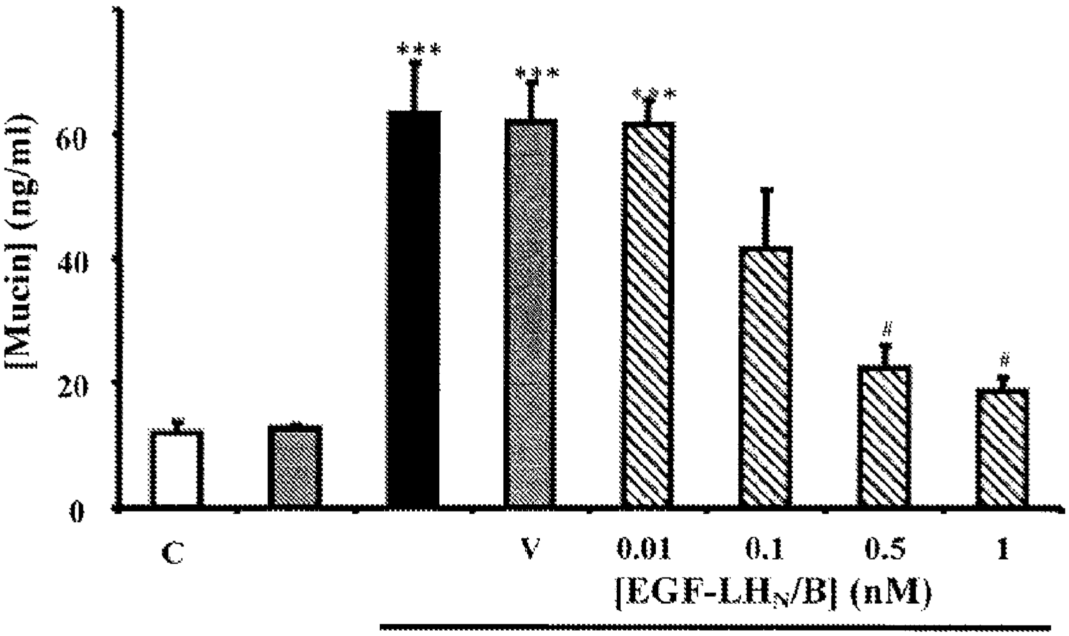

FIG. 22 shows effect of $LH_N$/B-EGF on stimulated mucin secretion in A549 cells. Cells were treated with the fusion or vehicle or medium alone for 48 hour followed by a 24 hour stimulation of the cells with EGF/TNF alpha (Stimulus) in the presence of the construct. Vehicle treated cells received fresh vehicle plus medium only. Medium was collected and assayed for mucin content using the ELLA method with a human mucin standard curve. All mucin levels are shown in ng/ml calculated from the human mucin standard curve within each ELLA plate. Each concentration was assessed in triplicate. EGF-$LH_N$/B concentration in nM.

C=control (cell culture medium only)

Stim=EGF & TNF alpha (20 ng/ml &25 ng/ml respectively)

VC=vehicle control (50 mM Hepes, 200 mM NaCl—eluant solution for the EGF-$LH_N$/B)

Figure 23:
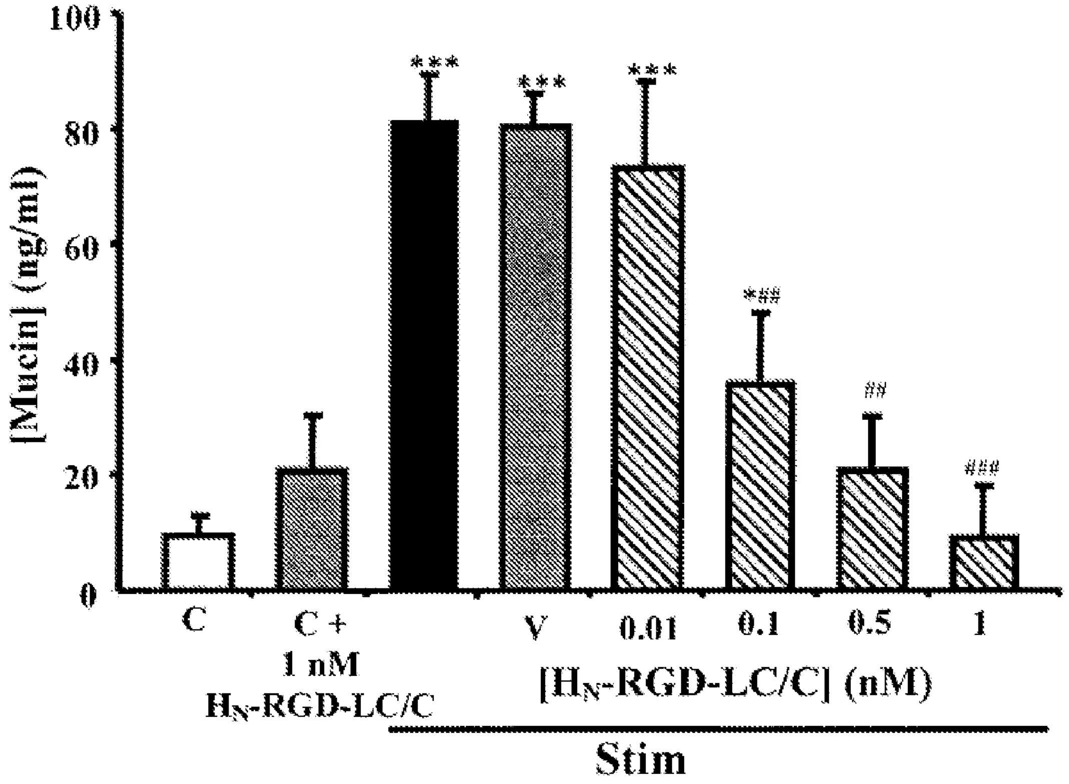

FIG. 23 shows effect of $H_N$-RGD-LC/C on EGF/TNF alpha-induced mucin secretion in A549 cells. A549 Cells treated for 48 hour with varying concentrations of $H_N$-RGD-LC/C then stimulated for 24 hour with EGF/TNF alpha in the continued presence of $H_N$-RGD-LC/C showed a dose-dependent inhibition of mucin release as measured using the ELLA. Each concentration was assessed in triplicate and the figure is representative of two experiments.

C=control (cell culture medium only)

S=EGF & TNF alpha (20 ng/ml &25 ng/ml respectively)

Stimulation=EGF & TNF alpha (20 ng/ml &25 ng/ml respectively)

Figure 24:
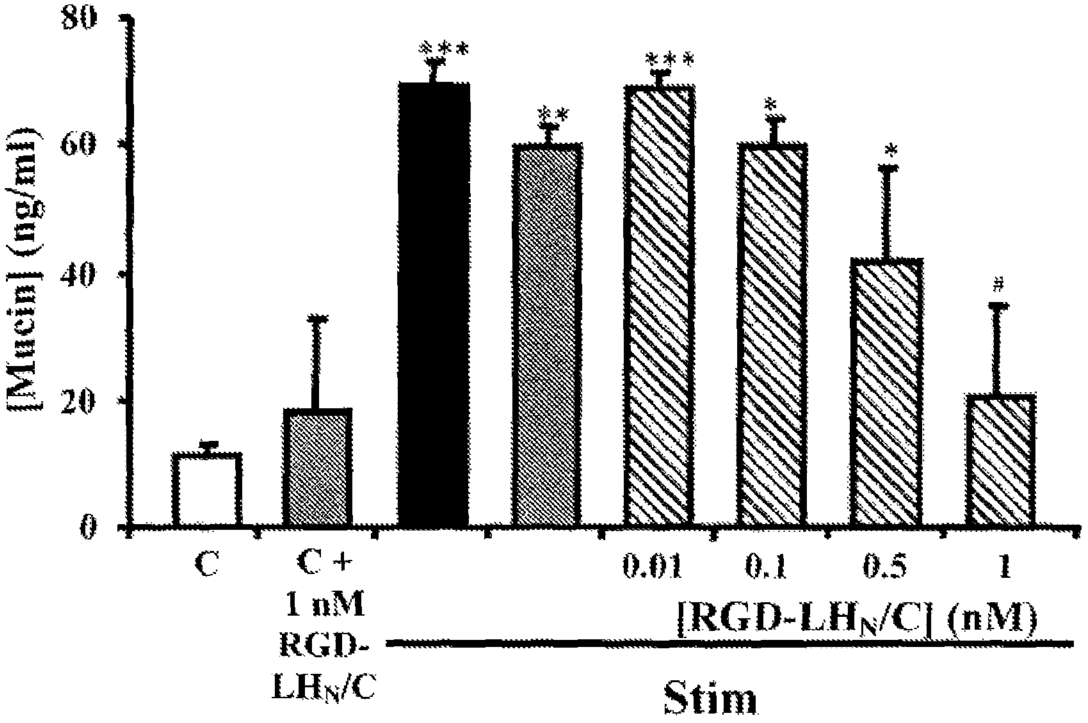

FIG. 24 shows effect of RGD-$LH_N$/C on EGF/TNF alpha-induced mucin secretion in A594 cells. Cells treated for 48 h with RGD-$LH_N$/C then stimulated for 24 h with EGF/TNFα in the continued presence of RGD-$LH_N$/C showed a dose-dependent inhibition of mucin release as measured using the ELLA. Each concentration was assessed in triplicate and the figure is representative of two experiments.

Figure 25:
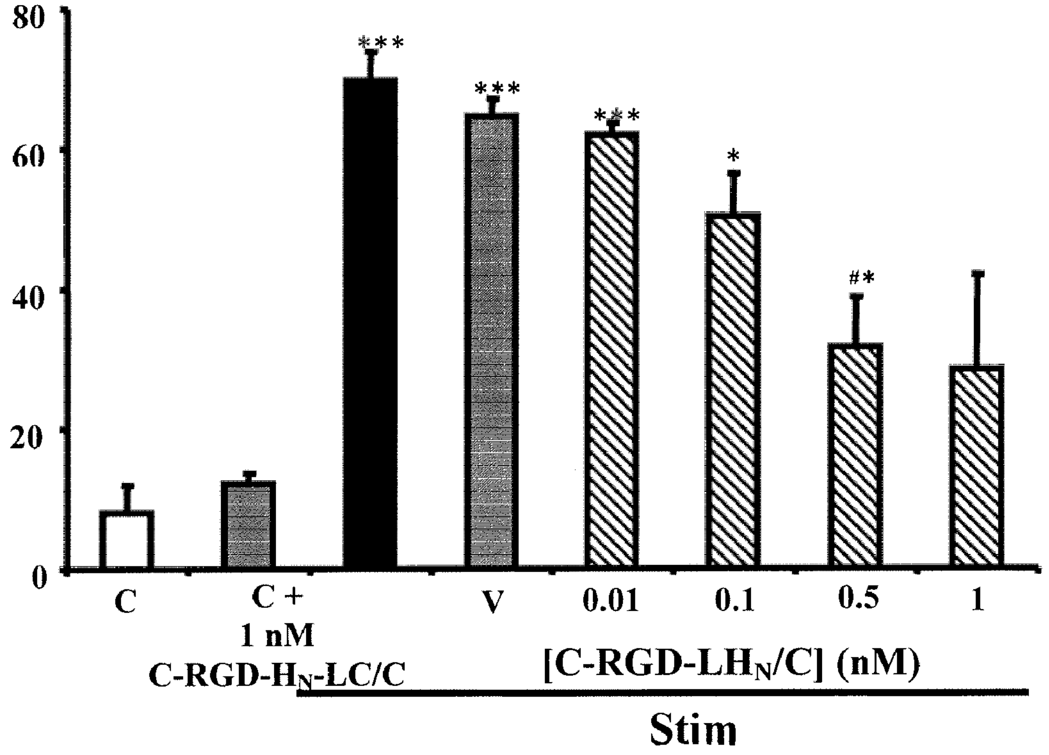

FIG. 25 shows effect of C-RGD-$LH_N$/C on EGF/TNF alpha-induced mucin secretion in A549 cells. Cells treated for 48 h with C-RGD-$H_N$-LC/C then stimulated for 24 h with EGF/TNFα in the continued presence of C-RGD-$H_N$-LC/C showed a dose-dependent inhibition of mucin release as measured using the ELLA. Each concentration was assessed in triplicate and the figure is representative of two experiments.

EXAMPLES

Example 1

Method for the Preparation of Substance P-$LH_N$/A Conjugates

The lyophilised peptide was rehydrated in 0.1% trifluoroacetic acid (TFA) to a final concentration of 10 mM. Aliquots of this solution were stored at −20 degrees C. until use. The $LH_N$/A was desalted into PBSE (PBS containing 1 mM EDTA). The resulting solution (3-5 mg/ml) was reacted with a three- or four-fold molar excess of SPDP by addition of a 10 mM stock solution of SPDP in DMSO. After 3 hours at room temperature the reaction was terminated by desalting over a PD-10 column into PBSE.

A portion of the derivatised $LH_N$/A was removed from the solution and reduced with DTT (5 mM, 30 min). This sample was analysed spectrophotometrically at 280 nm and 343 nm to determine the degree of derivatisation. The degree of derivatisation achieved was typically 2 mol/mol.

The bulk of the derivatised $LH_N$/A and the substance P peptide were mixed in proportions such that the peptide was in four-fold molar excess. The conjugation reaction was allowed to proceed for >16 hours at 4° C.

The product mixture was centrifuged to clear any precipitate that had developed. The supernatant was applied to a PD-10 column equilibrated in PBS and protein fractions were eluted by addition of PBS. Peptide and reaction by-products eluted after the main peak of protein and were discarded.

The conjugate mixture was concentrated to >1 mg/ml by centrifugation through concentrators (with 10000 molecular weight exclusion limit). The concentrated conjugate mixture was analysed by SDS-PAGE and Western blotting (probed with anti-substance P antibody) to confirm linkage of substance P peptide to $LH_N$/A.

The method described is for linkage of substance P peptide covalently to $LH_N$/A via a SPDP linker. A sulphydryl residue is incorporated into the C-terminus of the substance P residue, in this case by the addition of a Cys residue. Alternative linkers are available, including linkers utilising similar chemistry of derivatisation but generating non-reducible covalent bonds between the linked species.

The Substance P peptide sequence used in this particular example is RPKPQQFFGLMC (SEQ ID NO:22), though alternative sequences are also suitable, e.g. CRPKPQQFF-GLM (SEQ ID NO:23), i.e. substance P with an N-terminal Cys.

The method described does not make use of any tagging system (e.g. poly His) to purify the conjugate from free $LH_N$/A. This has been demonstrated to be a successful method for the preparation of opioid peptide $LH_N$/A such the receptor binding function of the peptide was not compromised. A similar approach can be applied to the synthesis of subP-$LH_N$/A.

Figure 1:
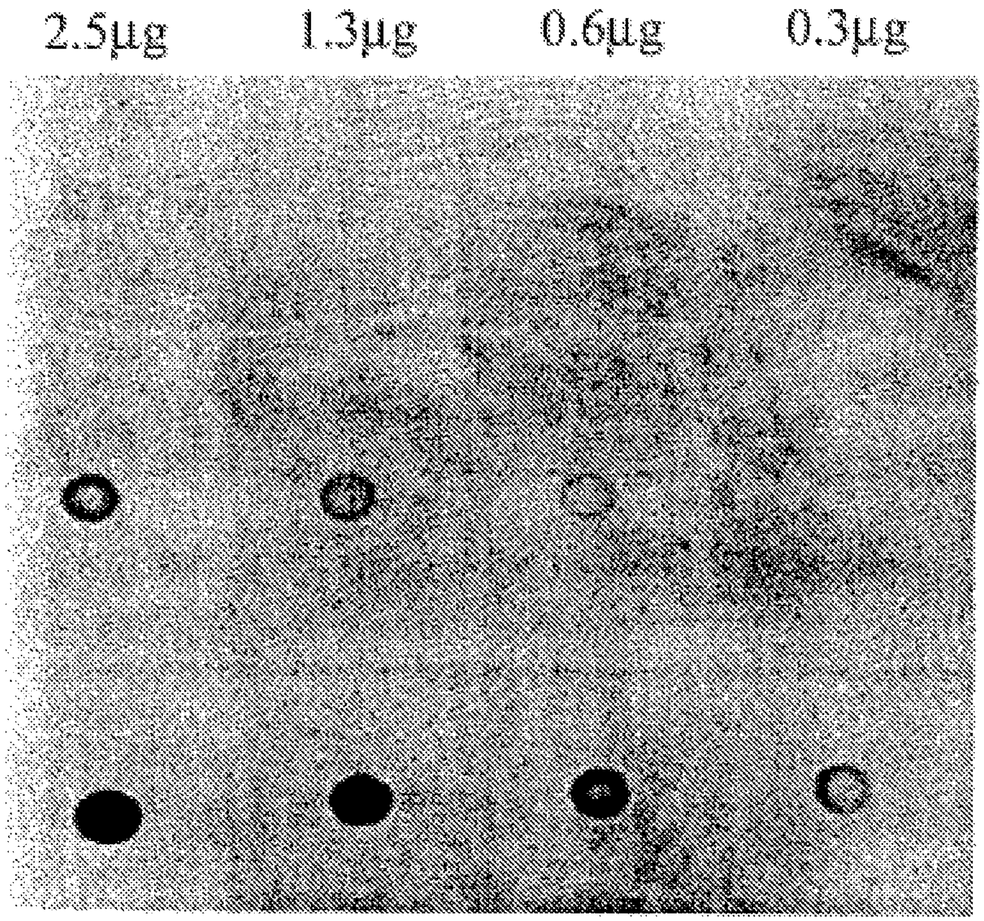
FIG. 1 illustrates the preparation of the substance P-$LH_N$/A conjugate of Example 1

FIG. 1 illustrates the preparation of the substance P-$LH_N$/A conjugate of Example 1. In the results shown in FIG. 1, $LH_N$/A and substance P-$LH_N$/A samples at the concentrations indicated were applied to nitrocellulose and probed with rabbit anti-substance P antibody (upper two rows). The emergence of cross-reaction with the conjugate (second row), rather than the $LH_N$/A (first row), is indicative of substance P conjugated to $LH_N$/A. The lower control row illustrates the presence of $LH_N$/A.

Figure 2:
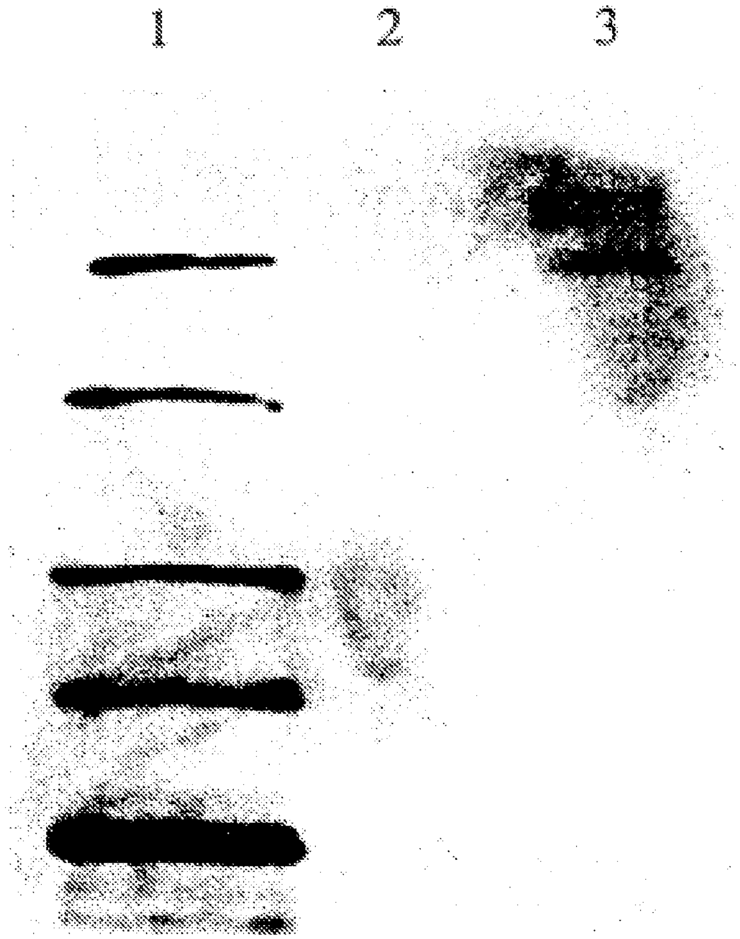
FIG. 2 shows Western blot detection of conjugated substance P-$LH_N$/A

FIG. 2 shows Western blot detection of conjugated substance P-$LH_N$/A. Samples of substance P-$LH_N$/A (lane 3) and $LH_N$/A (lane 2) were electrophoresed alongside molecular weight markers (lane 1). Detection of substance P by rat anti-substance P antisera indicated protein of approx. 100 kDa molecular weight in the conjugate lane, but no such band in the $LH_N$/A only lane. Thus the conjugated $LH_N$/A does contain substance P.

Example 2

Method for the Preparation of a Broad Specificity Agent

Conjugation and purification of WGA-$LH_N$/A. WGA (10 mg/ml in phosphate-buffered saline (PBS)) was reacted with an equal concentration of SPDP (10 mM in dimethyl sulphoxide (DMSO)) for one hour at ambient temperature. Reaction by-products were removed by desalting into PBS prior to reduction of the cross-linker with dithiothreitol. The thiopyridone and DTT were then removed by desalting into PBS to result in derivatised WGA (dWGA) with 1 mole —SH incorporated per mole of WGA.

$LH_N$/A at a concentration of 3-5 mg/ml in PBSE (PBS containing 1 mM EDTA) was reacted with a three or four-fold molar excess of SPDP (10 mM in DMSO). After 3 h at ambient temperature the reaction was terminated by desalting over a PD-10 column into PBSE.

The derivatised WGA (dWGA) and the derivatised $LH_N$/A (d$LH_N$/A) were mixed in a 3:1 molar ratio. After 16 h at 4° C. The mixture was centrifuged to clear any precipitate that had developed. The supernatant was concentrated by ultrafiltration before application to a Superose™ 12 column on an FPLC® chromatography system (Phamacia). The column was eluted with PBS and the fractions containing high molecular weight conjugate material (separated from free dWGA) were pooled and applied to PBS-washed N-acetylglucosamine-agarose (GlcNAc-agarose). WGA-$LH_N$/A conjugate bound to the GlcNAc-agarose and was eluted from the column by the addition of 0.3 M N-acetylglucosamine in PBS. The elution profile was followed at 280 nm and fractions containing conjugate were pooled, dialysed against PBS, and stored at 4° C. until use.

Figure 3:
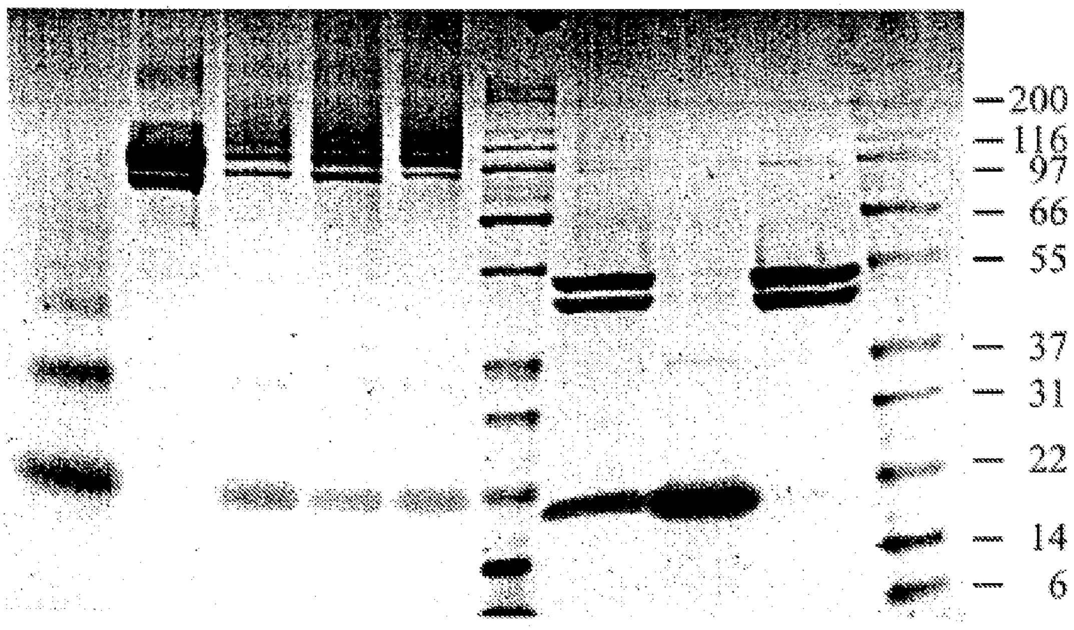
FIG. 3 shows SDS-PAGE analysis of a WGA-$LH_N$/A purification scheme

FIG. 3 shows SDS-PAGE analysis of WGA-$LH_N$/A purification scheme. Protein fractions were subjected to 4-20% polyacrylamide SDS-PAGE prior to staining with Coomassie blue. Lanes 6-8 were run in the presence of 0.1 M DTT. Lanes 1 (&7) and 2 (& 8) represent derivatised WGA and derivatised $LH_N$/A respectively. Lanes 3-5 represent conjugation mixture, post-Superose-12 chromatography and post GlcNAc-affinity chromatography respectively. Lanes 6 represents a sample of reduced final material. Approximate molecular masses (kDa) are indicated on the Figure.

Example 3

Preparation and Maintenance of Neuronal Cultures and Inhibition of Neurotransmitter Release PC 2 cells were seeded at a density of $4\times10^5$ cells/well onto 24 well (matrigel coated) plates (NUNC™) from stocks grown in suspension. The cells were cultured for 1 week prior to use in RPMI, 10% horse serum, 5% foetal bovine serum, 1% L-glutamine. SH-SY5Y cells were seeded at a density of 5.times.10.sup.5 cells/well onto 24 well plates (FALCON™). The cells were cultured in HAM-F12:MEM (1:1 v/v), 15% foetal bovine serum, 1% MEM non-essential amino acids, 2 mM L-glutamine for 1 week prior to use. Embryonic spinal cord (eSC) neurons were prepared from spinal cords dissected from 14-15 day old foetal Sprague Dawley rats and were used after 21 days in culture using a modification of previously described method.

Inhibition of transmitter release. PC12 cells or SH-SY5Y cells were washed with a balanced salt solution (BSS:137 mM NaCl, 5 mM KCl, 2 mM CaCl2, 4.2 mM NaHCO3, 1.2 mM MgCl2, 0.44 mM KH2PO4, 5 mM glucose, 20 mM HEPES, pH7.4) and loaded for 1 hour with $[^3H]$-noradrenaline (2 μCi/ml, 0.5 ml/well) in BSS containing 0.2 mM ascorbic acid and 0.2 mM pargyline. Cells were washed 4 times (at 15 minutes intervals for 1 hour) then basal release determined by a 5 minute incubation with BSS (5 mM $K^+$). Cells were then depolarised with 100 mM $K^+$ (BSS with $Na^+$ reduced accordingly) for 5 minutes to determine stimulated release. Superfusate (0.5 ml) was removed to tubes on ice and briefly centrifuged to pellet any detached cells. Adherent cells were solubilised in 2 M acetic acid/0.1% trifluoroacetic acid (250 μl/well). The quantity of released and non-released radio label was determined by liquid scintillation counting of cleared superfusates and cell lysates respectively. Total uptake was calculated by addition of released and retained radioactivity and the percentage release calculated ((released counts/total uptake counts)×100).

eSC neurons were loaded with $[^3H]$-glycine for 30 minutes prior to determination of basal and potassium-stimulated release of transmitter. A sample of 0.2 M NaOH-lysed cells was used to determine total counts, from which % release could be calculated.

Figure 4:
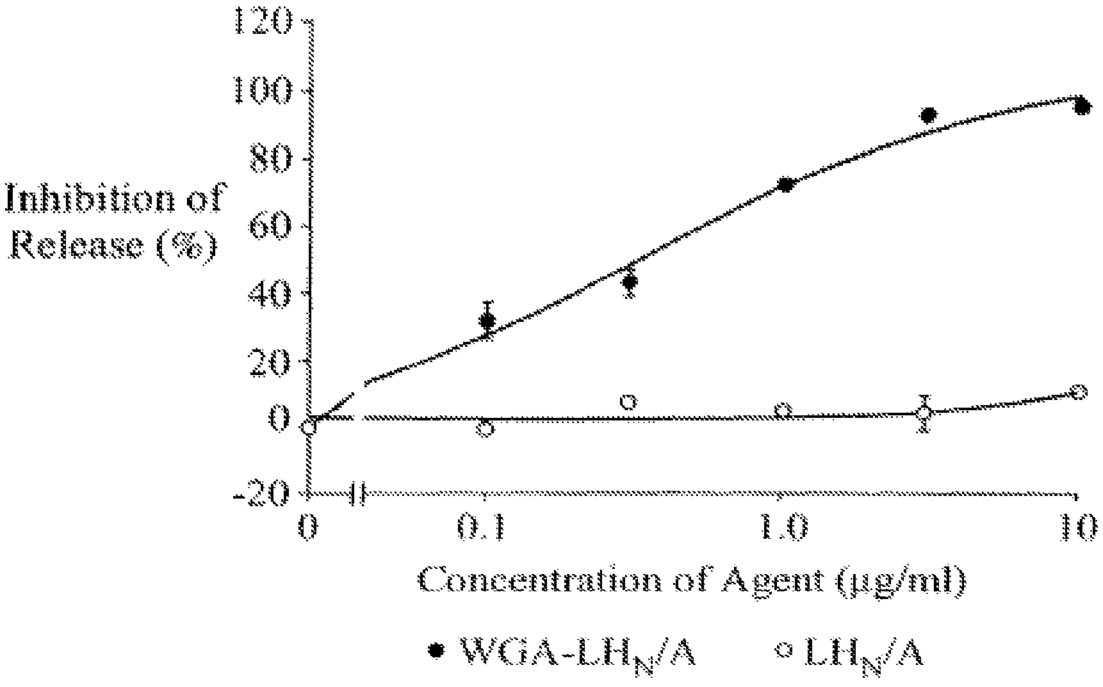
FIGS. 4-6 show inhibition of neurotransmitter release from cultured neuronal cells.
Figure 5:
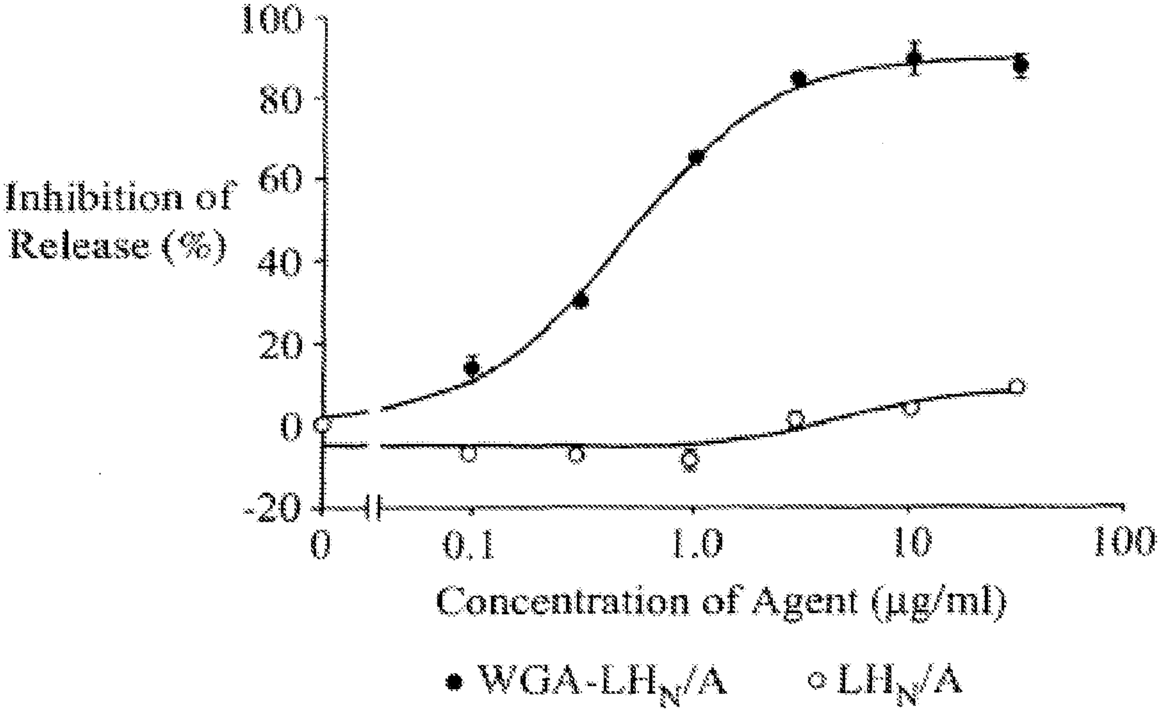
Figure 6:
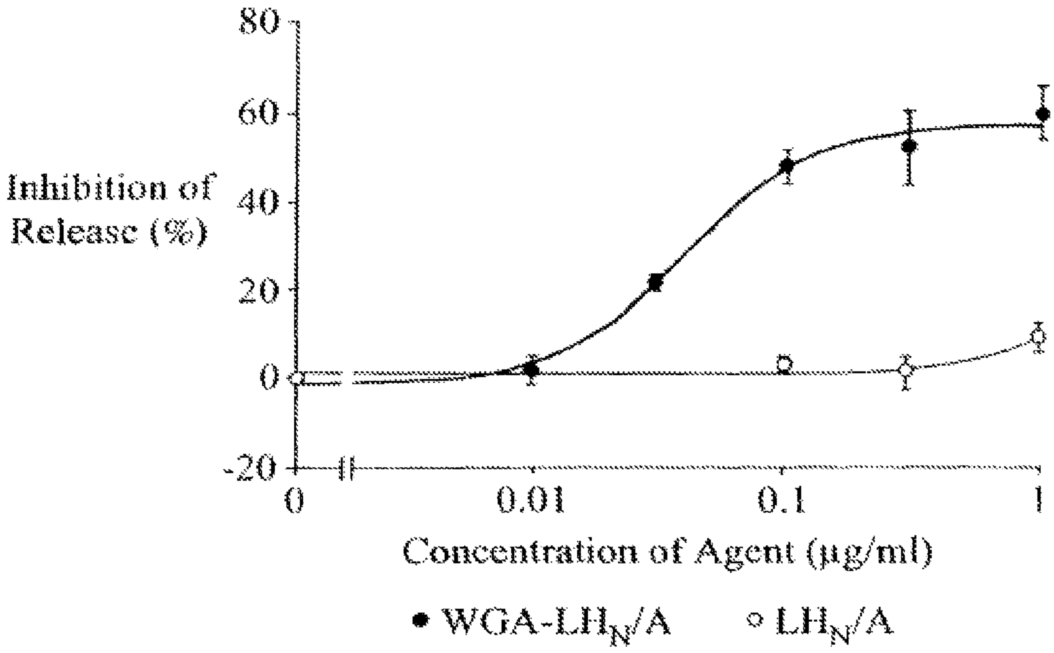

FIGS. 4-6 show inhibition of neurotransmitter release from cultured neuronal cells. PC12 (FIG. 4), SH-SY5Y cells (FIG. 5) and eSC neurons (FIG. 6) exposed for three days to a range of concentrations of WGA-$LH_N$/A (filled symbols) and $LH_N$/A (open symbols) were assessed for stimulated $[^3H]$-noradrenaline release (SH-SY5Y and PC12 cells) or $[^3H]$-glycine release (eSC) capability. Results are expressed as percentage inhibition compared to untreated controls. Each concentration was assessed in triplicate. For each cell type the dose response curve is representative of at least three experiments. Each point shown is the mean of at least three determinations+/−SE of the mean.

Figure 7:
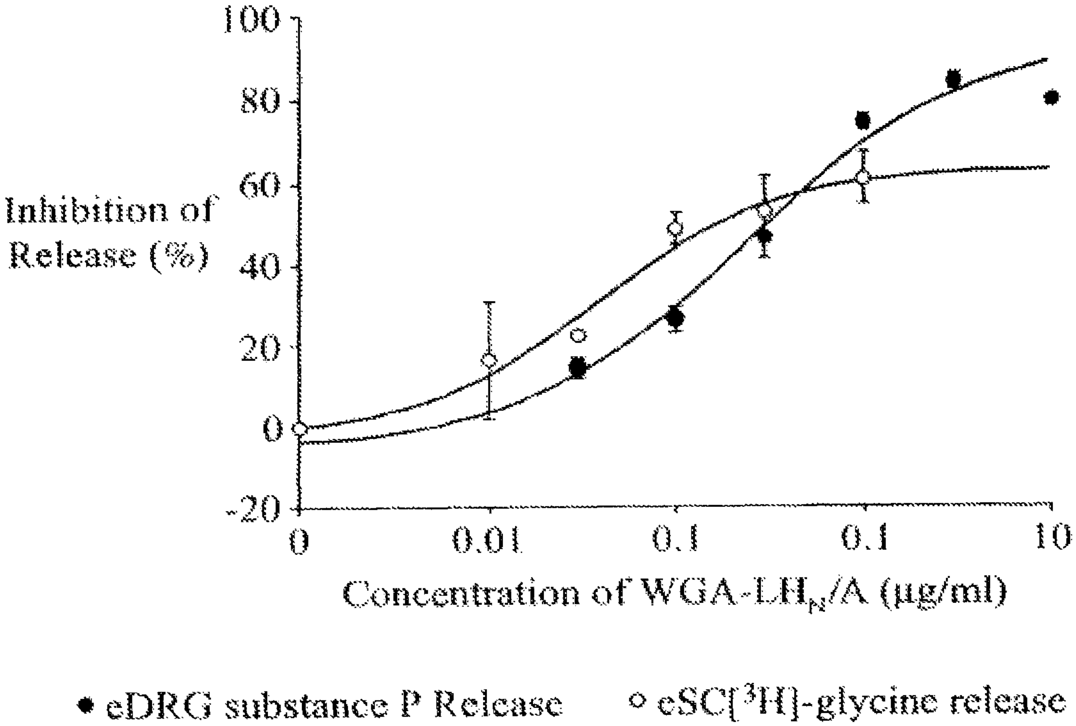
FIG. 7 shows WGA-$LH_N$/A inhibits release from, but does not have specificity for, eDRG neurons.

FIG. 7 shows dose-response curves of WGA-$LH_N$/A inhibition of eDRG substance P and eSC $[^3H]$-glycine release. Cells were exposed to conjugate for three days. Representative curves are shown. Mean $IC_{50}$eDRG:0.32+/−0.05 μg/ml (n=4), eSC: 0.06+/−0.01 μg/ml (n=3).

Example 4

Method for the Preparation of LC/B-Epidermal Growth Factor with a Translocation Domain from Diphtheria Toxin by Recombinant Expression Using standard DNA manipulation procedures, the DNA encoding LC/B, diphtheria toxin amino acids 194-380, and epidermal growth factor are assembled in frame and inserted into an appropriate expression vector. Inserted between the LC/B DNA and the diphtheria toxin translocation domain is DNA encoding a short spacer sequence with a specific cleavable peptide bond (↓), bounded by a pair of cysteine amino acids. Examples of specific enzymes that may be used to activate the fusion protein include factor Xa (IEGR↓) (SEQ ID NO:24), enterokinase (DDDDK↓) (SEQ ID NO:25), TEV protease (EXXYXQS↓G) (SEQ ID NO:26), precission (LEVLFQ↓GP) (SEQ ID NO:27), Thrombin (LVPR↓GS) (SEQ ID NO:28) and genenase (HY or YH). Expression of a single polypeptide of the form LC/B-$DT_{194-380}$-EGF is achieved in *E. coli* using standard techniques. The expressed fusion protein is isolated from *E. coli* by standard purification techniques and cleaved by the specific activation enzyme prior to assessment in an in vitro cell model.

Example 5

Method for the Preparation of LC/C-Epidermal Growth Factor with a Translocation Domain from *Pseudomonas* Exotoxin by Recombinant Expression Using standard DNA manipulation procedures, the DNA encoding LC/C, *pseudomonas* exotoxin amino acids 405-613, and epidermal growth factor are assembled in frame and inserted into an appropriate expression vector. Inserted between the LC/C DNA and the *pseudomonas* exotoxin translocation domain is DNA encoding a short spacer sequence with a specific cleavable peptide bond, bounded by a pair of cysteine amino acids. Examples of specific enzymes that may be used to activate the fusion protein include factor Xa (IEGR↓), (SEQ ID NO:24), enterokinase (DDDDK↓) (SEQ ID NO:25), TEV protease (EXXYXQS↓G) (SEQ ID NO:26), precission (LEVLFQ↓GP) (SEQ ID NO:27), Thrombin (LVPR↓GS) (SEQ ID NO:28) and genenase (HY or YH). Expression of a single polypeptide of the form LC/C-$PE_{405-613}$-EGF is achieved in *E. coli* using standard techniques. The expressed fusion protein is isolated from *E. coli* by standard purification techniques and cleaved by the specific activation enzyme prior to assessment in an in vitro cell model.

Example 6

Method for the Preparation of LC/A-Epidermal Growth Factor with a Translocation Domain from Influenza Virus Haemagglutinin by Recombinant Expression Using standard DNA manipulation procedures, the DNA encoding LC/A, GLFGAIAGFIENGWEGMIDGWYG (SEQ ID NO:21) from influenza virus haemagglutinin (HA), and epidermal growth factor are assembled in frame and inserted into an appropriate expression vector. Inserted between the LC/A DNA and the haemagglutinin sequence is DNA encoding a short spacer sequence with a specific cleavable peptide bond, bounded by a pair of cysteine amino acids. Examples of specific enzymes that may be used to activate the fusion protein include factor Xa (IEGR↓) (SEQ ID NO:24), enterokinase (DDDDK↓) (SEQ ID NO:25), TEV protease (EXXYXQS↓G) (SEQ ID NO:26), precission (LEVLFQ↓GP) (SEQ ID NO:27), Thrombin (LVPR↓GS) (SEQ ID NO:28) and genenase (HY or YH). Expression of a single polypeptide of the form LC/A-HA-EGF is achieved in *E. coli* using standard techniques. The expressed fusion protein is isolated from *E. coli* by standard purification techniques and cleaved by the specific activation enzyme prior to assessment in an in vitro cell model.

The agent described in this invention can be used in vivo, either directly or as a pharmaceutically acceptable salt, for the treatment of conditions involving mucus hypersecretion, including COPD and asthma.

Example 7

Preparation of a $LH_N$/B Backbone Construct

The following procedure creates a clone for use as an expression backbone for multidomain fusion expression. This example is based on preparation of a serotype B based clone (SEQ ID NO:1).

Preparation of Cloning and Expression Vectors pCR 4 (Invitrogen) is the chosen standard cloning vector chosen due to the lack of restriction sequences within the vector and adjacent sequencing primer sites for easy construct confirmation. The expression vector is based on the PMAL (NEB) expression vector which has the desired restriction sequences within the multiple cloning site in the correct orientation for construct insertion (BamHI-SalI-PstI-HindIII). A fragment of the expression vector has been removed to create a non-mobilisable plasmid and a variety of different fusion tags have been inserted to increase purification options.

Preparation of LC/B

The LC/B is created by one of two ways:

The DNA sequence is designed by back translation of the LC/B amino acid sequence (obtained from freely available database sources such as GenBank (accession number P10844) or Swissprot (accession locus BXB_CLOBO) using one of a variety of reverse translation software tools (for example EditSeq best *E. coli* reverse translation (DNASTAR Inc.), or Backtranslation tool v2.0 (Entelechon)). BamHI/SalI recognition sequences are incorporated at the 5' and 3' ends respectively of the sequence maintaining the correct reading frame. The DNA sequence is screened (using software such as MapDraw, DNASTAR Inc.) for restriction enzyme cleavage sequences incorporated during the back translation. Any cleavage sequences that are found to be common to those required by the cloning system are removed manually from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004). This optimised DNA sequence containing the LC/B open reading frame (ORF) is then commercially synthesized (for example by Entelechon, Geneart or Sigma-Genosys) and is provided in the pCR 4 vector.

The alternative method is to use PCR amplification from an existing DNA sequence with BamHI and SalI restriction enzyme sequences incorporated into the 5' and 3' PCR primers respectively. Complementary oligonucleotide primers are chemically synthesised by a Supplier (for example MWG or Sigma-Genosys) so that each pair has the ability to hybridize to the opposite strands (3' ends pointing "towards" each other) flanking the stretch of *Clostridium* target DNA, one oligonucleotide for each of the two DNA strands. To generate a PCR product the pair of short oligonucleotide primers specific for the *Clostridium* DNA sequence are mixed with the *Clostridium* DNA template and other reaction components and placed in a machine (the 'PCR machine') that can change the incubation temperature of the reaction tube automatically, cycling between approximately 94° C. (for denaturation), 55° C. (for oligonucleotide annealing), and 72° C. (for synthesis). Other reagents required for amplification of a PCR product include a DNA polymerase (such as Taq or Pfu polymerase), each of the four nucleotide dNTP building blocks of DNA in equimolar amounts (50-200 μM) and a buffer appropriate for the enzyme optimised for Mg2+ concentration (0.5-5 mM).

The amplification product is cloned into pCR 4 using either, TOPO TA cloning for Taq PCR products or Zero Blunt TOPO cloning for Pfu PCR products (both kits commercially available from Invitrogen). The resultant clone is checked by sequencing. Any additional restriction sequences which are not compatible with the cloning system are then removed using site directed mutagenesis (for example using Quickchange (Stratagene Inc.)).

Preparation of $H_N$/B Insert

The $H_N$ is created by one of two ways:

The DNA sequence is designed by back translation of the $H_N$/B amino acid sequence (obtained from freely available database sources such as GenBank (accession number P10844) or Swissprot (accession locus BXB_CLOBO)) using one of a variety of reverse translation software tools (for example EditSeq best *E. coli* reverse translation (DNASTAR Inc.), or Back translation tool v2.0 (Entelechon)). A PstI restriction sequence added to the N-terminus and XbaI-stop codon-HindIII to the C-terminus ensuring the correct reading frame in maintained. The DNA sequence is screened (using software such as MapDraw, DNASTAR Inc.) for restriction enzyme cleavage sequences incorporated during the back translation. Any sequences that are found to be common to those required by the cloning system are removed manually from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004). This optimised DNA sequence is then commercially synthesized (for example by Entelechon, Geneart or Sigma-Genosys) and is provided in the pCR 4 vector.

The alternative method is to use PCR amplification from an existing DNA sequence with PstI and XbaI-stop codon-HindIII restriction enzyme sequences incorporated into the 5' and 3' PCR primers respectively. The PCR amplification is performed as described above. The PCR product is inserted into pCR 4 vector and checked by sequencing. Any additional restriction sequences which are not compatible with the cloning system are then removed using site directed mutagenesis (for example using Quickchange (Stratagene Inc.)).

Preparation of the Spacer (LC-$H_N$ Linker)

The LC-$H_N$ linker can be designed from first principle, using the existing sequence information for the linker as the template. For example, the serotype B linker (in this case defined as the inter-domain polypeptide region that exists between the cysteines of the disulphide bridge between LC and $H_N$) has the sequence KSVKAPG (SEQ ID NO: 40). This sequence information is freely available from available database sources such as GenBank (accession number P10844) or Swissprot (accession locus BXB_CLOBO). For generation of a specific protease cleavage site, the recognition sequence for enterokinase is inserted into the activation loop to generate the sequence VDEEKLYDDDDKDRWGSSLQ (SEQ ID NO: 41). Using one of a variety of reverse translation software tools (for example EditSeq best *E. coli* reverse translation (DNASTAR Inc.), or Backtranslation tool v2.0 (Entelechon)), the DNA sequence encoding the linker region is determined. BamHI/SalI and PstI/XbaI/stop codon/HindIII restriction enzyme sequences are incorporated at either end, in the correct reading frames. The DNA sequence is screened (using software such as MapDraw, DNASTAR Inc.) for restriction enzyme cleavage sequences incorporated during the back translation. Any sequences that are found to be common to those required by the cloning system are removed manually from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004). This optimised DNA sequence is then commercially synthesized (for example by Entelechon, Geneart or Sigma-Genosys) and is provided in the pCR 4 vector. If it is desired to clone the linker out of pCR 4 vector, the vector (encoding the linker) is cleaved with either BamHI+SalI or PstI+XbaI combination restriction enzymes. This cleaved vector then serves as the recipient vector for insertion and ligation of either the LC DNA (cleaved with BamHI/SalI) or $H_N$ DNA (cleaved with PstI/XbaI). Once the LC or the $H_N$ encoding DNA is inserted upstream or downstream of the linker DNA, the entire LC-linker or linker-$H_N$ DNA fragment can the be isolated and transferred to the backbone clone.

As an alternative to independent gene synthesis of the linker, the linker-encoding DNA can be included during the synthesis or PCR amplification of either the LC or $H_N$.

Assembly and Confirmation of the Backbone Clone

The LC or the LC-linker is cut out from the pCR 4 cloning vector using BamHI/SalI or BamHI/PstI restriction enzymes digests. The PMAL expression vector is digested with the same enzymes but is also treated with calf intestinal protease (CIP) as an extra precaution to prevent re-circularisation. Both the LC or LC-linker region and the PMAL vector backbone are gel purified. The purified insert and vector backbone are ligated together using T4 DNA ligase and the product is transformed with TOP10 cells which are then screened for LC insertion using BamHI/SalI or BamHI/PstI restriction digestion. The process is then repeated for the $H_N$ or linker-$H_N$ insertion into the PstI/HindIII or SalI/HindIII sequences of the PMAL-LC construct.

Screening with restriction enzymes is sufficient to ensure the final backbone is correct as all components are already sequenced confirmed, either during synthesis or following PCR amplification. However, during the sub-cloning of some components into the backbone, where similar size fragments are being removed and inserted, sequencing of a small region to confirm correct insertion is required.

Example 8

Preparation of a $LH_N$/C Backbone Construct

The following procedure creates a clone for use as an expression backbone for multidomain fusion expression. This example is based on preparation of a serotype C based clone (SEQ ID NO:2).

Preparation of Cloning and Expression Vectors pCR 4 (Invitrogen) is the chosen standard cloning vector chosen due to the lack of restriction sequences within the vector and adjacent sequencing primer sites for easy construct confirmation. The expression vector is based on the PMAL (NEB) expression vector which has the desired restriction sequences within the multiple cloning site in the correct orientation for construct insertion (BamHI-SalI-PstI-HindIII). A fragment of the expression vector has been removed to create a non-mobilisable plasmid and a variety of different fusion tags have been inserted to increase purification options.

Preparation of LC/C

The LC/C is created by one of two ways:

The DNA sequence is designed by back translation of the LC/C amino acid sequence (obtained from freely available database sources such as GenBank (accession number P18640) or Swissprot (accession locus BXC1_CLOBO) using one of a variety of reverse translation software tools (for example EditSeq best *E. coli* reverse translation (DNASTAR Inc.), or Backtranslation tool v2.0 (Entelechon)). BamHI/SalI recognition sequences are incorporated at the 5' and 3' ends respectively of the sequence maintaining the correct reading frame. The DNA sequence is screened (using software such as MapDraw, DNASTAR Inc.) for restriction enzyme cleavage sequences incorporated during the back translation. Any cleavage sequences that are found to be common to those required by the cloning system are removed manually from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004). This optimised DNA sequence containing the LC/C open reading frame (ORF) is then commercially synthesized (for example by Entelechon, Geneart or Sigma-Genosys) and is provided in the pCR 4 vector.

The alternative method is to use PCR amplification from an existing DNA sequence with BamHI and SalI restriction enzyme sequences incorporated into the 5' and 3' PCR primers respectively. Complementary oligonucleotide primers are chemically synthesised by a Supplier (for example MWG or Sigma-Genosys) so that each pair has the ability to hybridize to the opposite strands (3' ends pointing “towards” each other) flanking the stretch of *Clostridium* target DNA, one oligonucleotide for each of the two DNA strands. To generate a PCR product the pair of short oligonucleotide primers specific for the *Clostridium* DNA sequence are mixed with the *Clostridium* DNA template and other reaction components and placed in a machine (the ‘PCR machine’) that can change the incubation temperature of the reaction tube automatically, cycling between approximately 94° C. (for denaturation), 55° C. (for oligonucleotide annealing), and 72° C. (for synthesis). Other reagents required for amplification of a PCR product include a DNA polymerase (such as Taq or Pfu polymerase), each of the four nucleotide dNTP building blocks of DNA in equimolar amounts (50-200 μM) and a buffer appropriate for the enzyme optimised for Mg2+ concentration (0.5-5 mM).

The amplification product is cloned into pCR 4 using either, TOPO TA cloning for Taq PCR products or Zero Blunt TOPO cloning for Pfu PCR products (both kits commercially available from Invitrogen). The resultant clone is checked by sequencing. Any additional restriction sequences which are not compatible with the cloning system are then removed using site directed mutagenesis (for example using Quickchange (Stratagene Inc.)).

Preparation of $H_N$/C Insert

The $H_N$ is created by one of two ways:

The DNA sequence is designed by back translation of the $H_N$/C amino acid sequence (obtained from freely available database sources such as GenBank (accession number P18640) or Swissprot (accession locus BXC1_CLOBO)) using one of a variety of reverse translation software tools (for example EditSeq best *E. coli* reverse translation (DNASTAR Inc.), or Back translation tool v2.0 (Entelechon)). A PstI restriction sequence added to the N-terminus and XbaI-stop codon-HindIII to the C-terminus ensuring the correct reading frame in maintained. The DNA sequence is screened (using software such as MapDraw, DNASTAR Inc.) for restriction enzyme cleavage sequences incorporated during the back translation. Any sequences that are found to be common to those required by the cloning system are removed manually from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004). This optimised DNA sequence is then commercially synthesized (for example by Entelechon, Geneart or Sigma-Genosys) and is provided in the pCR 4 vector.

The alternative method is to use PCR amplification from an existing DNA sequence with PstI and XbaI-stop codon-HindIII restriction enzyme sequences incorporated into the 5' and 3' PCR primers respectively. The PCR amplification is performed as described above. The PCR product is inserted into pCR 4 vector and checked by sequencing. Any additional restriction sequences which are not compatible with the cloning system are then removed using site directed mutagenesis (for example using Quickchange (Stratagene Inc.)).

Preparation of the Spacer (LC-$H_N$ Linker)

The LC-$H_N$ linker can be designed from first principle, using the existing sequence information for the linker as the template. For example, the serotype C linker (in this case defined as the inter-domain polypeptide region that exists between the cysteines of the disulphide bridge between LC and $H_N$) has the sequence HKAIDGRSLYNKTLD (SEQ ID NO: 42). This sequence information is freely available from available database sources such as GenBank (accession number P18640) or Swissprot (accession locus BXC1_CLOBO). For generation of a specific protease cleavage site, the recognition sequence for enterokinase is inserted into the activation loop to generate the sequence VDGIITSKTKSD-DDDKNKALNLQ (SEQ ID NO: 43). Using one of a variety of reverse translation software tools (for example EditSeq best *E. coli* reverse translation (DNASTAR Inc.), or Backtranslation tool v2.0 (Entelechon)), the DNA sequence encoding the linker region is determined. BamHI/SalI and PstI/XbaI/stop codon/HindIII restriction enzyme sequences are incorporated at either end, in the correct reading frames. The DNA sequence is screened (using software such as MapDraw, DNASTAR Inc.) for restriction enzyme cleavage sequences incorporated during the back translation. Any sequences that are found to be common to those required by the cloning system are removed manually from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004). This optimised DNA sequence is then commercially synthesized (for example by Entelechon, Geneart or Sigma-Genosys) and is provided in the pCR 4 vector. If it is desired to clone the linker out of pCR 4 vector, the vector (encoding the linker) is cleaved with either BamHI+SalI or PstI+XbaI combination restriction enzymes. This cleaved vector then serves as the recipient vector for insertion and ligation of either the LC DNA (cleaved with BamHI/SalI) or $H_N$ DNA (cleaved with PstI/XbaI). Once the LC or the $H_N$ encoding DNA is inserted upstream or downstream of the linker DNA, the entire LC-linker or linker-$H_N$ DNA fragment can the be isolated and transferred to the backbone clone.

As an alternative to independent gene synthesis of the linker, the linker-encoding DNA can be included during the synthesis or PCR amplification of either the LC or $H_N$.

Assembly and Confirmation of the Backbone Clone

The LC or the LC-linker is cut out from the pCR 4 cloning vector using BamHI/SalI or BamHI/PstI restriction enzymes digests. The PMAL expression vector is digested with the same enzymes but is also treated with calf intestinal protease (CIP) as an extra precaution to prevent re-circularisation. Both the LC or LC-linker region and the PMAL vector backbone are gel purified. The purified insert and vector backbone are ligated together using T4 DNA ligase and the product is transformed with TOP10 cells which are then screened for LC insertion using BamHI/SalI or BamHI/PstI restriction digestion. The process is then repeated for the $H_N$ or linker-$H_N$ insertion into the PstI/HindIII or SalI/HindIII sequences of the PMAL-LC construct.

Screening with restriction enzymes is sufficient to ensure the final backbone is correct as all components are already sequenced confirmed, either during synthesis or following PCR amplification. However, during the sub-cloning of some components into the backbone, where similar size fragments are being removed and inserted, sequencing of a small region to confirm correct insertion is required.

Example 9

Construction, Expression, and Purification of a $LH_N$/C-EGF Fusion Protein

Preparation of Spacer-EGF Insert

For presentation of an EGF sequence at the C-terminus of the $H_N$ domain, a DNA sequence is designed to flank the spacer and targeting moiety (TM) regions allowing incorporation into the backbone clone (SEQ ID NO:2). The DNA sequence can be arranged as BamHI-SalI-PstI-XbaI-spacer-EGF-stop codon-HindIII (SEQ ID NO:3). The DNA sequence can be designed using one of a variety of reverse translation software tools (for example EditSeq best *E. coli* reverse translation (DNASTAR Inc.), or Backtranslation tool v2.0 (Entelechon)). Once the TM DNA is designed, the additional DNA required to encode the preferred spacer is created in silico. It is important to ensure the correct reading frame is maintained for the spacer, EGF and restriction sequences and that the XbaI sequence is not preceded by the bases, TC which would result on DAM methylation. The DNA sequence is screened for restriction sequence incorporated and any additional sequences are removed manually from the remaining sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004). This optimised DNA sequence is then commercially synthesized (for example by Entelechon, Geneart or Sigma-Genosys) and is provided in the pCR 4 vector.

Insertion of Spacer-EGF into Backbone

In order to create a LC-linker-$H_N$-spacer-EGF construct (SEQ ID NO:4) using the backbone construct (SEQ ID NO:2) and the newly synthesised pCR 4-spacer-TM vector encoding the EGF TM (SEQ ID NO:3), the following two-step method is employed. Firstly, the $H_N$ domain is excised from the backbone clone using restriction enzymes PstI and XbaI and ligated into similarly digested pCR 4-spacer-EGF vector. This creates an $H_N$-spacer-EGF ORF in pCR 4 that can be excised from the vector using restriction enzymes PstI and HindIII for subsequent ligation into similarly cleaved backbone or expression construct. The final construct contains the LC-linker-$H_N$-spacer-EGF ORF (SEQ ID NO:4) for transfer into expression vectors for expression to result in a fusion protein of the sequence illustrated in SEQ ID NO:5.

Screening with restriction enzymes is sufficient to ensure the final backbone is correct as all components are already sequenced confirmed, either during synthesis or following PCR amplification. However, during the sub-cloning of some components into the backbone, where similar size fragments are being removed and inserted, sequencing of a small region to confirm correct insertion is required.

Alternative Construction Approach

As an alternative to the methodologies described above for the construction of $LH_N$/C-EGF, complete gene synthesis has been used to create a single DNA insert that encodes the LC, the $H_N$, linkers, spacers and a protease activation site. The synthetic DNA is designed to have a NdeI restriction site at the 5' end and a HindIII restriction site at the 3' end to facilitate direct cloning into expression vectors. The sequence of the engineered coding region is subject to the same codon utilisation analysis as described above. The sequence of the synthetic DNA is illustrated in SEQ ID NO:19, and the protein that it encodes is illustrated in SEQ ID NO:20.

Expression of $LH_N$/C-EGF Fusion Protein

Expression of the $LH_N$/C-EGF fusion protein is achieved using the following protocol. Inoculate 100 ml of modified TB containing 0.2% glucose and 100 μg/ml ampicillin in a 250 ml flask with a single colony from the $LH_N$/C-EGF expression strain. Grow the culture at 37° C., 225 rpm for 16 hours. Inoculate 1 L of modified TB containing 0.2% glucose and 100 μg/ml ampicillin in a 2 L flask with 10 ml of overnight culture. Grow cultures at 37° C. until an approximate OD600 nm of 0.5 is reached at which point reduce the temperature to 16° C. After 1 hour induce the cultures with 1 mM IPTG and grow at 16° C. for a further 16 hours.

Purification of $LH_N$/C-EGF Fusion Protein

Defrost falcon tube containing 25 ml 50 mM HEPES pH 7.2 200 mM NaCl and approximately 10 g of *E. coli* BL21 cell paste. Sonicate the cell paste on ice 30 seconds on, 30 seconds off for 10 cycles at a power of 22 microns ensuring the sample remains cool. Spin the lysed cells at 18 000 rpm, 4° C. for 30 minutes. Load the supernatant onto a 0.1 M NiSO4 charged Chelating column (20-30 ml column is sufficient) equilibrated with 50 mM HEPES pH 7.2 200 mM NaCl. Using a step gradient of 10 and 40 mM imidazole, wash away the non-specific bound protein and elute the fusion protein with 100 mM imidazole.

Figure 8:
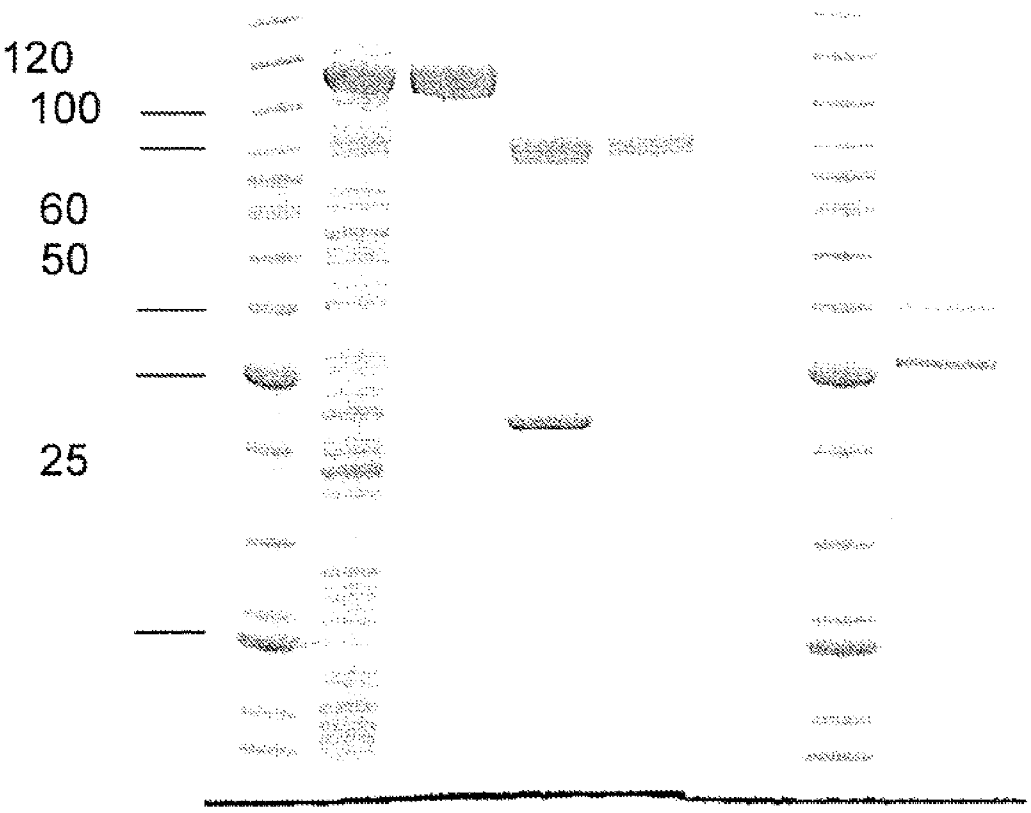
FIG. 8 shows purification of a $LH_N$/C-EGF fusion protein. Using the methodology outlined in Example 9, a $LH_N$/C-EGF fusion protein was purified from *E. coli* BL21 cells. Briefly, the soluble products obtained following cell disruption were applied to a nickel-charged affinity capture column. Bound proteins were eluted with 100 mM imidazole, treated with Factor Xa to activate the fusion protein and remove the maltose-binding protein (MBP) tag, then re-applied to a second nickel-charged affinity capture column. Samples from the purification procedure were assessed by SDS-PAGE. Lane 1 & 6: Molecular mass markers (kDa), lane 2: Clarified crude cell lysate, lane 3: First nickel chelating Sepharose column eluant, lane 4: Factor Xa digested protein, lane 5: Purified $LH_N$/C-EGF under non-reducing conditions, lane 7: Purified $LH_N$/C-EGF under reduced conditions.

Dialyse the eluted fusion protein against 5 L of 50 mM HEPES pH 7.2 200 mM NaCl at 4° C. overnight and measure the OD of the dialysed fusion protein. Add 1 unit of factor Xa per 100 μg fusion protein and incubate at 25° C. static overnight. Load onto a 0.1 M NiSO4 charged Chelating column (20-30 ml column is sufficient) equilibrated with 50 mM HEPES pH 7.2 200 mM NaCl. Wash column to baseline with 50 mM HEPES pH 7.2 200 mM NaCl. Using a step gradient of 10 and 40 mM imidazole, wash away the non-specific bound protein and elute the fusion protein with 100 mM imidazole. Dialyse the eluted fusion protein against 5 L of 50 mM HEPES pH 7.2 200 mM NaCl at 4° C. overnight and concentrate the fusion to about 2 mg/ml, aliquot sample and freeze at −20° C. Test purified protein using OD, BCA and purity analysis. FIG. 8 demonstrates the purified protein as analysed be SDS-PAGE.

Example 10

Construction, Expression and Purification of a $LH_N$/B-EGF Fusion Protein

Figure 9:
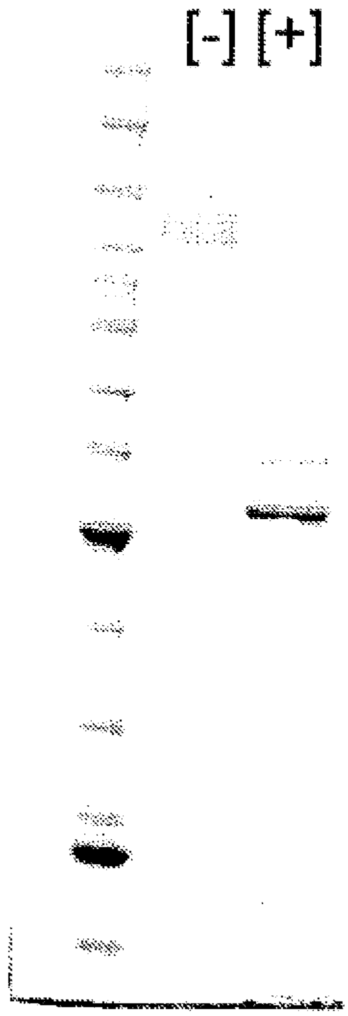
FIG. 9 shows purification of a $LH_N$/B-EGF fusion protein. Using the methodology outlined in Example 10, a $LH_N$/B-EGF fusion protein was purified from *E. coli* BL21 cells. Briefly, the soluble products obtained following cell disruption were applied to a nickel-charged affinity capture column. Bound proteins were eluted with 100 mM imidazole, treated with Factor Xa and enterokinase to activate the fusion protein and remove the maltose-binding protein (MBP) tag, then re-applied to a second nickel-charged affinity capture column. Samples from the purification procedure were assessed by SDS-PAGE. The final purified material in the absence and presence of reducing agent is identified in the lanes marked [−] and [+] respectively.

The LC-$H_N$ linker is designed using the methods described in example 9 using the B serotype linker arranged as BamHI-SalI-PstI-XbaI-spacer-EGF-stop codon-HindIII (SEQ ID NO:3). The $LH_N$/B-EGF fusion is then assembled using the $LH_N$/B backbone clone (SEQ ID NO:1) made using the methods described in example 7 and constructed using methods described in example 9. The final construct contains the LC-linker-$H_N$-spacer-EGF ORF (SEQ ID NO:6) for transfer into expression vectors for expression to result in a fusion protein of the sequence illustrated in SEQ ID NO:7. The resultant expression plasmid, PMAL $LH_N$/B-EGF is transformed into *E. coli* BL21 for recombinant protein expression. Expression and purification of the fusion protein was carried out as described previously except that enterokinase replaced factor Xa in the activation of the fusion protein. FIG. 9 demonstrates the purified protein as analysed by SDS-PAGE.

Example 11

Preparation and Purification of a $LH_N$/C-RGD Fusion Protein

Preparation of Spacer-RGD Insert

For presentation of an RGD sequence at the C-terminus of the $H_N$ domain, a DNA sequence is designed to flank the spacer and TM regions allowing incorporation into the backbone clone (SEQ ID NO:2). The DNA sequence can be arranged as BamHI-SalI-PstI-XbaI-spacer-SpeI-RGD-stop codon-HindIII (SEQ ID NO:8). The DNA sequence can be designed using one of a variety of reverse translation software tools (for example EditSeq best *E. coli* reverse translation (DNASTAR Inc.), or Backtranslation tool v2.0 (Entelechon)). Once the TM DNA is designed, the additional DNA required to encode the preferred spacer is created in silico. It is important to ensure the correct reading frame is maintained for the spacer, RGD and restriction sequences and that the XbaI sequence is not preceded by the bases, TC which would result on DAM methylation. The DNA sequence is screened for restriction sequence incorporated and any additional sequences are removed manually from the remaining sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004). This optimised DNA sequence is then commercially synthesized (for example by Entelechon, Geneart or Sigma-Genosys) and is provided in the pCR 4 vector.

Insertion of Spacer-RGD into Backbone

In order to create a LC-linker-$H_N$-spacer-RGD construct (SEQ ID NO:9) using the backbone construct (SEQ ID NO:2) and the newly synthesised pCR 4-spacer-TM vector encoding the RGD TM (SEQ ID NO:8), the following two-step method is employed. Firstly, the $H_N$ domain is excised from the backbone clone using restriction enzymes PstI and XbaI and ligated into similarly digested pCR 4-spacer-RGD vector. This creates an $H_N$-spacer-RGD ORF in pCR 4 that can be excised from the vector using restriction enzymes PstI and HindIII for subsequent ligation into similarly cleaved backbone or expression construct. The final construct contains the LC-linker-$H_N$-spacer-RGD ORF (SEQ ID NO:9) for transfer into expression vectors for expression to result in a fusion protein of the sequence illustrated in SEQ ID NO:10.

Screening with restriction enzymes is sufficient to ensure the final backbone is correct as all components are already sequenced confirmed, either during synthesis or following PCR amplification. However, during the sub-cloning of some components into the backbone, where similar size fragments are being removed and inserted, sequencing of a small region to confirm correct insertion is required.

Figure 10:
FIG. 10 shows purification of a $LH_N$/C-RGD fusion protein. Using the methodology outlined in Example 11, a $LH_N$/C-RGD fusion protein was purified from *E. coli* BL21 cells. Briefly, the soluble products obtained following cell disruption were applied to a nickel-charged affinity capture column. Bound proteins were eluted with 100 mM imidazole, treated with Factor Xa to activate the fusion protein and remove the maltose-binding protein (MBP) tag, then re-applied to a second nickel-charged affinity capture column. Samples from the purification procedure were assessed by SDS-PAGE. The final purified material in the absence and presence of reducing agent is identified in the lanes marked [−] and [+] respectively.

Expression and purification of the fusion protein was carried out as described in example 9. FIG. 10 demonstrates the purified protein as analysed by SDS-PAGE.

Example 12

Preparation and Purification of a $LH_N$/C-cyclic RGD Fusion Protein

Figure 11:
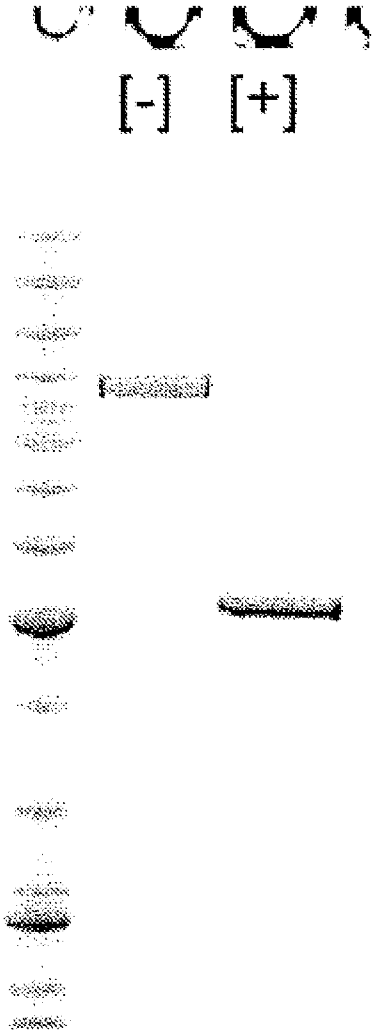
FIG. 11 shows purification of a $LH_N$/C-cyclic RGD fusion protein. Using the methodology outlined in Example 12, a $LH_N$/C-cyclic RGD fusion protein was purified from *E. coli* BL21 cells. Briefly, the soluble products obtained following cell disruption were applied to a nickel-charged affinity capture column. Bound proteins were eluted with 100 mM imidazole, treated with Factor Xa to activate the fusion protein and remove the maltose-binding protein (MBP) tag, then re-applied to a second nickel-charged affinity capture column. Samples from the purification procedure were assessed by SDS-PAGE. The final purified material in the absence and presence of reducing agent is identified in the lanes marked [−] and [+] respectively.

The LC-$H_N$ linker can be designed using the methods described in example 11 using the C serotype linker arranged as BamHI-SalI-PstI-XbaI-spacer-SpeI-cyclic RGD-stop codon-HindIII (SEQ ID NO:11). The $LH_N$/C-cyclic RGD fusion is then assembled using the $LH_N$/C backbone clone (SEQ ID NO:2) made using the methods described in example 8 and constructed using methods described in example 11. The final construct contains the LC-linker-$H_N$-spacer-cyclic RGD ORF (SEQ ID NO:11) for transfer into expression vectors for expression to result in a fusion protein of the sequence illustrated in SEQ ID NO:13. The resultant expression plasmid, PMAL $LH_N$/C-cyclic RGD was transformed into *E. coli* BL21 for recombinant protein expression. Expression and purification of the fusion protein was carried out as described in example 9. FIG. 11 demonstrates the purified protein as analysed by SDS-PAGE.

Example 13

Preparation and Purification of a LC/C-RGD-$H_N$/C Fusion Protein

Figure 12:
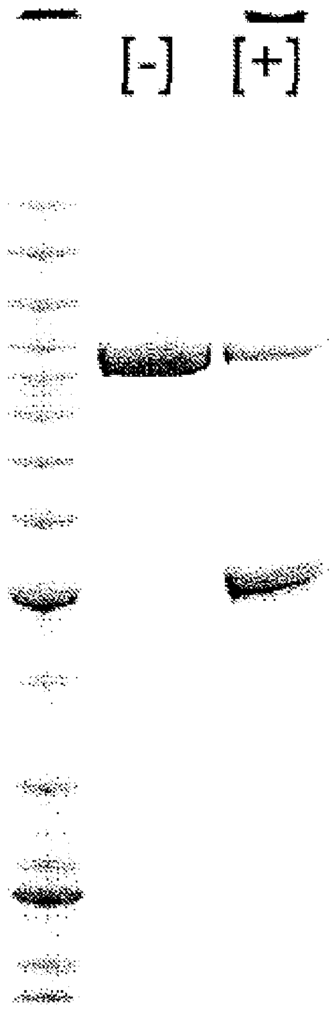
FIG. 12 shows purification of a LC/C-RGD-$H_N$/C fusion protein. Using the methodology outlined in Example 13, a LC/C-RGD-$H_N$/C fusion protein was purified from *E. coli* BL21 cells. Briefly, the soluble products obtained following cell disruption were applied to a nickel-charged affinity capture column. Bound proteins were eluted with 100 mM imidazole, treated with Factor Xa to activate the fusion protein and remove the maltose-binding protein (MBP) tag, then re-applied to a second nickel-charged affinity capture column. Samples from the purification procedure were assessed by SDS-PAGE. The final purified material in the absence and presence of reducing agent is identified in the lanes marked [−] and [+] respectively.

In order to create the LC-linker-RGD-spacer-$H_N$ construct (SEQ ID NO:15), the pCR 4 vector encoding the linker (SEQ ID NO:14) is cleaved with BamHI+SalI restriction enzymes. This cleaved vector then serves as the recipient vector for insertion and ligation of the LC/C DNA (SEQ ID NO:2) cleaved with BamHI+SalI. The resulting plasmid DNA is then cleaved with PstI+XbaI restriction enzymes and serves as the recipient vector for the insertion and ligation of the $H_N$/C DNA (SEQ ID NO:2) cleaved with PstI+XbaI. The final construct contains the LC-linker-RGD-spacer-$H_N$ ORF (SEQ ID NO:15) for transfer into expression vectors for expression to result in a fusion protein of the sequence illustrated in SEQ ID NO:16. The resultant expression plasmid, PMAL LC/C-RGD-$H_N$/C was transformed into *E. coli* BL21 for recombinant protein expression. Expression and purification of the fusion protein was carried out as described in example 9. FIG. 12 demonstrates the purified protein as analysed by SDS-PAGE.

Alternative Construction Approach

As an alternative to the methodologies described above for the construction of LC-linker-RGD-spacer-$H_N$, complete gene synthesis has been used to create a single DNA insert that encodes the LC, the $H_N$, linkers, spacers and a protease activation site. The synthetic DNA is designed to have a NdeI restriction site at the 5' end and a HindIII restriction site at the 3' end to facilitate direct cloning into expression vectors. The sequence of the engineered coding region is subject to the same codon utilisation analysis as described above. The sequence of the synthetic DNA is illustrated in SEQ ID NO:17, and the protein that it encodes is illustrated in SEQ ID NO:18.

Example 14

VAMP Cleavage Activity Assay

Figure 13:
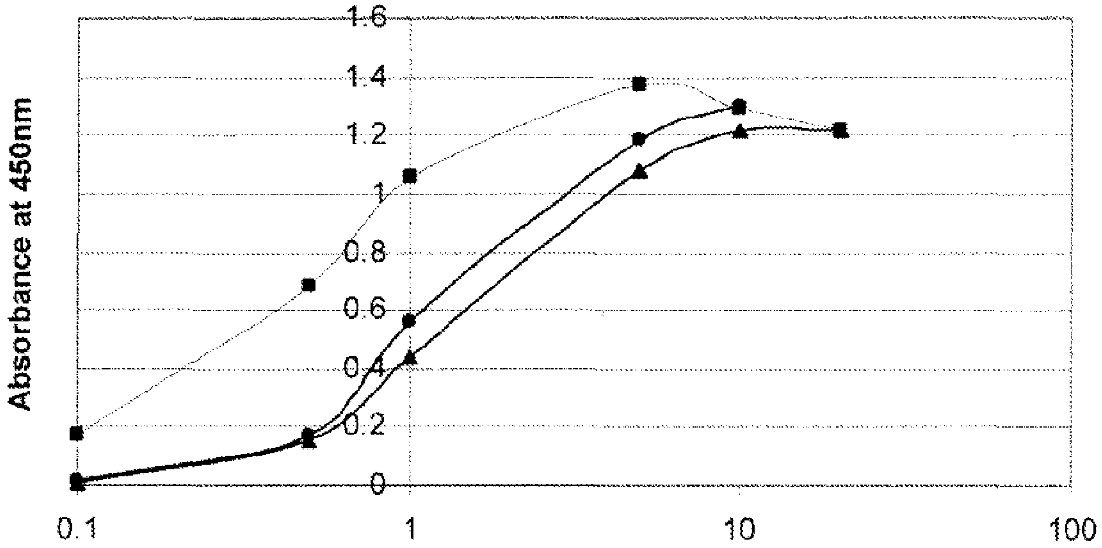
FIG. 13 shows VAMP cleavage activity of $LH_N$/B-EGF. Using the methodology outlined in Example 14, BoNT/B (•), $LH_N$/B (■) and $LH_N$/B-EGF (▲) were assayed for VAMP cleavage activity.

A range of concentrations of $LH_N$/B-EGF in cleavage buffer (50 mM HEPES pH7.4, 10 mM DTT, 20 μM ZnCl2, 1% FBS) are incubated with biotinylated VAMP substrate (1 mg/ml) for two hours at 37° C. in a shaking incubator. The cleavage reaction is transferred to a washed 96-well streptavidin coated plate and incubated at 37° C. in a shaking incubator for 5 minutes. The plate is washed three times with PBS-0.1% tween-20 (PBS-T). The wells are blocked with blocking buffer (5% FCS in PBS-T) for 1 hour at 37° C. The primary antibody (anti-FESS) is added at a dilution of 1 in 500 in blocking buffer and the plate is incubated at 37° C. for 1 hour. The plate is washed three times with PBS-T and the secondary antibody (anti guinea pig HRP conjugate) diluted 1 in 1000 in blocking buffer is applied. Following 1 hour incubation at 37° C. the plate is developed with bioFX TMB substrate. Colour development is allowed to proceed for 1-5 minutes and then stopped with stop solution. The absorbance is measured at 450 nm. FIG. 13 shows the VAMP cleavage activity of $LH_N$/B-EGF fusion protein.

Example 15

Effect of EGF-$LH_N$/C on Secreting Cell Lines

Cell Cultivation

NCI-H292 (human mucoepimodial) cells were seeded into six well plates (Costar) four days prior to use from stocks grown in large 75 cm2 flasks (Nunc). The cells were cultured in RPMI+10% foetal bovine serum (FBS)+2 mM L-glutamine glutamine in a humidified 5% CO2 incubator at 370 C. A549 (human lung adencocarcinoma) cells were seeded into six well plates (Costar) four days prior to use from stocks grown in large 75 cm2 flasks (Nunc). The cells were cultured in DMEM+10% FBS+2 mM L-glutamine in a humidified 5% CO2 incubator at 37° C. In both cases the cells were used at 80% confluence in the wells. Prior to all treatments, the cells were serum-starved for 24 hours.

Inhibition of Mucin Release Following Application of EGF-$LH_N$/C

Both NCI-H292 and A549 cells were treated with various concentrations of fusion molecule for 24 hours in serum-free medium for the respective cell line in a humidified 5% CO2 incubator at 37° C. The media was removed and fresh serum-free medium containing the fusion molecule was added and the cells incubated plus the stimulant EGF/TNF alpha (20 ng/ml and 25 ng/ml respectively) for a further 48 hours and the cells incubated in a humidified 5% CO2 incubator at 37° C. Following stimulation, the media were collected, stored at −20° C. and analysed for mucin content using an enzyme-linked lectin assay (ELLA).

Detection of Released Mucus in Cell Culture Medium

Lectin derived from *Helix pomatia* (edible snail), which binds to specific terminal sugars in mucin glycoproteins, was adhered to a ninety-six well Maxisorp™ plate in phosphate buffered saline (PBS) pH 6.8 for one hour at 37° C. Excess PBS plus lectin were removed from the plate by washing with 0.5 M NaCl, PBS, 0.1% Tween 20, pH7.4. Cell culture medium collected from treated cells was added and the plate incubated for one hour at 37° C. The plates were then washed in 0.5 M NaCl, PBS, 0.1% Tween 20, pH 7.4 before adding Horseradish Peroxidase conjugated *Helix pomatia* lectin in PBS pH.7.4. Following a further wash step, the assay was developed using OPD (o-phenylenediamine dihydrochloride) peroxidase substrate for ten minutes at 37° C. The reaction was terminated with 2% H2SO4 (final concentration) and the absorbance at 492 nm read using a plate reader. Standard curves using human mucin prepared from sputum samples according to literature precedence and medium only controls were included on each Maxisorp™ plate.

Detection of Mucin Release and Cell Mucin Content Using Western Blotting Technique Cells treated with EGF-$LH_N$/C and stimulated were lysed in buffer and run on an agarose gel, transferred to nitrocellulose membranes and probed with Muc5AC monoclonal antibodies (Kirkham., et al 2002 Biochem. J. 361: pp 537). The bands were detected using secondary antibodies conjugated to horseradish peroxidase and the resultant band densities were scanned. Media from treated cells was also analysed using this method.

Cell Viability Assay

Cells were cultured in 6 well plates, the supernatant was removed and MTT (3-[4,5-dimethylthiazol-2-yl]-2,5-diphenyltetrazolium bromide) was added per well and incubated until a purple tinge was visible. The MTT was removed, and DMSO was added to solubilize the cells and the absorbance read at 550 nm. Results are expressed as percentage baseline control viability with control set at 100% (Mosmann 1983).

Inhibition of Mucus Release Following Application of EGF-$LH_N$/C

Figure 14:
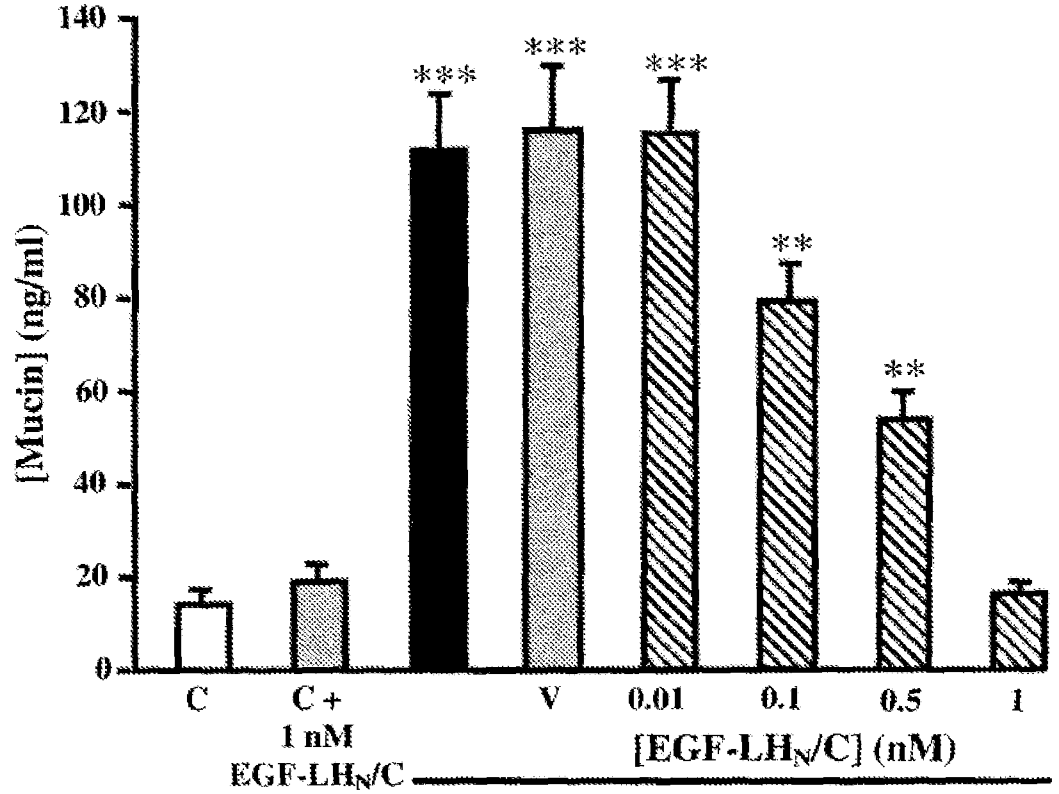
FIG. 14 shows effect of EGF-$LH_N$/C on EGF/TNF alpha-induced mucin secretion in A549 cells. A549 cells were treated with the fusion or vehicle or medium alone for 24 hr followed by a 48 hr stimulation of the cells with EGF/TNF alpha (Stim) in the presence of the construct. Vehicle treated cells received fresh vehicle plus medium only. Media was collected and assayed for mucin content using the ELLA method with a human mucin standard curve. All mucin levels are shown in ng/ml calculated from the human mucin standard curve within each ELLA plate. Each concentration was assessed in triplicate and the figure is representative of seven experiments. N=7

FIG. 14 shows a dose-response curve of mucus release from A549 cells. The figure shows the clear inhibition of mucus release from these cells following treatment with an IC50 of 0.4 nM. Data shown is from seven independent experiments. FIG. 15 shows that the fusion EGF-$LH_N$/C inhibited mucin release in a dose-dependent manner from NCI-H292 cells. Data from two different cell lines indicates that the fusion functions as proposed and blocks secretion of mucin from the cells.

EGF-$LH_N$/C does not Affect Viability of A549 or NCI-H292 Cells

FIGS. 16 and 17 show that cell viability as measured by MTT assay is not affected by EGF-$LH_N$/C, indicating that reduction of mucin secretion is not due to cell death.

Effect of EGF-$LH_N$/C on Mucin Content in Treated Cells

EGF-$LH_N$/C blocks release of mucin from stimulated cells (FIGS. 14 & 15) through cleavage of the SNARE protein syntaxin (FIG. 18). Concomitant with a decrease in mucin release as the EGF-$LH_N$/C concentration increases is an increase in the amount of mucin detected in the treated cells. FIG. 19 shows from two independent experiments that as level of MUC5AC remaining in a treated cell (intracellular mucin) increases as the EGF-$LH_N$/C concentration increases. FIG. 20 shows a similar result but with MUC5B.

Example 16

In Vitro Cleavage of a Snare Protein by EGF-$LH_N$/C

Cleavage of the Snare Mediated Protein in Cells Following Treatment with EGF-$LH_N$/C The fusion EGF-$LH_N$/C can obtain entry to cells and traffic to the SNARE proteins located near the plasma membrane. Cleavage of the SNARE protein Syntaxin by the EGF-$LH_N$/C fusion inhibits release of mucin from the cell. FIG. 18 shows syntaxin was cleaved by EGF-$LH_N$/C in a concentration-dependent manner in NCI-H292 cells. Cells were treated with 300 μg/ml EGF and/or 300 μg/ml $LH_N$/C or various concentrations of EGF-$LH_N$/C in serum-free medium for 3 days. Membrane proteins were extracted using chloroform/methanol and analysed by western blotting using a rabbit polyclonal antibody raised against the cleavage site peptide sequence of the smaller C-terminal syntaxin cleavage product, AVKY (SEQ ID NO: 39), as described previously (Sutton et al., 2005 Prot. Purif. Exp. 31:pp 41). Neither EGF alone, nor $LH_N$/C alone nor EGF and $LH_N$/C in combination were able to cleave syntaxin in the intact cells. These results confirm that the recombinant EGF-$LH_N$/C possesses a functional endopeptidase activity and is able to gain access to the interior of intact NCI-H292 cells.

Example 17

Effect of $LH_N$/C on Stimulated Mucin Secretion

Effect of $LH_N$/C on Mucin Release from A549 Cells

FIG. 21 shows that treatment of A549 cells with $LH_N$/C had no effect on the release of detectable mucin indicating the requirement for the ligand, in this case EGF, to allow the fusion to gain access to the cell and the SNARE mediated secretion apparatus.

Cells treated for 24 hr with 1 nM $LH_N$/C then stimulated for 48 hr with EGF/TNF alpha in the continued presence of $LH_N$/C showed no inhibition in mucin secretion as measured using the ELLA. Cells treated 24 hr with EGF-$LH_N$/C then stimulated for 48 hr with EGF/TNF alpha in the presence of EGF-$LH_N$/C showed inhibition of mucin secretion in the same experiment.

Example 18

Effect of EGF-$LH_N$/C on Baseline Secretion

FIGS. 14 and 15 show that treatment of cells for 72 hours with 1 nm EGF-does not affect baseline secretion in either A549 cells or NCI-H292 cells.

Example 19

Effect of EGF-$LH_N$/B on Secreting Cells

See example 15 for cell cultivation and released mucin detection.

Inhibition of Mucin Release from A549 Cells Following Treatment with EGF-$LH_N$/B FIG. 22 shows a dose-response curve for EGF-$LH_N$/B in A549 cells. There is an inhibition of mucin release from these cells following treatment. The cells were treated with the fusion or vehicle or medium alone for 48 hour followed by a 24 hour stimulation of the cells with EGF/TNF alpha (Stimulus) in the presence of the fusion. Vehicle treated cells received fresh vehicle plus medium only.

Example 20

Effect of LC/C-RGD-$LH_N$/C on Secreting Cells

See example 15 for cell cultivation and mucin detection

Inhibition of mucin release from A549 cells following treatment with LC/C-RGD-$LH_N$/C A549 cells were treated for 48 hours with various concentrations of LC/C-RGD-$LH_N$/C followed by stimulation of cells using EGF and TNF alpha (20 ng/ml and 25 ng/ml respectively) for 24 hours in the presence of LC/C-RGD-$LH_N$/C. FIG. 23 shows a dose-dependent decrease in mucin release. The Integrin-binding ligand sequence enables the $LH_N$/C to enter the cells thereby inhibiting mucin release.

Example 21

Effect of RGD-$LH_N$/C on Secreting Cells

Inhibition of Mucin Release from A549 Cells Following Treatment with RGD-$LH_N$/C A549 cells were treated for 48 hours with various concentrations of RGD-$LH_N$/C followed by stimulation of cells using EGF and TNF alpha (20 ng/ml and 25 ng/ml respectively) for 24 hours in the presence of RGD-$LH_N$/C. FIG. 24 shows a dose-dependent decrease in mucin release. The Integrin-binding ligand sequence enables the $LH_N$/C to enter the cells thereby inhibiting mucin release.

Example 22

Effect of $LH_N$/C-cyclic-RGD on Secreting Cells

Inhibition of mucin release from A549 cells following treatment with $LH_N$/C-cyclic-RGD A549 cells were treated for 48 hours with various concentrations of $LH_N$/C-cyclic-RGD followed by stimulation of cells using EGF and TNF alpha (20 ng/ml and 25 ng/ml respectively) for 24 hours in the presence of $LH_N$/C-cyclic-RGD. FIG. 25 shows a dose-dependent decrease in mucin release. The Integrin-binding ligand sequence enables the $LH_N$/C to enter the cells thereby inhibiting mucin release.

Example 23

Other Growth Factors as Ligands for Fusion Molecules that Inhibit Secretion From Mucous-Secreting Cells Vascular Endothelial Growth Factor
Platelet-Derived Growth Factor
Keratinocyte Growth Factor
Hepatocyte Growth Factor
Transforming Growth Factor—alpha
Transforming Growth Factor—beta Example 24

Other Peptides as Ligands for Fusion Molecules that Inhibit Secretion from Mucous-Secreting Cells Atrial Natriuretic Peptide as a ligand to create ANP-$LH_N$/C: Ligand receptor is found in lung. Ligand-receptor become internalised. High receptor affinity.

Vasoactive Intestinal Polypeptide as a ligand to create VIP-$LH_N$/C: Good receptor affinity. Receptor expressed in tracheal and bronchial epithelial cells and mucous cells of submucosal gland.

Phage display peptide THALW(H)T (SEQ ID NO: 34) as a ligand to create THALW(H)T-$LH_N$/C: THAL(H)WT (SEQ ID NO: 44) binds to apical surface of human bronchial and tracheal epithelial cells.

Example 25

Other Integrin-Binding Ligands as Ligands for Clostridial Endopeptidase-based Fusion Molecules that Inhibit Secretion from Mucous-Secreting Cells Multivalent RGD motif as a ligand to create mvRGD-$LH_N$/C: High ligand receptor affinity. Integrin targeted is highly lung-specific and expressed on human bronchial epithelial cells.

GRGDSP (SEQ ID NO: 37)
GRGESP (SEQ ID NO: 38)
Vitronectin
Fibronectin
Lamimin
Fibrinogen
Heparin
Phytohaemagglutinin Example 26

Clinical Example

A 56 year old male suffering from chronic bronchitis (FEV1 reduced to 80% of normal predicted value; daily sputum volume of 30 ml) presents at his GP. Despite treatment with inhaled steroids, the patient presents with difficulty in performing everyday tasks due continued shortness of breath. The GP prescribes a 6-month course of EGF-$LH_N$/C (as prepared in Example 11) in nebuliser form, 80 μg to be taken monthly. Following discussion with the physician, the patient selects the most appropriate nebuliser for their personal situation from a range of suitable devices. After a single dose of EGF-$LH_N$/C the patient experiences reduced sputum volume (to 15 ml) and an improvement in FEV1 (to 90%). Further treatment enhances these parameters further and improves quality of life.

Example 27

Clinical Example

A 14 year old female suffering from cystic fibrosis presents at her GP. Despite treatment with pulmozyme and extensive physiotherapy, the patient's respiratory performance (as measured by FEV1) continues to decline. The GP prescribes a 6-month course of RGD peptide-$LH_N$/C (as prepared in Example 13) in nebuliser form, 80 μg to be taken monthly immediately after physiotherapy. Following discussion with the physician, the patient selects the most appropriate nebuliser for their personal situation from a range of suitable devices. After a single dose of RGD peptide-$LH_N$/C the patient experiences an improvement in FEV1. Further treatment enhances respiratory performance further and improves quality of life.

SEQ ID LIST

SEQ ID NO:1 DNA sequence of $LH_N$/B
SEQ ID NO:2 DNA sequence of $LH_N$/C
SEQ ID NO:3 DNA sequence of the EGF linker
SEQ ID NO:4 DNA sequence of the EGF-C fusion
SEQ ID NO:5 Protein sequence of the EGF-C fusion
SEQ ID NO:6 DNA sequence of the EGF-B fusion
SEQ ID NO:7 Protein sequence of the EGF-B fusion
SEQ ID NO:8 DNA sequence of the RGD linker
SEQ ID NO:9 DNA sequence of the RGD-C fusion
SEQ ID NO:10 Protein sequence of the RGD-C fusion
SEQ ID NO:11 DNA sequence of the cyclic RGD linker
SEQ ID NO:12 DNA sequence of the cyclic RGD-C fusion
SEQ ID NO:13 Protein sequence of the cyclic RGD-C fusion
SEQ ID NO:14 DNA sequence of the LC/C-RGD-$H_N$/C linker
SEQ ID NO:15 DNA sequence of the LC/C-RGD-$H_N$/C fusion
SEQ ID NO:16 Protein sequence of the LC/C-RGD-$H_N$/C fusion
SEQ ID NO:17 DNA sequence of the fully synthesised LC/C-RGD-$H_N$/C fusion
SEQ ID NO:18 Protein sequence of the fully synthesised LC/C-RGD-$H_N$/C fusion
SEQ ID NO:19 DNA sequence of the fully synthesised EGF-$LH_N$/C fusion
SEQ ID NO:20 Protein sequence of the fully synthesised EGF-$LH_N$/C fusion
SEQ ID NO:21 Protein sequence from influenza virus
SEQ ID NO:22 Substance P peptide sequence
SEQ ID NO:23 Substance P peptide sequence with N-terminal Cys
SEQ ID NO:24 Protein sequence for factor Xa
SEQ ID NO:25 Protein sequence for enterokinase
SEQ ID NO:26 Protein sequence for TEV protease
SEQ ID NO:27 Protein sequence for precission
SEQ ID NO:28 Protein sequence for thrombin
SEQ ID NO:29 Integrin binding peptide sequence
SEQ ID NO:30 Integrin binding peptide sequence
SEQ ID NO:31 Cyclic RGD peptide
SEQ ID NO:32 Linear integrin binding sequence
SEQ ID NO:33 Cyclic integrin binding sequence

We claim:

1. A single-chain fusion protein comprising:

(a) a light chain (L-chain) or L-chain fragment of a clostridial neurotoxin, which L-chain or L-chain fragment includes the active proteolytic enzyme domain of the L-chain;

(b) a targeting domain comprising or consisting of a growth factor;

(c) a translocating domain that translocates the L-chain or L-chain fragment into the target cell; and (d) a site for cleavage by a proteolytic enzyme; and wherein said polypeptide lacks a functional heavy chain (H-chain) of a clostridial neurotoxin and therefore does not bind to clostridial neurotoxin receptors with the same affinity as native clostridial neurotoxin;

wherein the growth factor is selected from the group consisting of platelet-derived growth factor, keratinocyte growth factor, and hepatocyte growth factor; and wherein the translocating domain is a clostridial neurotoxin heavy chain $H_N$ domain or a translocating domain from a bacterial toxin or a viral toxin.

2. The single-chain fusion protein according to claim 1, wherein the cleavage site is selected from the group consisting of: IEGR (SEQ ID NO: 24); DDDDK (SEQ ID NO: 25); EXXYXQSG (SEQ ID NO: 26); LEVLFQGP (SEQ ID NO: 27); LVPRGS (SEQ ID NO: 28); HY and YH.

3. The single-chain fusion protein according to claim 1, wherein said cleavage site is not present in a native clostridial neurotoxin.

4. The single-chain fusion protein according to claim 1, wherein said cleavage site is located between the L-chain or L-chain fragment and the translocating domain.

5. The single-chain fusion protein according to claim 1, wherein the cleavage site is cleavable by a proteolytic enzyme selected from the group consisting of: factor Xa; enterokinase; TEV protease; precission; thrombin; and generase.

6. A single-chain fusion protein comprising:

(a) a light chain (L-chain) or L-chain fragment of a clostridial neurotoxin, which L-chain or L-chain fragment includes the active proteolytic enzyme domain of the L-chain;

(b) a targeting domain comprising or consisting of a growth factor;

(c) a translocating domain that translocates the L-chain or L-chain fragment into the target cell; and (d) a site for cleavage by a proteolytic enzyme; and wherein said polypeptide lacks a functional heavy chain (H-chain) of a clostridial neurotoxin and therefore does not bind to clostridial neurotoxin receptors with the same affinity as native clostridial neurotoxin;

wherein the growth factor is selected from the group consisting of epidermal growth factor (EGF), vascular endothelial growth factor, platelet-derived growth factor, keratinocyte growth factor, hepatocyte growth factor, transforming growth factor alpha, and transforming growth factor beta; and wherein the translocating domain comprises a translocating domain of a bacterial toxin selected from the group consisting of diphtheria toxin and Domain II of *pseudomonas* exotoxin or a viral toxin selected from the group consisting of influenza virus haemagglutinin, Semliki Forest virus fusogenic protein, Vesicular Stomatitis virus glycoprotein G, SER virus F protein, and foamy virus envelope glycoprotein.

7. The single-chain fusion protein of claim 6, wherein the translocating domain comprises a viral toxin selected from the group consisting of influenza virus haemagglutinin, Semliki Forest virus fusogenic protein, Vesicular Stomatitis virus glycoprotein G, SER virus F protein, and foamy virus envelope glycoprotein.

8. The single-chain fusion protein according to claim 6, wherein the translocating domain comprises a bacterial toxin selected from the group consisting of diphtheria toxin and Domain II of *pseudomonas* exotoxin.

9. The single-chain fusion protein according to claim 6, wherein the cleavage site is selected from the group consisting of: IEGR (SEQ ID NO: 24); DDDDK (SEQ ID NO: 25); EXXYXQSG (SEQ ID NO: 26); LEVLFQGP (SEQ ID NO: 27); LVPRGS (SEQ ID NO: 28); HY and YH.

10. The single-chain fusion protein according to claim 6, wherein said cleavage site is not present in a native clostridial neurotoxin.

11. The single-chain fusion protein according to claim 6, wherein said cleavage site is located between the L-chain or L-chain fragment and the translocating domain.

12. The single-chain fusion protein according to claim 6, wherein the cleavage site is cleavable by a proteolytic enzyme selected from the group consisting of: factor Xa; enterokinase; TEV protease; precission; thrombin; and generase.

13. A method comprising:

contacting a single-chain fusion protein as set forth in claim 6 with a proteolytic enzyme that cleaves said site for cleavage; and cleaving said single-chain fusion protein at said site for cleavage, thereby providing a di-chain polypeptide wherein the light chain (L-chain) or L-chain fragment (a) and the translocating domain (c) are linked together by disulphide bond.

14. The method of claim 13, further comprising contacting the di-chain polypeptide with a cell.

* * * * *